US010080670B2

(12) United States Patent
Sandstrom et al.

(10) Patent No.: US 10,080,670 B2
(45) Date of Patent: Sep. 25, 2018

(54) APPARATUS AND METHOD FOR STABILIZING ADJACENT BONE PORTIONS

(71) Applicants: Jason Sandstrom, Marquette, MI (US); Fran Korhonen, Negaunee, MI (US); Matthew N. Songer, Marquette, MI (US)

(72) Inventors: Jason Sandstrom, Marquette, MI (US); Fran Korhonen, Negaunee, MI (US); Matthew N. Songer, Marquette, MI (US)

(73) Assignee: J.M. LONGYEAR MANUFACTURING LLC, Marquette, MI (US)

(*) Notice: Subject to any disclaimer, the term of this patent is extended or adjusted under 35 U.S.C. 154(b) by 52 days.

(21) Appl. No.: 15/422,444

(22) Filed: Feb. 1, 2017

(65) Prior Publication Data

US 2017/0143513 A1 May 25, 2017

Related U.S. Application Data

(60) Division of application No. 14/453,520, filed on Aug. 6, 2014, now Pat. No. 9,592,131, which is a (Continued)

(51) Int. Cl.
*A61B 17/88* (2006.01)
*A61F 2/46* (2006.01)
(Continued)

(52) U.S. Cl.
CPC ........ *A61F 2/4611* (2013.01); *A61F 2/30767* (2013.01); *A61F 2/4455* (2013.01); *A61B 17/1757* (2013.01); *A61F 2002/3037* (2013.01); *A61F 2002/3038* (2013.01); *A61F 2002/30135* (2013.01); *A61F 2002/30166* (2013.01); *A61F 2002/30172* (2013.01); *A61F 2002/30401* (2013.01); *A61F 2002/30598* (2013.01); *A61F 2002/30904* (2013.01);
(Continued)

(58) Field of Classification Search
CPC ............................. A61B 17/88; A61B 17/8872
USPC ......... 623/17.11–17.16; 606/246, 87, 90, 96, 606/99, 105, 86 A, 279
See application file for complete search history.

(56) References Cited

U.S. PATENT DOCUMENTS

2009/0209967 A1* 8/2009 Evans ................... A61F 2/4611 606/99
2010/0249795 A1* 9/2010 DiMauro .............. A61F 2/4611 606/99

* cited by examiner

*Primary Examiner* — Ellen C Hammond
*Assistant Examiner* — Christina Negrellirodrigue
(74) *Attorney, Agent, or Firm* — Device Patent LLC

(57) ABSTRACT

Instruments, kits, and methods are disclosed for installing an implant spacer through an incision and down a surgical corridor. The instruments also serve to align a drill guide and align and insert a spacer stabilizer for stabilization of adjacent bone portions. The instrument comprises an elongated guide bar body, an inserter face at a distal end of said guide bar body for abutting an instrument attachment portion of a spacer, a connection tip portion for securing a spacer against an inserter face, and a guide portion of said elongated guide bar body for aligning instruments with said spacer and for introducing a stabilizer to secure the spacer in a predetermined position between the bone portions. Included is a retractable graft block for securing graft material within an aperture of said spacer during insertion of the spacer.

20 Claims, 45 Drawing Sheets

Related U.S. Application Data continuation-in-part of application No. 13/347,526, filed on Jan. 10, 2012, now Pat. No. 9,486,324, and a continuation-in-part of application No. 12/692,503, filed on Jan. 22, 2010, now Pat. No. 8,157,865.

(60) Provisional application No. 61/862,671, filed on Aug. 6, 2013, provisional application No. 61/431,235, filed on Jan. 10, 2011.

(51) Int. Cl.
*A61F 2/44* (2006.01)
*A61F 2/30* (2006.01)
*A61B 17/17* (2006.01)

(52) U.S. Cl.
CPC ................. *A61F 2002/4475* (2013.01); *A61F 2310/00017* (2013.01); *A61F 2310/00023* (2013.01); *A61F 2310/00179* (2013.01); *A61F 2310/00359* (2013.01)

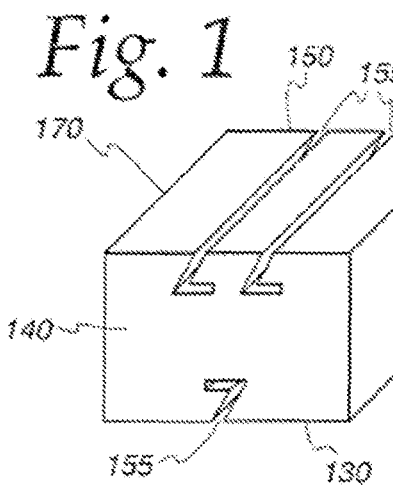
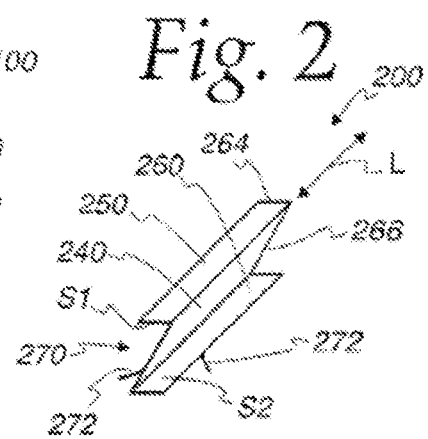
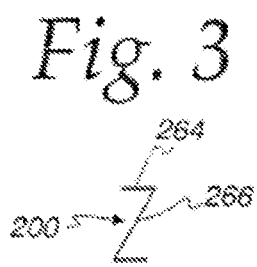
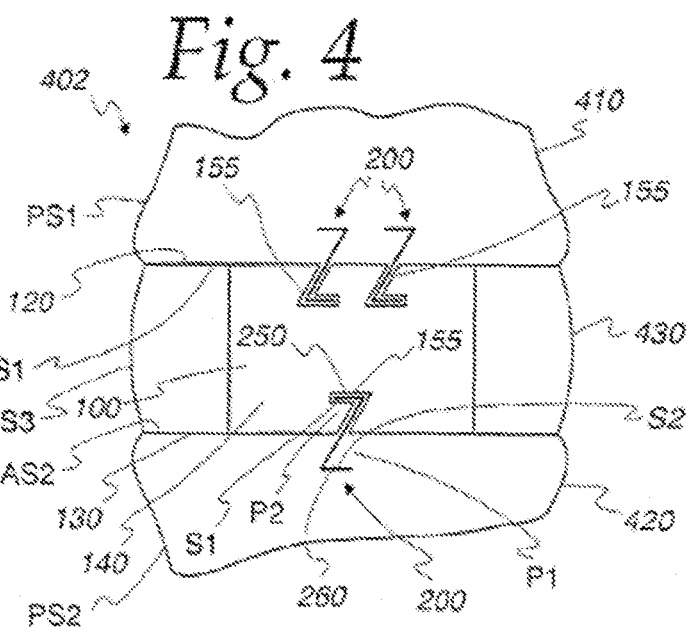
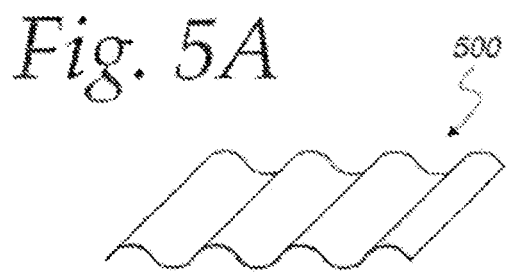
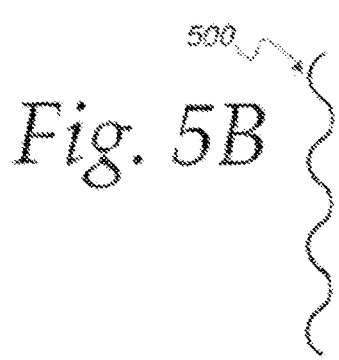

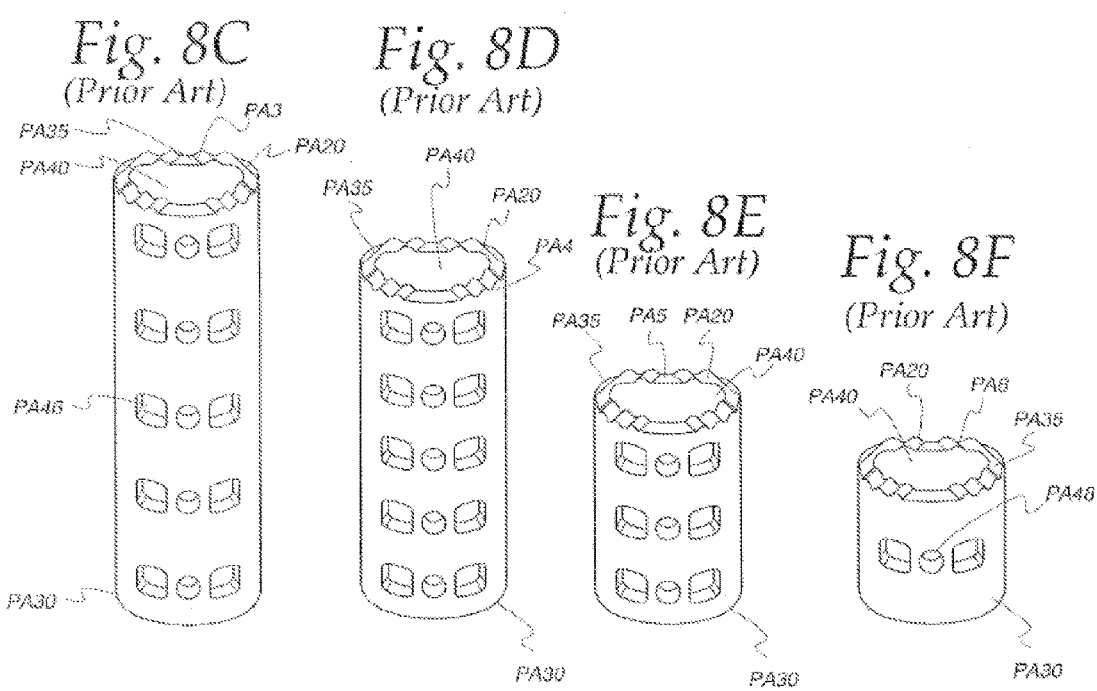

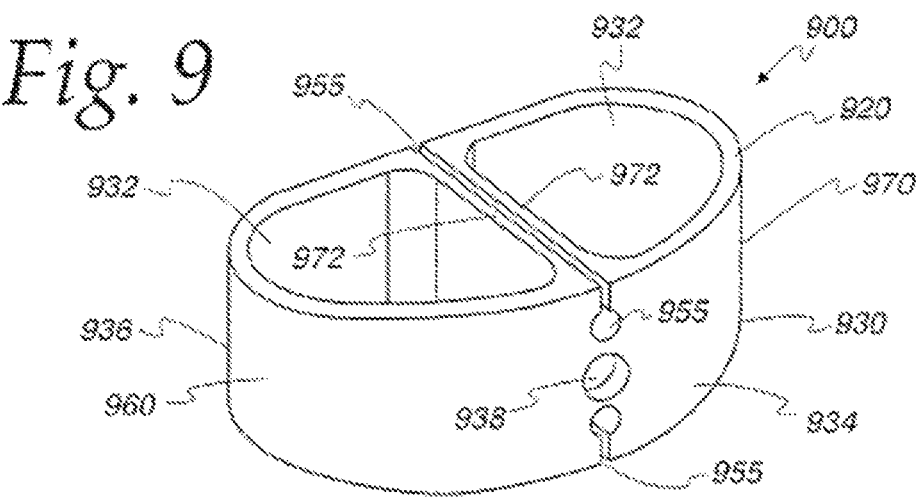
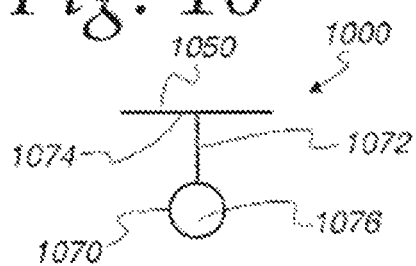
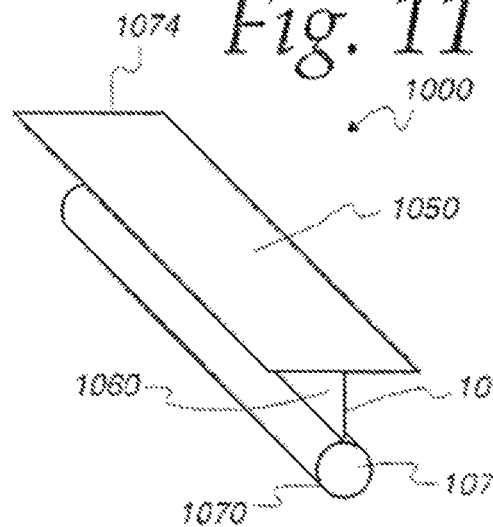
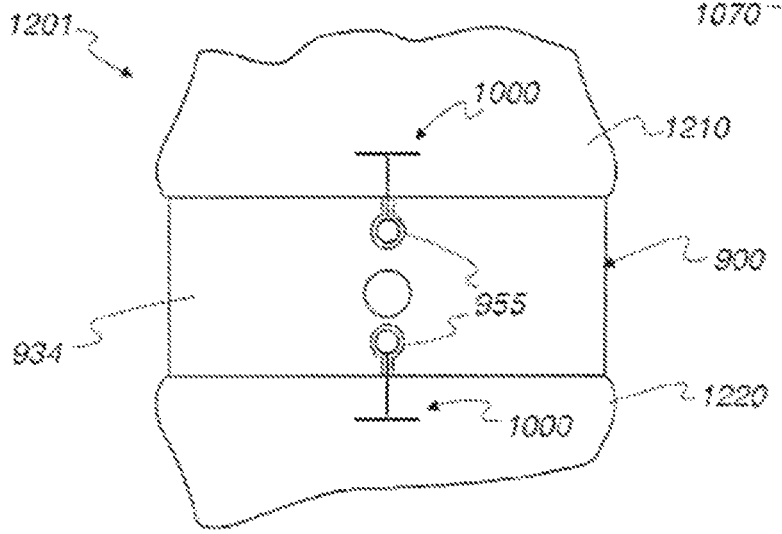

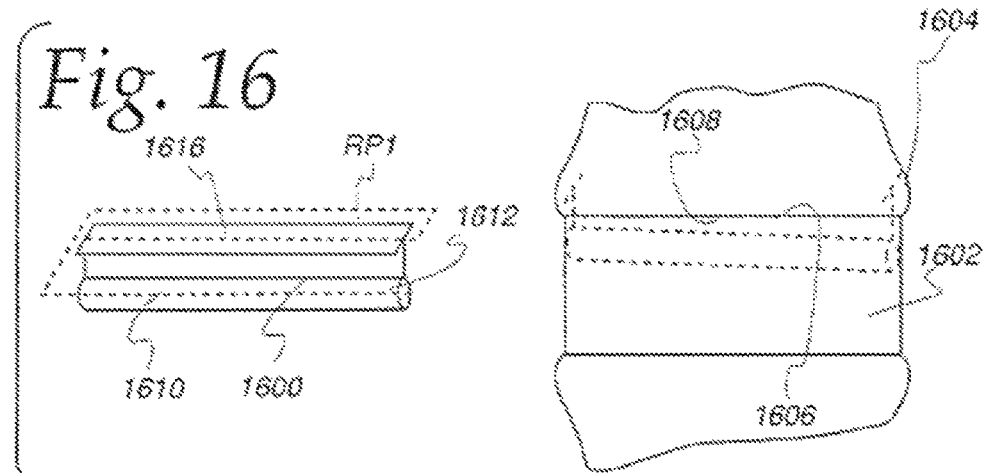
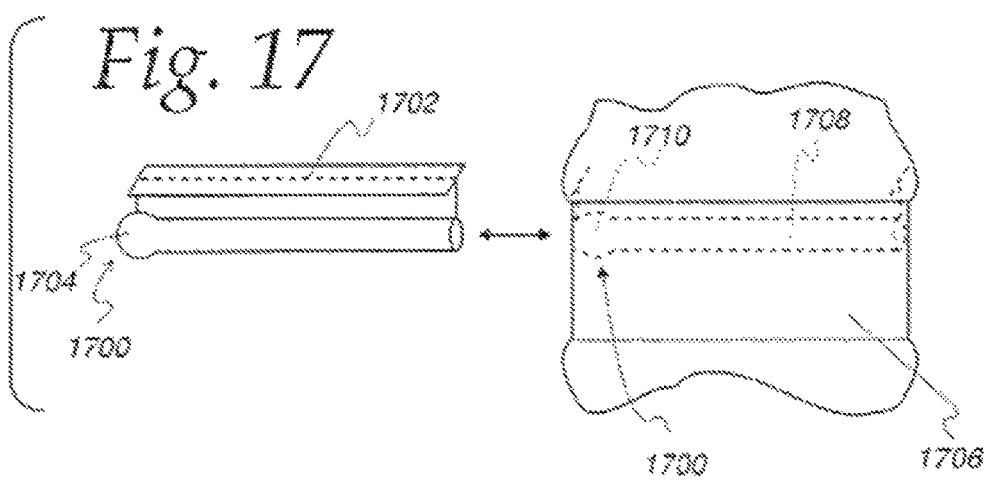
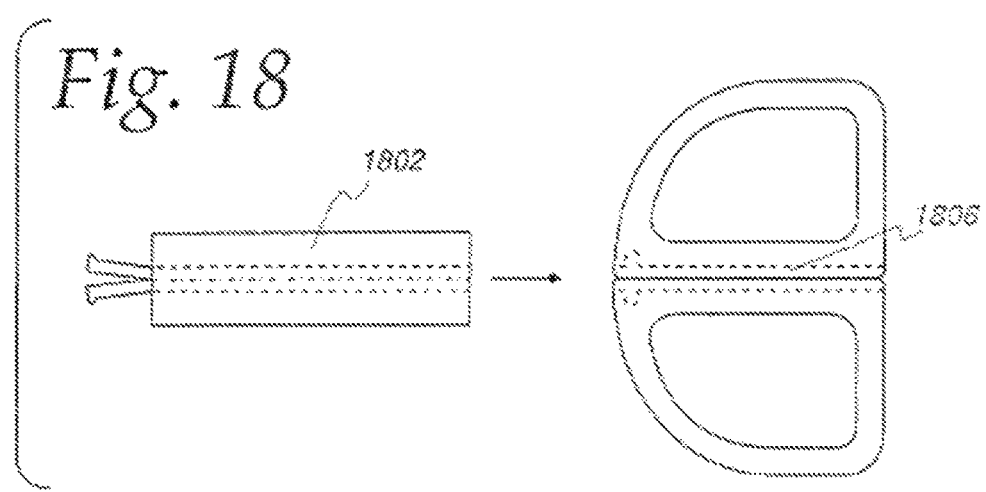

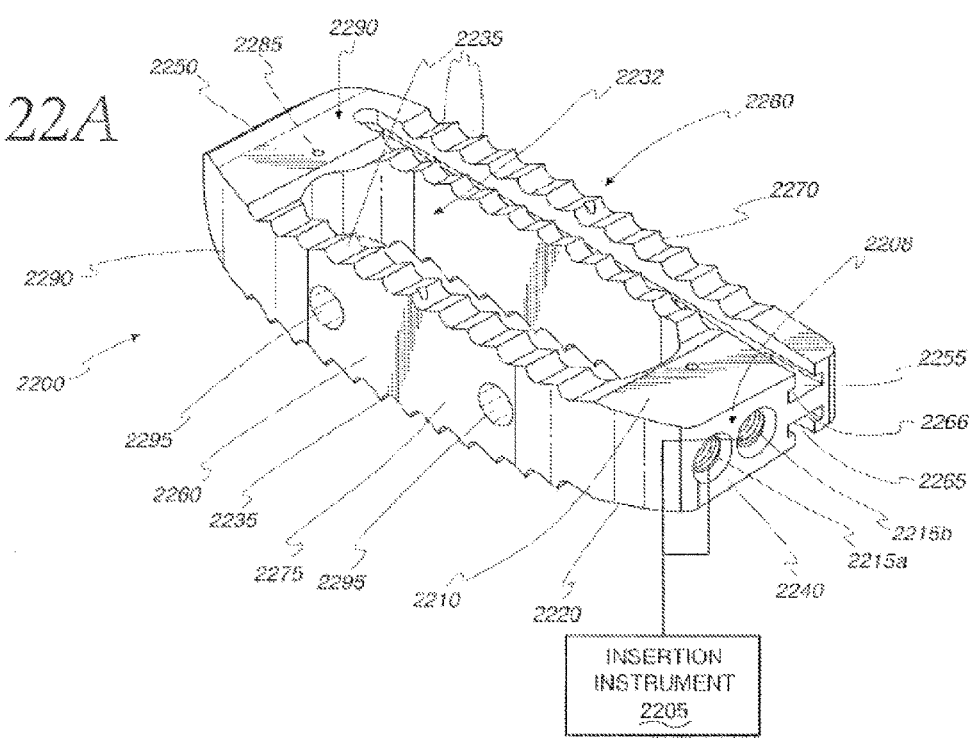

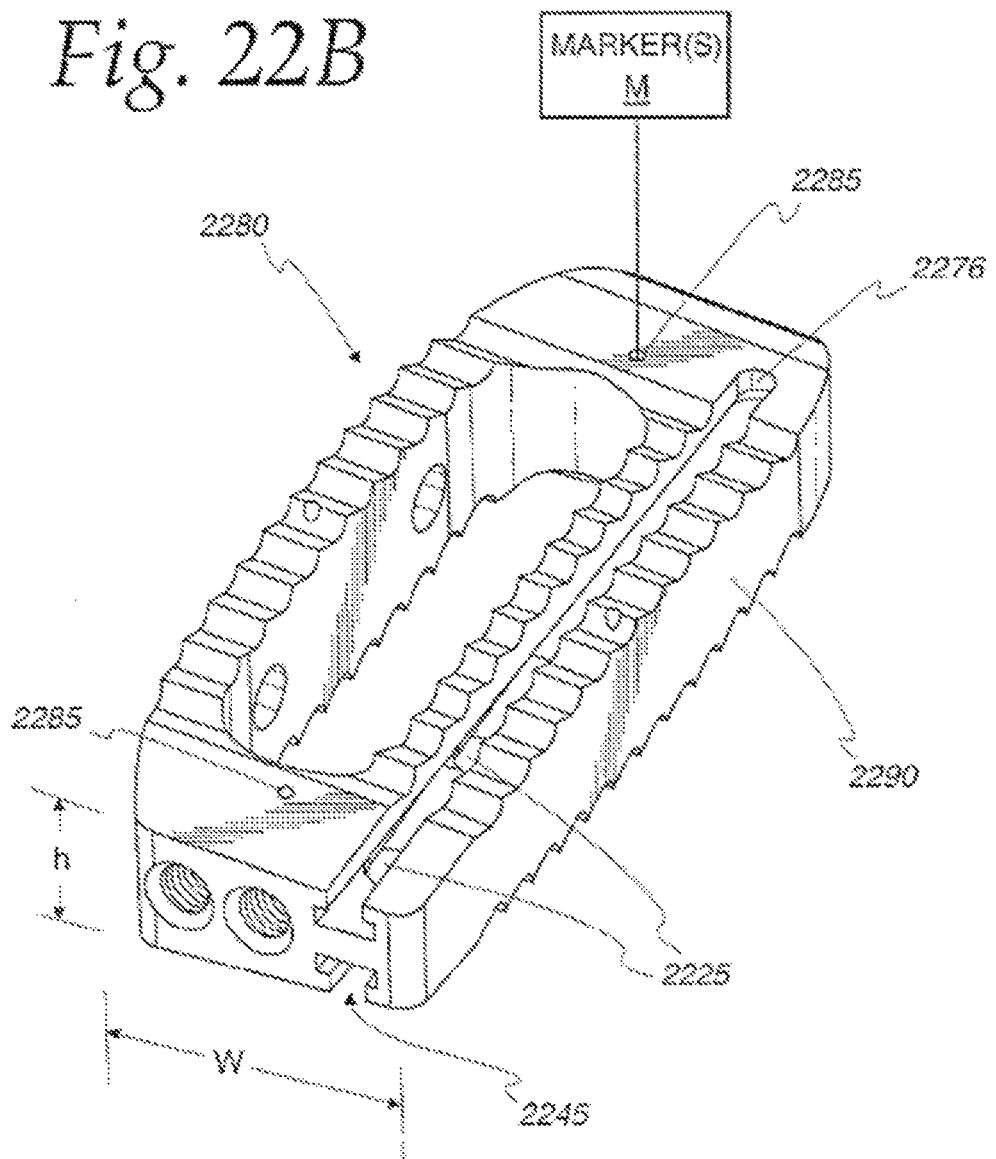

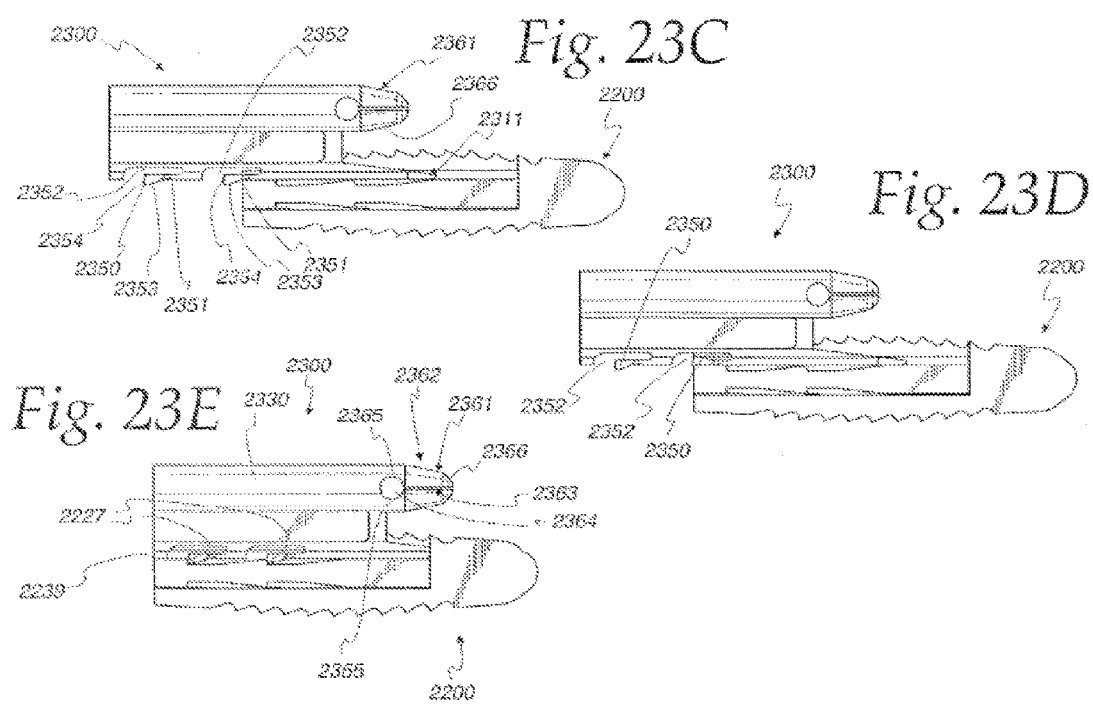

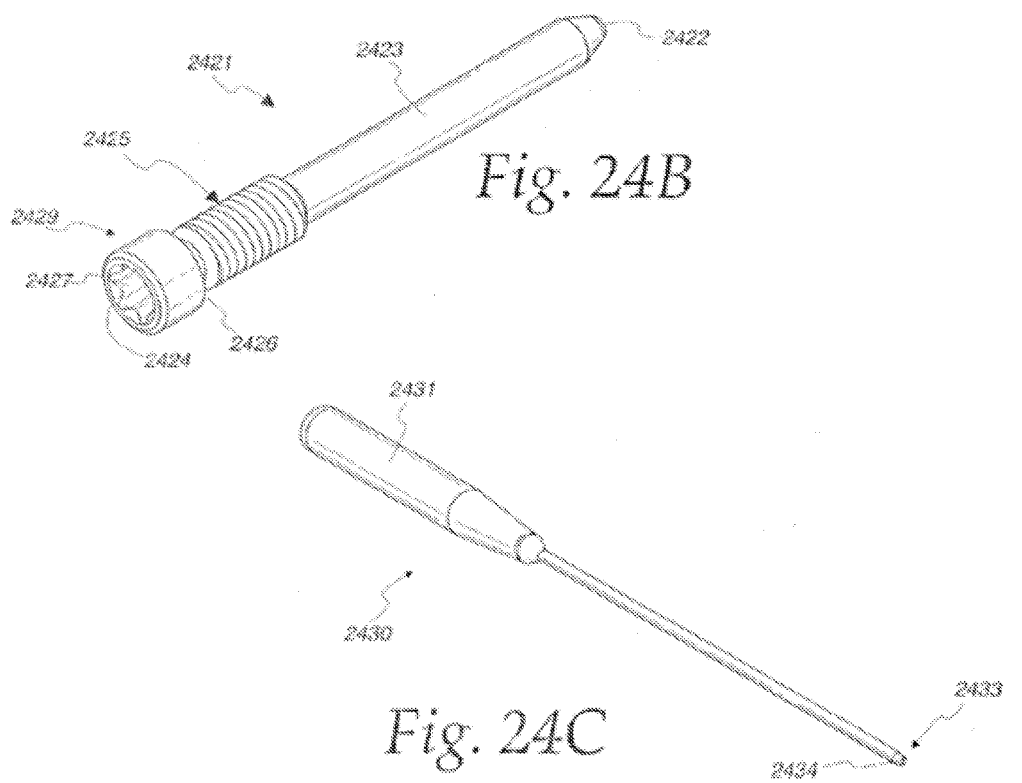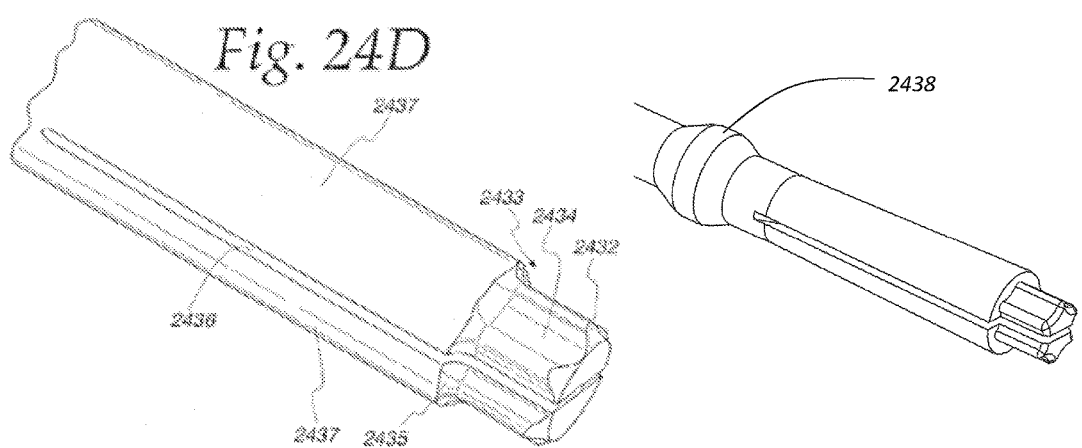

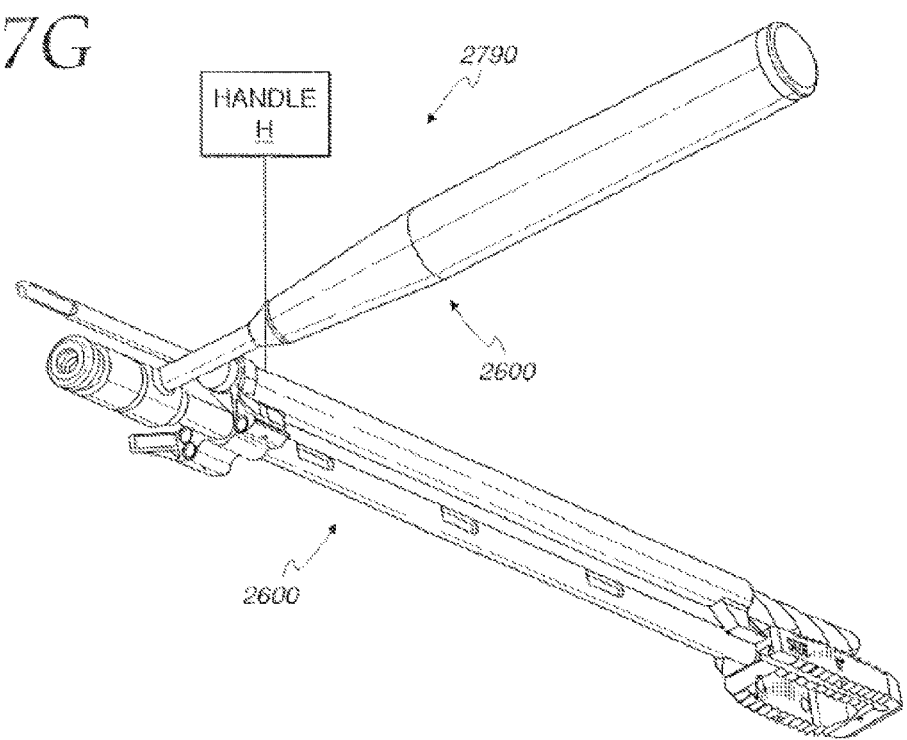

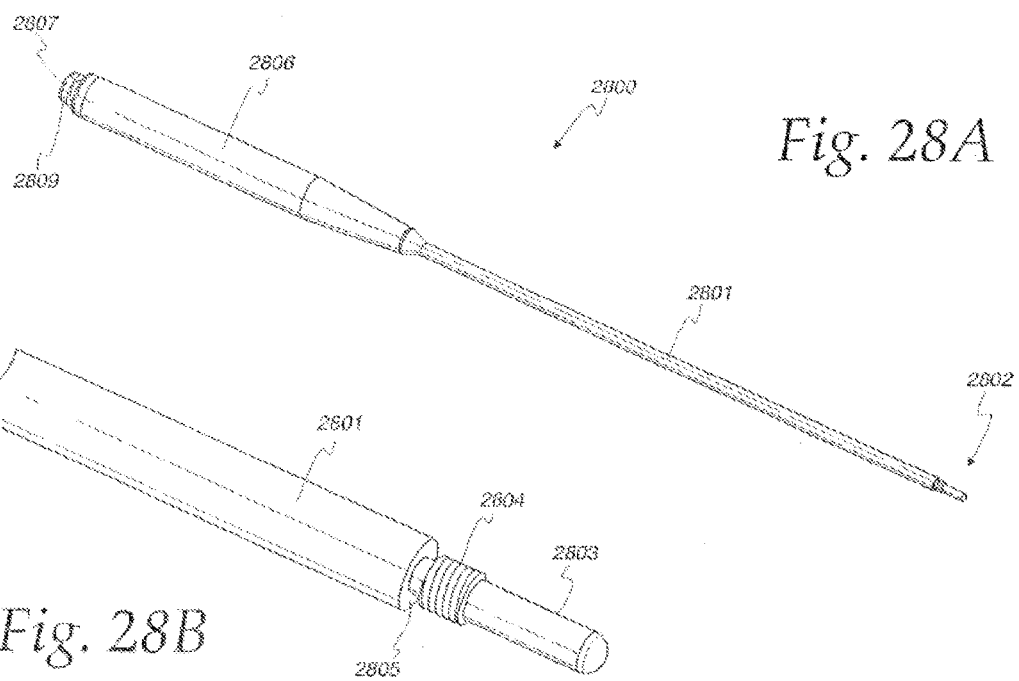

Stop faces of graft blocks abut verterbral bodies as nose of spacer is wedged into intervertebral space.

Graft blocks are forced proximally as spacer continues to advance.

APPARATUS AND METHOD FOR STABILIZING ADJACENT BONE PORTIONS

CROSS REFERENCE TO RELATED APPLICATIONS

This is a U.S. Divisional Patent Application of Continuation-In-Part patent application Ser. No. 14/453,520 filed Aug. 6, 2014 which claims priority to Continuation-In-Part patent application Ser. No. 13/347,526 filed Jan. 10, 2012, now U.S. Pat. No. 9,486,324, which claims priority to Continuation-In-Part application Ser. No. 12/692,503 filed on Jan. 22, 2010, now U.S. Pat. No. 8,157,865. Application Ser. No. 13/347,526 claims benefit of provisional application No. 61/431,235 filed on Jan. 10, 2011 and application Ser. No. 14/453,520 claims benefit of provisional patent application No. 61/862,671 filed Aug. 6, 2013, the entire disclosures of which are hereby incorporated by reference and relied upon.

BACKGROUND OF THE INVENTION

Field of the Invention

The present invention relates generally to the stabilization of adjacent bone portions, and more particularly to an apparatus for securing interbody spacers between the adjacent bone portions and related instruments. The invention is also directed to a method for stabilizing the adjacent bone portions.

Description of Related Art

Many different medical procedures are performed that require the stabilization of adjacent bone portions through the securing of an interbody spacer to the adjacent bone portions. Examples of these spacers are those known in the field as interbody cages, corpectomy cages, osteotomy wedges, joint spacers, bone void fillers, etc.

As one example, spacers are used to fuse joints. Spacers are also used to repair complex fractures where bone is missing and in bone regions where there are otherwise voids, as when a tumor and adjacent bone are removed. Spacers are also used in the performance of osteotomies by placing the spacers between adjacent bone portions to perform a wedging action, as to straighten a bone. This list is not exhaustive of the medical procedures that require the placement of a spacer between adjacent bone portions.

In each procedure, the spacer placed between the bone portions is required to be rigidly joined to the adjacent bone portions. A multitude of different apparatus have been devised for this purpose, with many requiring the insertion of screws. While screws are generally effective for this purpose, they are limited in the sense that they do not afford stability in all dimensions required to effect the optimal or desired rigidity.

Spacers are commonly used in spinal repair and reconstruction. The spine is a flexible column formed of a plurality of bones called vertebrae. The vertebrae are hollow and piled one upon the other, forming a strong hollow column for support of the cranium and trunk. The hollow core of the spine houses and protects the nerves of the spinal cord. The different vertebrae are connected to one another by means of articular processes and intervertebral, fibrocartilaginous bodies.

The intervertebral fibro-cartilages are also known as intervertebral disks and are made of a fibrous ring filled with pulpy material. The disks function as spinal shock absorbers and also cooperate with synovial joints to facilitate movement and maintain flexibility of the spine. When one or more disks degenerate through accident or disease, nerves passing near the affected area may be compressed and are consequently irritated. The result may be chronic and/or debilitating back pain. Various methods and apparatus have been designed to relieve such back pain, including spinal fusion using a suitable graft or interbody spacer using techniques such as Anterior Lumbar Interbody Fusion (ALIF), Posterior Lumbar Interbody Fusion (PLIF), or Transforaminal Lumbar Interbody Fusion (TLIF) surgical techniques. The implants used in these techniques, also commonly referred to as vertebral body replacement (VBR) devices, are placed in the interdiscal space between adjacent vertebrae of the spine.

Ideally, a fusion graft should stabilize the intervertebral space and become fused to adjacent vertebrae. Moreover, during the time it takes for fusion to occur, the graft should have sufficient structural integrity to withstand the stress of maintaining the space without substantially degrading or deforming and have sufficient stability to remain securely in place prior to actual bone ingrowth fusion.

One significant challenge to providing fusion graft stability (prior to actual bone ingrowth fusion) is preventing spinal extension during patient movement. Distraction of the vertebral space containing the fusion graft may cause the graft to shift or move, disrupting bone ingrowth fusion and causing pain.

Generally, existing spinal fusion technology has been limited or lacking in certain respects. Among the limitations of certain of these systems is the requirement that complicated steps be performed to effect their use. Others of these systems lack the optimal multidimensional stability, while others are less than desirable because they utilize components that project to externally of one or more of the bone portions between which the spacer is located.

The systems that rely upon the use of screws normally have such limitations. Generally these systems do not effectively allow compression forces to be generated between the spacers and adjacent bone portions. Further, while the screws stabilize the bone-spacer junction in one plane, that is normally flexion-extension, they do not control bending in planes orthogonal to the plane of the screw, that is normally side-to-side bending.

A further problem with existing systems is that parts typically are not locked and are thus prone to working loose. Screws, for example, may loosen over time in the absence of incorporating some structure that effectively prevents turning or lengthwise movement that results in partial or full separation from the bone portions and/or spacers that they penetrate.

The spacers and features of the spacer for joining it to the bone portions are typically inserted within surgical corridors offering limited access and vision. A further problem is that existing systems do not have instrumentation that is intuitive and well suited for performing the surgical procedure within this corridor. Instruments that are not intuitive make the surgery difficult and increases the potential for injury to the patient.

The medical field is constantly seeking system designs that might be efficiently and consistently installed and that, most significantly, will effect the desired fusion in a manner that will be safe and reliable for the patient.

BRIEF SUMMARY OF THE INVENTION

In one form, the invention is directed to a method for stabilizing first and second adjacent bone portions. The method includes the steps of: providing a spacer; providing a stabilizer, with the spacer and stabilizer configured to be movable guidingly, one relative to the other, between a pre-assembly relationship and an operative relationship; and placing the spacer and stabilizer into an operative relationship with the first and second adjacent bone portions by: a) placing the spacer between the first and second adjacent bone portions; b) directing the stabilizer into the first bone portion; and c) changing the spacer and stabilizer from their preassembly relationship into their operative relationship. As an incident of the spacer and stabilizer being changed from their pre-assembly relationship into the operative relationship with each other and the first and second bone portions, the spacer, stabilizer and first bone portion cooperate to cause the first bone portion and spacer to be urged towards each other.

In one form, the step of providing a stabilizer involves providing a stabilizer with a body having first and second spaced walls joined by a web. The first and second spaced walls respectively have first and second surfaces that face each other.

In one form, the method further includes the step of pre-forming a first channel in the first bone portion and the step of directing the stabilizer into the first bone portion involves moving the second wall guidingly in the first channel between a first position and a second position. The second wall is in the second position with the spacer and stabilizer in the operative relationship with the first and second adjacent bone portions.

In one form, the spacer has a first surface that faces a first surface on the first bone portion with the spacer between the first and second bone portions and the stabilizer web has a sharp leading edge. The step of directing the stabilizer into the first bone portion includes the step of causing the sharp leading edge on the web to cut through the first bone portion between the first channel and first surface on the first bone portion.

In one form, the step of providing a stabilizer involves providing a stabilizer having a length, with the second wall having a lengthwise axis. The second surface has a convex curvature, as seen in cross-section taken transversely to the length of the stabilizer, with a radius at or adjacent to the lengthwise axis of the second wall. The stabilizer further has a leading end and a nose with a tapered surface portion that is angled between the leading end and the second surface. The spacer is placed between the first and second bone portions before the stabilizer is directed into the first bone portion. As an incident of the stabilizer being changed from its first position into its second position, the tapered nose surface bears against the first bone portion and progressively wedges the first bone portion towards the spacer.

In one form, the first and second bone portions are adjacent first and second vertebrae. The spacer has oppositely facing first and second surfaces. The first vertebra has a first endplate with a first surface facing the first surface on the spacer. The first endplate has a first dimension parallel to the length of the stabilizer with the spacer and stabilizer in their operative relationship. The step of providing a stabilizer involves providing a stabilizer wherein the second surface on the stabilizer applies a force on the first bone portion over a majority of the first dimension of the first surface of the first endplate that urges the first endplate surface against the first spacer surface.

In one form, the step of placing the spacer and stabilizer into operative relationship with the first and second adjacent bone portions involves causing a part of the first bone portion and a part of the spacer to be compressively maintained between the first and second stabilizer surfaces.

In one form, the step of directing the stabilizer into the first bone portion involves advancing the stabilizer guidingly in a path in a first direction, The method further includes the step of reconfiguring the stabilizer, with the spacer and stabilizer in the operative relationship with the first and second adjacent bone portions, into a locked state to block movement of the stabilizer relative to the first bone portion oppositely to the first direction.

In one form, the stabilizer has a first tab and the step of reconfiguring the stabilizer from the first state into the locked state involves moving the first tab from a first position into a second position wherein the first tab bears against the first bone portion.

In one form, the step of providing a stabilizer involves providing a stabilizer with a movable spreader, and the step of reconfiguring the stabilizer involves moving the spreader from a first position into a second position as an incident of which the first tab is moved from its first position into its second position.

In one form, the step of providing a stabilizer involves providing a stabilizer that is turned about an axis relative to the second wall to change the spreader between its first and second positions.

In one form, the first tab has a hinge portion and the step of moving the tab involves moving the tab about the hinge portion from its first position into its second position.

In one form, the first tab has a live hinge and the step of moving the first tab involves moving the tab about the live hinge portion from its first position into its second position.

In one form, the step of providing a stabilizer involves providing a stabilizer with first and second movable tabs, and the step of reconfiguring the stabilizer from the first state into the locked state involves moving the first tab from a first position into a second position wherein the first tab bears against the first bone portion. The second tab defines the tapered nose surface portion.

In one form, the step of providing a stabilizer involves providing a stabilizer with a movable spreader, and the step of reconfiguring the stabilizer involves moving the spreader from a first position into a second position, as an incident of which the first tab is moved from its first position into its second position and the second tab is moved from a first position into a second position.

In one form, the step of moving the spreader involves moving the spreader from its first position into its second position and against each of the first and second tabs to change each of the first and second tabs from its first position into its second position.

In one form, the step of providing a spacer involves providing a spacer with a channel and the step of changing the spacer and stabilizer from their pre-assembly relationship into their operative relationship involves moving a part of the stabilizer guidingly within the channel.

In one form, the steps of providing a spacer and stabilizer involve providing a spacer and stabilizer each with a blocking surface, which blocking surfaces abut to block the spacer and stabilizer from moving out of their operative relationship.

In one form, the steps of providing a spacer and stabilizer involve providing a spacer and stabilizer each with a blocking surface, which blocking surfaces are brought into confronting relationship as an incident of the spacer and stabilizer being changed from their pre-assembly relationship into their operative relationship.

In one form, the method further includes the step of reconfiguring one of the spacer and stabilizer with the spacer and stabilizer in their operative relationship to thereby place the blocking surfaces on each of the spacer and stabilizer in confronting relationship.

In one form, the steps of providing a spacer and stabilizer involve providing a deflectable tab defining the blocking surface on one of the spacer and stabilizer which deflects in one direction as the spacer and stabilizer are changed from their pre-assembly relationship into their operative relationship and is moved oppositely to the one direction under a restoring force to place the blocking surface on the one of the spacer and stabilizer into confronting relationship with the blocking surface on the other of the spacer and stabilizer as an incident of the spacer and stabilizer realizing the operative relationship.

In one form, the step of providing a stabilizer involves providing a stabilizer wherein the deflectable tab is on the first wall of the stabilizer.

In one form, the step of providing a stabilizer involves providing a stabilizer wherein the first wall and web on the stabilizer cooperatively define a "T"-shaped portion.

In one form, the step of providing a spacer involves providing a spacer with a "T"-shaped channel that is complementary to the "T"-shaped portion of the stabilizer, and the step of changing the spacer and stabilizer from their pre-assembly relationship into their operative relationship involves moving the "T"-shaped portion of the stabilizer guidingly within the "T"-shaped channel.

In one form, the step of providing a stabilizer involves providing a stabilizer with the second surface on the second wall having a convexly curved shape.

In one form, the step of providing a stabilizer involves providing a stabilizer with the second wall on the stabilizer having a cylindrical shape.

In one form, the step of providing a stabilizer involves providing a stabilizer wherein the first wall and web are substantially flat and cooperatively define a "T"-shaped portion. The second surface on the second wall has a convexly curved shape.

In one form, the method further involves the step of reconfiguring the stabilizer from a first state, with the spacer and stabilizer in the operative relationship with the first and second adjacent bone portions, into a locked state by moving a part of the stabilizer forcibly against the first bone portion.

In one form, the stabilizer is directed into the bone portion before the spacer and stabilizer are changed from their pre-assembly relationship into their operative relationship.

In one form, the method further includes the step of providing a second stabilizer and connecting the second stabilizer to each of the spacer and the second bone portion.

In one form, the method further includes the step of reconfiguring the stabilizer after it has been changed into the locked state back into the first state and thereafter separating the stabilizer and spacer from the first and second bone portions.

In one form, the method further includes the steps of providing a guide structure on the spacer and using the guide structure to pre-form the first channel in the first bone portion.

In one form, the step of moving the part of the stabilizer forcibly against the first bone portion involves the step of moving the part of the stabilizer forcibly against the first bone portion in a manner so as to thereby urge the first bone portion and spacer against each other.

In one form, the step of providing a spacer involves providing a spacer with first and second spaced bores. The method further includes the step of providing an auxiliary tool that is used in conjunction with the spacer by connecting the auxiliary tool using at least one of the first and second bores.

In one form, the method further includes the step of connecting the auxiliary tool to the spacer by placing first and second connectors on the auxiliary tool one each into the first and second bores.

In one form, the method further includes the step of connecting the auxiliary tool to the spacer by using either one, but only one, of the first and second bores.

In one form, the steps of providing a spacer and stabilizer include providing first and second deflectable tabs each defining a blocking surface on at least one of the spacer and stabilizer that each deflects in a direction as the spacer and stabilizer are changed from the preassembly relationship into the operative relationship, and are moved oppositely to their deflecting direction under restoring forces to place each of the blocking surfaces separately into confronting relationship with a blocking surface on the spacer or stabilizer as an incident of the spacer and stabilizer realizing the operative relationship.

In one form, the step of placing a spacer and stabilizer in operative relationship with the first and second bone portions involves moving the spacer and stabilizer substantially only in a single plane and parallel to a single line.

In one form, the step of preparing the spacer with graft includes covering bone graft in a graft aperture within the spacer to prevent unintentional fallout of the bone graft while packing bone graft in the spacer aperture and during insertion of the spacer between bone portions.

In one form, the step of preparing the spacer with graft includes inserting a graft block into an anchor portion of the spacer wherein a paddle extending from the graft block covers a graft aperture on the spacer to prevent unintentional fallout of bone graft packed within the graft aperture.

In one form, the step of preparing the spacer with graft includes inserting a plurality of graft blocks into one or more anchor portions of the spacer wherein a plurality of paddles on the graft blocks cause the bone graft to be fully encapsulate the bone graft within the graft aperture.

In one form, during the step of inserting the spacer between the bone portions, the graft blocks are retracted therein placing the spacer's graft aperture in direct communication with the bone portions.

In one form, the step of inserting the spacer between the bone portions includes abutting a stop face on the graft block against the bone portions preventing further advancement of the graft block.

In one form, the step of inserting the spacer between the bone portions includes the step of one or more graft blocks retracted from the incision site.

In one form, the step of inserting a drill guide includes joining the tip of a drill guide with an anchor portion of a spacer and advancing the drill guide to a predetermined position against a bone portion.

In one form, the step of creating a hole within a bone portion includes advancing a bone drill down a drill guide and into the bone portion.

In one form, the step of inserting a stabilizer includes releasably securing a stabilizer inserter to a proximal end of a stabilizer.

In one form, the step of inserting a stabilizer includes aligning a base wall nose within a spacer channel or spacer inserter tool channel and advancing the stabilizer into the spacer by applying directed force to a stabilizer inserter.

In one form, the step of inserting a stabilizer includes advancing the stabilizer until the stabilizer reaches a predetermined position with respect to the spacer and locking the stabilizer in place. In one form, the step of inserting a stabilizer includes removing a stabilizer inserter from the incision site.

In one form, the step of placing the stabilizer in an operative relationship includes inserting the tip of a drill guide into a spacer channel or spacer inserter channel and advancing the drill guide to the stabilizer.

In one form, the step of placing the stabilizer in an operative relationship includes releasably securing a spreader driver tool to a spreader and advancing the spreader into the stabilizer.

In one form, the invention is directed to the combination of a stabilizer and spacer. The spacer can be placed between first and second adjacent bone portions and has oppositely facing surfaces. The stabilizer is movable guidingly relative to the spacer in a first path in a first direction: a) from a position wherein the stabilizer is in a pre-assembly relationship with the spacer; and b) into a position wherein the stabilizer is in an operative relationship with the spacer. The stabilizer is capable of being directed in the first direction while being moved in the first path relative to the spacer into one of the first and second bone portions so as to urge a surface of the one bone portion forcibly against one of the spacer surfaces with the spacer and stabilizer in operative relationship with each other and the first and second adjacent bone portions. The stabilizer has a body including first and second spaced walls joined by a web. The first and second spaced walls respectively have first and second surfaces that face each other. The second wall has a leading end and a surface portion that is angled with respect to the first path to produce a wedging action against the one bone portion as the stabilizer is advanced in the first direction in the first path into the one bone portion. The wedging action causes a part of the one bone portion and a part of the spacer to be urged towards each other as the spacer and stabilizer are moved into operative relationship with each other and the first and second adjacent bone portions.

In one form, the stabilizer has a length and a lengthwise axis. The first path is substantially straight along a first line and the second surface has a convex curvature as seen in cross-section taken transverse to the length of the stabilizer with a radius that is centered on a line parallel to the lengthwise axis of the stabilizer.

In one form, the stabilizer has a nose defining the tapered surface portion that is angled with respect to the central axis of the stabilizer.

In one form, the second wall has a cylindrical shape and the nose defines the surface portion that tapers between a leading end of the second wall and the second surface.

In one form, the nose is split to define separate tabs. One of the tabs is selectively movable so that the one tab forcibly engages the one bone portion to change the stabilizer from a first state into a locked state to prevent movement of the stabilizer relative to the one bone portion with the spacer and stabilizer in operative relationship with each other and the first and second adjacent bone portions.

In one form, the combination further includes a spreader that is selectively movable relative to the stabilizer to thereby change the stabilizer from the first state into the locked state.

In one form, the first wall and web are substantially flat and cooperatively define a "T"-shaped portion. The spacer has a "T"-shaped channel that cooperates with the "T"-shaped portion of the stabilizer to guide relative movement between the pre-assembly and operative relationships.

In one form, the second wall has a substantially cylindrical shape that defines the second surface.

In one form, the first surface resides in a first plane and the cylindrical shape has a central axis. The first plane and central axis of the cylindrical shape are substantially parallel.

In one form, the first surface resides in a first plane and the cylindrical shape has a central axis and the first plane and central axis of the cylindrical shape are at an angle with respect to each other.

In one form, the spacer has a channel to guide the stabilizer as the spacer and stabilizer are relatively moved between their pre-assembly and operative relationships. The spacer has a stop portion that abuts the stabilizer moving in the first direction so that the spacer and stabilizer can be consistently placed in their operative relationship.

In one form, the spacer and stabilizer have cooperating blocking surfaces that abut to block the spacer and stabilizer from moving out of their operative relationship.

In one form, the blocking surfaces contact each other as an incident of the spacer and stabilizer realizing the assembly relationship.

In one form, one of the blocking surfaces is on a movable tab on one of the spacer and stabilizer. The movable tab is deflected in one direction as the spacer and stabilizer are moved from their pre-assembly relationship toward their operative relationship and moves under a restoring force oppositely to the one direction upon the operative relationship between the spacer and stabilizer being realized.

In one form, the second wall has a cylindrical shape with a central axis. The combination further includes a drill guide on the spacer and a drill that is movable controllably along the drill guide parallel to a central axis of the drill. The spacer has a third surface to which the first surface of the stabilizer abuts with the spacer and stabilizer in their operative relationship. A first distance between the central axis of the drill on the drill guide and the third surface is greater than a second distance between the central axis of the second wall and the first surface.

In one form, the first distance is greater than the second distance by on the order of 0.5 mm.

In one form an auxiliary tool is a cage or spacer inserter tool.

In one form, the spacer inserter tool comprises a longitudinal guide to direct the stabilizer through an incision and into an anchor portion of the spacer. In one form the longitudinal guide directs axillary tools into or in alignment with an anchor portion of the spacer.

In one form, the longitudinal guide comprises opposing channels.

In one form, the opposing channels are in the form of T-shaped slots.

In one form, the body of the spacer inserter tool comprises a shaft aperture.

In one form, the spacer inserter tool houses a locking shaft for securing the spacer to the spacer inserter tool.

In one form, the locking shaft resides in an shaft aperture having an elongate axis formed within the spacer inserter tool.

In one form, the elongate axis of the shaft aperture formed within the spacer inserter tool for housing the locking shaft is parallel to an elongate axis of the longitudinal guide.

In one form, the spacer inserter tool comprises a handle portion for grasping by the user for controlling the spacer inserter tool.

In one form, an elongate axis of the handle portion is generally perpendicular to an elongate axis of a guide bar body portion of the spacer inserter tool.

In one form, the locking shaft includes an impact fitting. The impact fitting may be used to tap the spacer inserter and spacer into the intervertebral space.

In one form, an auxiliary tool is a graft blocker for containing bone graft or bone substitute within the spacer during insertion of the spacer.

In one form the graft blocker comprises a paddle portion for covering an opening within the spacer where graft is contained during implant insertion.

In one form, the graft blocker comprises one or more channel locks for guiding and sliding engagement of the graft blocker with the longitudinal guide of the spacer inserter tool and for sliding engagement with an aligned anchor portion within the spacer.

In one form, the graft blocker includes an arm for the user to control the graft blocker from outside the incision while the spacer is inserted to a predetermined position between the bone portions.

In one form, the graft blocker includes a stop face that abuts the bone portions and causes retraction of the graft blocker as the spacer is inserted between the bone portions.

In one form, the auxiliary instruments comprise cleaning or access apertures for cleaning the instruments.

In one form, the auxiliary instrument is a drill guide for guiding a drill to predetermined location within a bone portion.

In one form, the drill guide includes a drill guide cylinder for guiding a drill within the drill guide.

In one form, the drill guide comprises a drill guide tip that is insertable into an anchor portion of a spacer to ease insertion of the drill guide into the spacer.

In one form, the drill guide includes a handle portion for the user to control position of the drill guide within the incision.

In one form, the drill guide includes a base wall and a web wall for aligning the drill guide within the longitudinal guide of the spacer inserter tool or within the anchor portion of the spacer.

In one form, the drill guide includes a drill guide stop to align the relative depth of drill guide with the spacer inserter tool.

BRIEF DESCRIPTION OF THE SEVERAL VIEWS OF THE DRAWINGS

These and other features and advantages of the present invention will become more readily appreciated when considered in connection with the following detailed description and appended drawings, wherein:

FIG. 1 is a schematic, perspective view of one embodiment of an interbody spacer showing a superior surface and an anterior surface thereof;

FIG. 2 is a perspective view of one embodiment of a stabilizer;

FIG. 3 is an end view of the stabilizer of FIG. 2;

FIG. 4 is an end plan view of the spacer of FIG. 1 inserted between two vertebrae with the stabilizers of FIG. 2 anchoring the spacer to the vertebrae;

FIG. 5A is a top perspective view of another embodiment of a stabilizer;

FIG. 5B is an end view of the stabilizer of FIG. 5A;

FIGS. 8A-M depict various conventional embodiments of interbody spacers;

FIG. 9 is a schematic, perspective view of another embodiment of an interbody spacer showing a superior surface and an anterior surface thereof;

FIG. 10 is an end view of yet another embodiment of a stabilizer;

FIG. 11 is a perspective view of the stabilizer of FIG. 10;

FIG. 12 is an end view of the spacer of FIG. 9 with the two stabilizers according to FIG. 10 inserted into the spacer;

FIG. 16 is a view as in FIG. 15 wherein a different configuration of stabilizer and spacer are used to perform as described for the corresponding components in FIG. 16;

FIG. 17 is a view as in FIGS. 15 and 16 showing a further modified form of stabilizer with one form of locking assembly to maintain the stabilizer in place;

FIG. 18 is an enlarged, plan view of a modified form of locking assembly on a stabilizer and spacer and with locking assembly components on the stabilizer configured as they would be with the locking assembly in a locked state;

FIG. 22A is a perspective view of another embodiment of an interbody spacer showing an anterior, proximal, and superior surface thereof;

FIG. 22B is a perspective view of an embodiment of an interbody spacer illustrating a posterior, proximal, and superior surface thereof;

FIG. 23C is a side view of a stabilizer as it begins to insert into the channel of a spacer, with a portion of the spacer resected for viewing purposes;

FIG. 23D is a side view of a stabilizer with self retaining clips deflecting into deflection pockets as the stabilizer is further translated into the spacer, with a portion of the spacer resected for viewing purposes;

FIG. 23E is a side view of a stabilizer fully docked within a spacer and self retaining clips fully seated within stop pocket, with a portion of the spacer resected for viewing purposes;

FIG. 24B is a perspective view of a spreader used to deploy the tabs of the stabilizer;

FIG. 24C is a perspective view of a spreader driver tool;

FIG. 24D is a close-up perspective view of a drive head of the spreader driver tool;

FIG. 27G is a perspective view of a drill-guide spacer inserter assembly and drill secured to the spacer;

FIG. 28A is a perspective view of a stabilizer inserter; and

FIG. 28B is a close-up perspective view of the stabilizer inserter illustrated in FIG. 28A.

DETAILED DESCRIPTION OF SELECTED EMBODIMENTS OF THE INVENTION

Embodiments of the invention will now be described with reference to the Figures. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

FIG. 1 illustrates schematically one embodiment of an interbody spacer 100. The spacer 100 can be used between any adjacent bone portions, such as members at a joint, in a void between such joint portions as might be developed by a fracture, through a procedure that removes bone as with a tumor, etc. While the invention is contemplated for use with virtually any adjacent bone portions between which a spacer is required, the initial disclosure herein will be directed towards spinal procedures wherein the spacer 100 is placed between adjacent vertebrae/joint members that make up a subset of the more generically referenced bone portions.

Figure 8A:
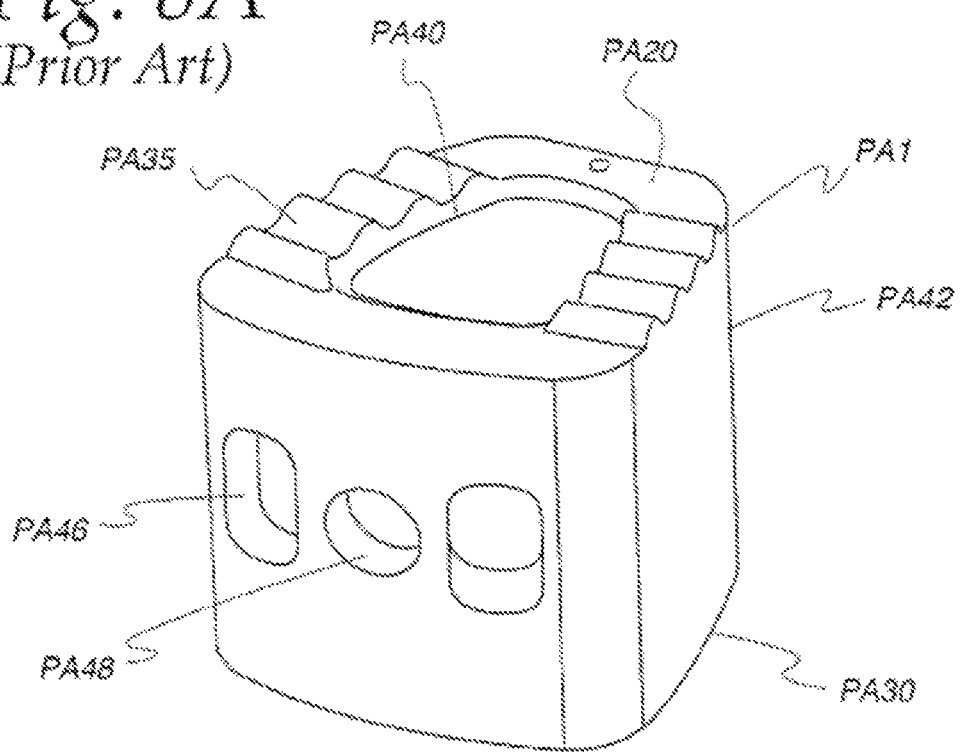
Figure 8B:
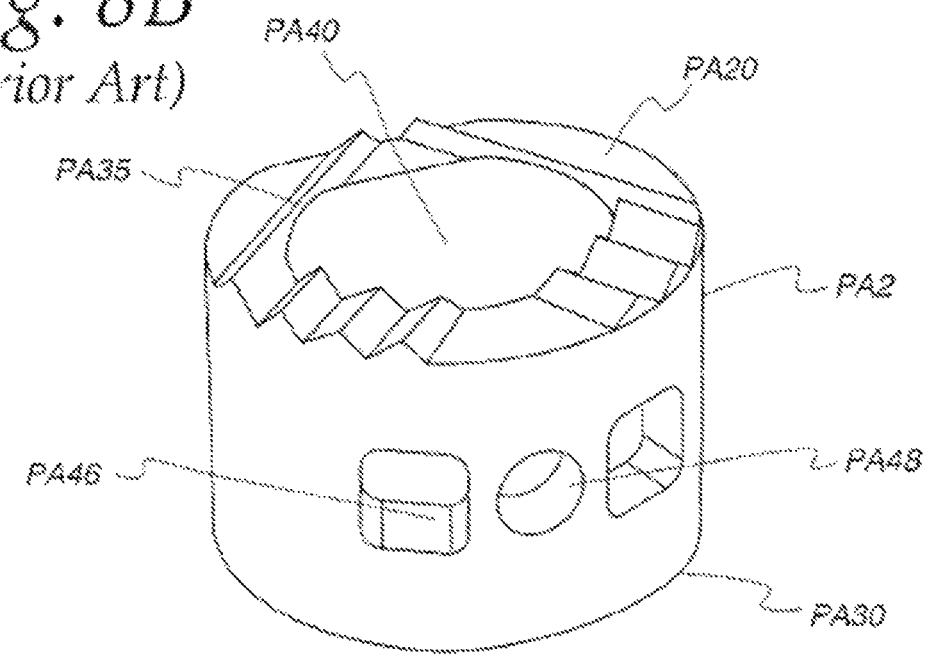
Figure 8G:
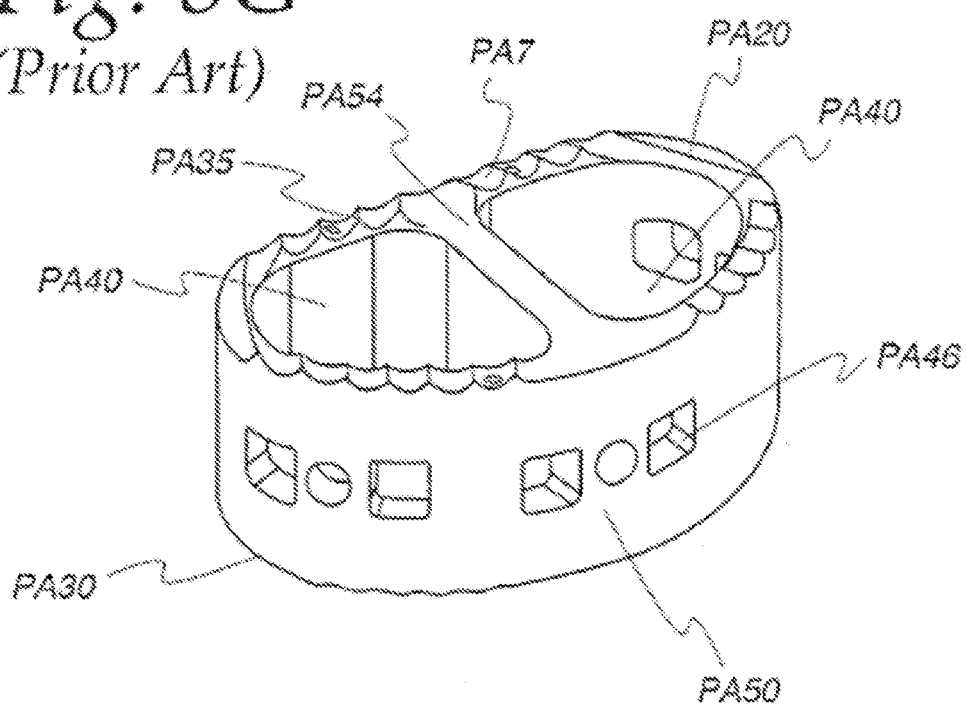
Figure 8H:
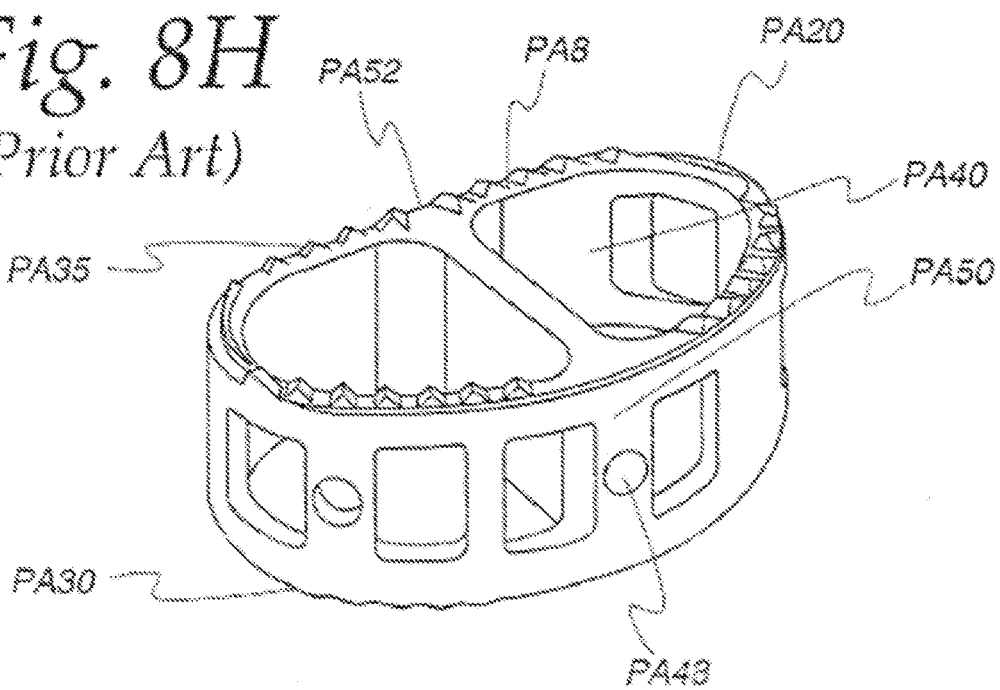
Figure 8I:
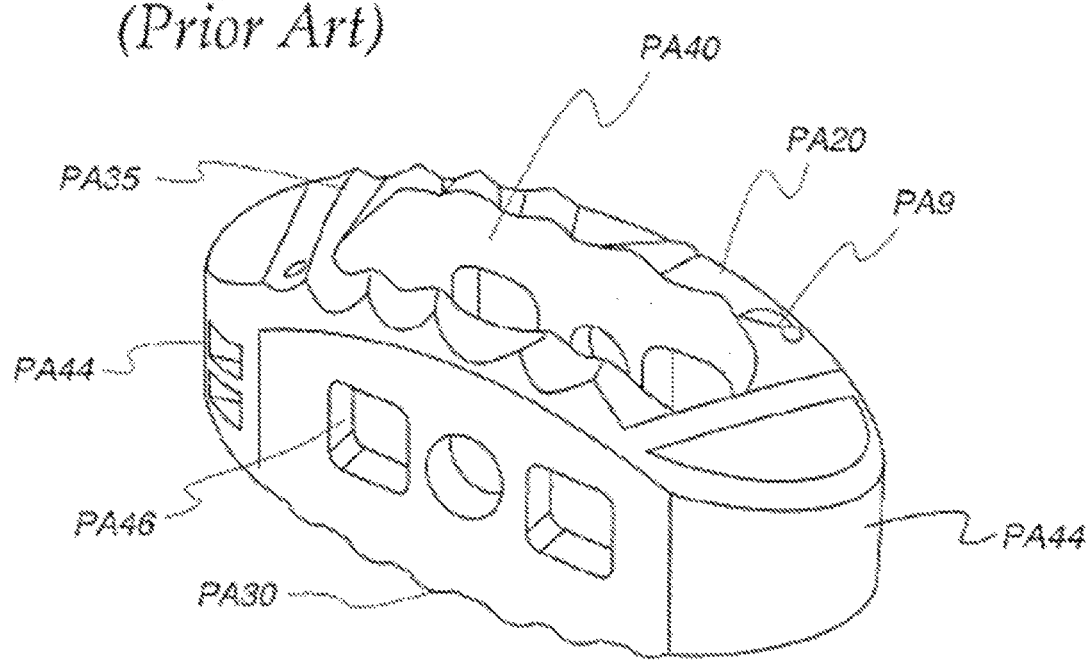
Figure 8J:
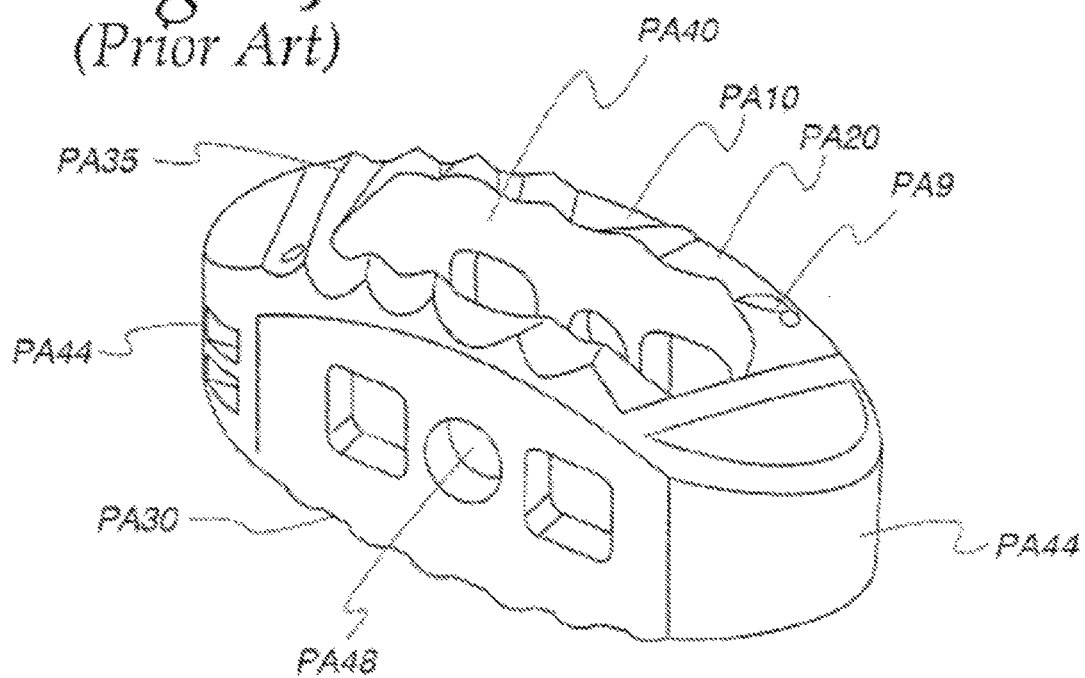
Figure 8K:
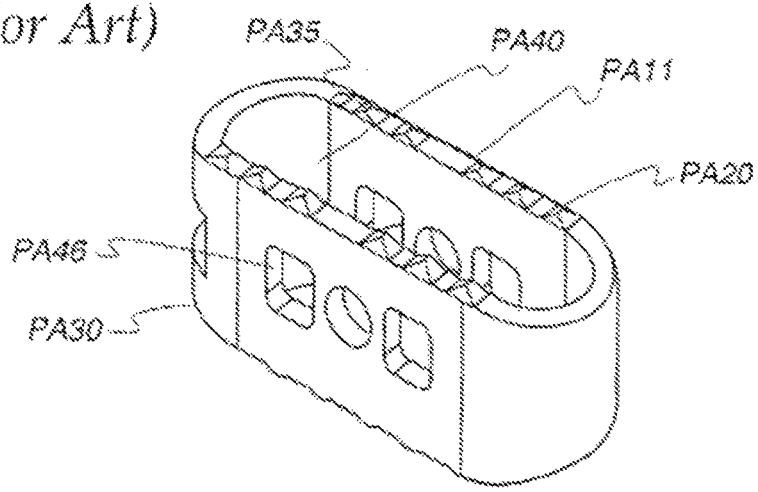
Figure 8L:
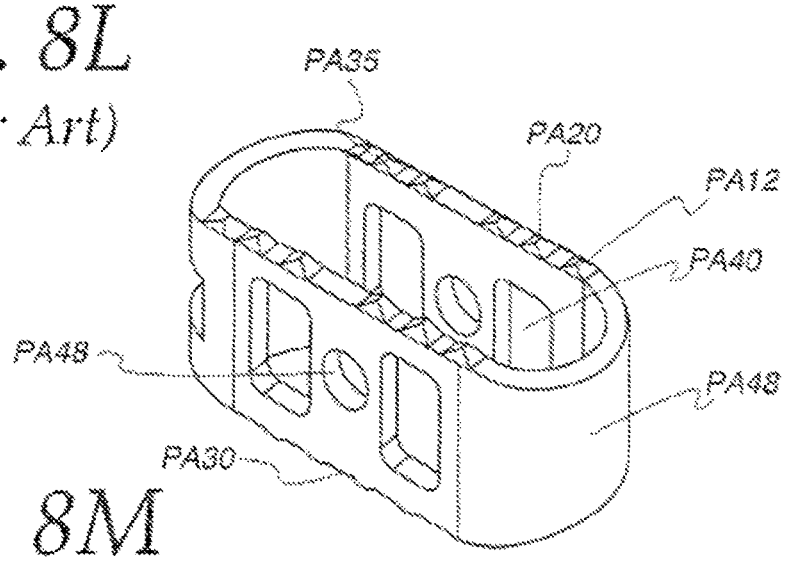
Figure 8M:
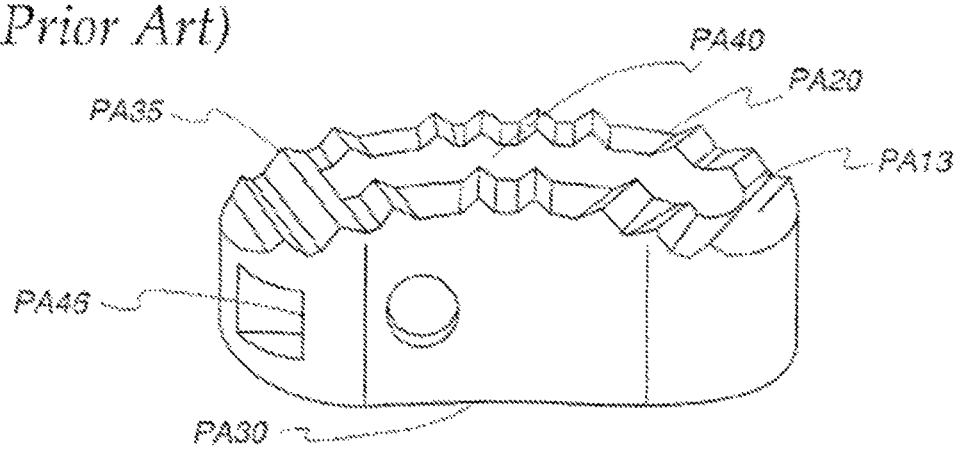

Embodiments of the invention can be incorporated in any number of interbody or vertebral body replacement devices, including for example, the devices shown in FIGS. 8A-8M. All of the interbody spacer devices shown in FIGS. 8A-8M are commercially available from Alphatec Spine™, Inc. (See website at: http://www.alphatecspine.com/products/interbody.asp). FIGS. 8A and 8B depict top perspective views of two configurations PA1, PA2 of the "Novel Cervical Interbody System" for use in an anterior cervical fusion procedure. FIGS. 8C-8F show top perspective views of four different configurations PA3, PA4, PA5, PA6 of the "Novel CP Vertebral Body Replacement System" for use in the thoracolumar spine (T1-L5). FIGS. 8G and 8H illustrate two "Novel VC Spinal Spacers" PA7, PA8 for use in Anterior Lumbar Interbody Fusion (ALIF), made of PEEK or titanium. FIGS. 8I and 8J depict two "Novel SD" interbody spacer devices PA9, PA10 made of PEEK or titanium, for use in a Posterior Lumbar Interbody Fusion (PLIF). FIGS. 8K and 8L show two "Novel LCC Spacer" devices PA11, PA12 made of PEEK and titanium, for use in a Posterior Lumbar Interbody Fusion (PLIF). FIG. 8M illustrates a "Novel TL Spacer" device PA13 for use in a Transforaminal Lumbar Interbody Fusion (TLIF).

The spacer 100 is used in spinal fusion surgeries including ALIF, PLIF and TLIF procedures, wherein two or more vertebrae are joined or fused together for the treatment of spinal disorders such as spondylolisthesis, scoliosis, severe disc degeneration, or spinal fractures. The embodiments below are described primarily in the context of an ALIF procedure, though other spinal implants and procedures are also contemplated.

The spacer 100, shown schematically in FIG. 1 and contemplated to have the shapes of any of the conventional spacers PA1-PA13, described above, or any other suitable shape, includes first and second opposite surfaces 120 and 130 respectively configured to engage superiorly and inferiorly the end plates of adjacent vertebrae. As shown for the spacers in FIGS. 8A-8M, these corresponding surfaces PA20 and PA30 may have ridges, bumps or other protrusions PA35 to enhance engagement with the vertebral endplates. As also shown in FIGS. 8A-8M, these surfaces PA20 may define openings PA40 (not shown in FIG. 1) to allow for fusion through the openings.

In the embodiment shown in FIG. 1, the first and second surfaces 120 and 130 are substantially flat and parallel. However, in other embodiments, the first and second surfaces can be angled relative to each other and may be non-flat, so as to better support adjacent vertebral bodies in a more natural spinal alignment configuration. For example, the first and second opposite surfaces, PA20 and PA30 of the interbody spacer shown in FIG. 8A, are slightly angled toward each other in the direction of the posterior surface PA42. Additionally, the first and second opposite surfaces, PA20 and PA30 of the interbody spacers shown in FIGS. 8I and 8J, are tapered toward each other toward the ends PA44 of the interbody spacers.

The spacer 100 has a proximal face 140 and a distal face 150, the proximal face 140 corresponding to the end that engages a delivery tool, such as with grooves or indentations PA46 or a threaded opening PA48 as shown in FIGS. 8A-8M. For an ALIF procedure, the proximal face 140 corresponds to the anterior face of the spacer (such as the convex surface PA50 in FIGS. 8G and 8H), and the distal face 150 corresponds to the posterior face of the spacer (such as the flat surface PA52 in FIG. 8H).

As illustrated in FIG. 1, the spacer 100 has three channels 155 for receiving suitable complementary stabilizers (discussed in further detail below), although it is to be understood that in other embodiments the spacer can have only one channel and in yet other embodiments, the space can have any number of channels.

The channels 155 interface with the first and second surfaces 120 and 130 of the spacer 100, as well as with at least the proximal surface 140 of the spacer 100. The channels 155 shown in FIG. 1 are shown extending through the body of the spacer 100, and interfacing with the distal surface 150 of the spacer 100. However, in other embodiments, the channels do not extend all the way through the spacer body to interface with the distal surface of the spacer and in other embodiments the channels 155 can interface with side surfaces 160 and 170. The channels 155 are preferably pre-cut into the spacer body 100 before insertion into the vertebral space during surgery. Where the spacer 100 has openings in the surfaces 120 and 130, the channels 155 may extend through solid portions of the spacer between the openings (such as through the intermediate bar PA54 shown in FIG. 8G, or may be interrupted by the openings PA40 so that the channels are provided on opposite sides of the openings PA40).

The interbody spacer 100 can be made of a rigid and durable biocompatible material such as titanium, titanium alloy, stainless steel iron steel and compositions thereof. Additionally, or alternatively, non-metal biocompatible materials such as cadaveric bone, polymers, elastomers, resins, ceramics and composites thereof can be employed. In a preferred embodiment, the interbody spacer is made of Polyetheretherketone (PEEK).

FIGS. 2 and 3 illustrate one embodiment of a stabilizer 200 suitable for use with the spacer 100 of FIG. 1, where FIG. 3 is an end view of the stabilizer of FIG. 2. The stabilizer 200 is configured to be partially received within the channels 155 of the spacer 100, with a portion extending out of the channel away from the surface 120 or 130 into the adjacent vertebral body. The stabilizer 200 is preferably thin enough to slice through bone, yet strong enough to hold onto the bone and stabilize the spacer 100 after insertion.

The stabilizer 200 as illustrated has three plates/walls 240, 250 and 260 attached together and configured in a "Z" shape as seen in FIG. 2. The stabilizer 200 can also be formed from a single plate which is bent to form the "Z" shape seen in FIG. 2. The stabilizer 200 is preferably made of titanium. However, it can also be made of any suitable material including, but not limited to: polycarbonate, urethane and PEEK. The stabilizer 200 preferably has sharp edges 264 and 266 which are thin and strong enough to slice through vertebral bone when a sufficient force is applied to the anterior surface 270 of the stabilizer 200. The stabilizer translates along a line (L in FIG. 2) under the applied force to be pressed into the bone portion to which it is aligned for this and other embodiments herein. The sharp edges 264, 266 may be at both ends so that the stabilizer can be inserted with either end thereof in a leading direction. The stabilizer 200 can also have self-retaining clips 272 attached to it to help keep the stabilizer attached to the spacer after insertion, as will be discussed in further detail below.

FIG. 4 shows the spacer 100 operably implanted within a spine 402 from the anterior side of the spine. The spine 402 includes bone portions/vertebrae 410, 420. The spine 402 also includes a diseased/damaged disk 430 that has been partially removed and replaced with the spacer 100.

During operation, the diseased/damaged disk 430 is partially or completely removed and preferably replaced with the spacer 100 with the proximal surface 140 of said spacer 100 facing anteriorly. Stabilizers 200 are then lined up with the channels 155 of the spacer 100 and driven by translational movement into the vertebral bodies 410, 420 by applying sufficient force to the stabilizers 200. The stabilizers 200 are simultaneously driven into the vertebral bones 410, 420 and received into their respective channels 155. However, it is to be understood that in some embodiments, stabilizers 200 can be inserted into the vertebral bone before spacer 100 is inserted.

As mentioned previously, the stabilizer 200 can further include self-retaining clips 272 (see FIG. 2) to fixedly attach the stabilizers 200 to the spacer 100 after insertion. The selfretaining clips 272 of FIG. 2 are attached to the stabilizer 200 and curve outward. The selfretaining clips 272 are made of a resilient material which allows them to retract during insertion. Once the stabilizers are inserted, the self-retaining clips 272 expand and push against the inner wall of the channel 155, resisting withdrawal. The inner walls of the channels 155 can be made rough or with notches to further aid the self-retaining clips 272 in resisting withdrawal.

It will be appreciated that the stabilizer 200 can have a variety of shapes and that the spacer 100 can be configured with complementary channels shaped to receive the stabilizer 200.

FIGS. 5A and 5B illustrate an alternative embodiment of a stabilizer 500 suitable for use with a spacer (not shown), having channels shaped to receive the stabilizer 500. FIG. 5A is a top perspective view of the stabilizer and FIG. 5B is an end view of the stabilizer of FIG. 5A. As illustrated, the stabilizer 500 has a substantially sinusoidal configuration. While not illustrated, the spacer for use with the stabilizer 500 has a complementary channel having a substantially sinusoidal shape configured to receive the stabilizer 500. The complementary channel can be oriented perpendicular to the upper and lower surfaces of the spacer, or in any other orientation which would allow the stabilizer 500 to fixedly attach the spacer to an adjacent vertebral body.

FIGS. 6A-6J show various end views of alternative embodiments of differently shaped stabilizers, by way of example and not limitation. One of skill in the art will appreciate that any number of differently shaped stabilizers can also be used, though not identically disclosed herein, without departing from the spirit of the invention. Many of these embodiments include a length configured to span between the spacer and the vertebral body, but also a transverse component (not shown in FIGS. 6A-6J) in both the spacer-engaging portion and the vertebral-body engaging portion configured to prevent separation between the spacer and vertebral body.

Figure 6A:
FIGS. 6A-6J depict end views of multiple embodiments of different stabilizers.

FIG. 6A illustrates an end view of a substantially "S" shaped stabilizer 601 suitable for use with a spacer (not shown), having channels shaped to receive the stabilizer 601. While not illustrated, the spacer for use with the stabilizer 601 has a complementary channel with a substantially "S" shape, configured to receive the stabilizer 601. The complementary channel can be oriented perpendicular to the upper and lower surfaces of the spacer, or in any other orientation which would allow the stabilizer 601 to fixedly attach the spacer to an adjacent vertebral body.

Figure 6B:
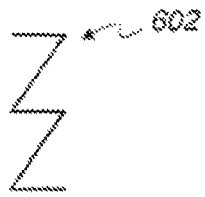
Figure 6C:
Figure 6D:
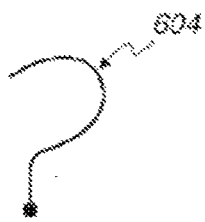
Figure 6E:
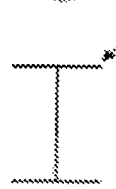
Figure 6F:
Figure 6G:
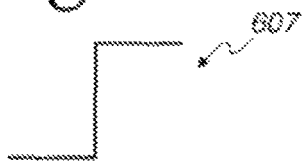
Figure 6H:
Figure 6I:
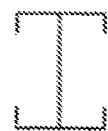

FIG. 6B illustrates an end view of a substantially double "Z" shaped stabilizer 602 configuration suitable for use with a spacer (not shown), having channels shaped to receive the stabilizer 602. While not illustrated, the spacer for use with the stabilizer 601 has a complementary channel having a substantially double "Z" shape, configured to receive the stabilizer 602. The complementary channel can be oriented perpendicular to the upper and lower surfaces of the spacer, or in any other orientation which would allow the stabilizer 602 to fixedly attach the spacer to an adjacent vertebral body.

FIGS. 6C-6J similarly illustrate end views of uniquely shaped stabilizers 603-610 configured for use with suitable spacers (not shown) having complementary channels shaped to receive each uniquely shaped stabilizer. The complementary channels can be oriented perpendicular to the upper and lower surfaces of the spacer, or in any other orientation which would allow the stabilizers to fixedly attach the spacers to an adjacent vertebral body.

Figure 7:
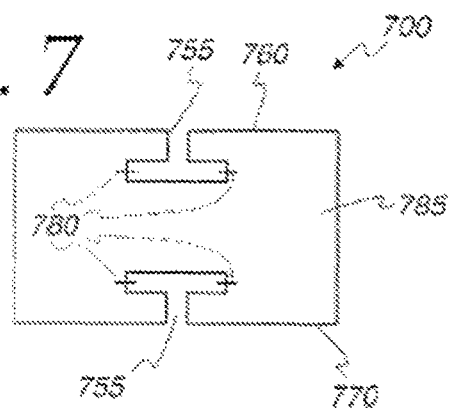
FIG. 7 is an end view of one embodiment of a spacer with self-retaining clips.

FIG. 7 depicts a front end view of yet another embodiment of an interbody spacer 700. The spacer 700 has channels 755 configured to receive at least one stabilizer, such as the stabilizer 605 (see FIG. 6E). The spacer 700 has first and second surfaces, 760 and 770 respectively, configured to engage adjacent vertebral end plates. In this embodiment, the first and second surfaces 760 and 770 are substantially parallel. However, in other embodiments, the first and second surfaces can be angled relative to each other, so as to better support adjacent vertebral bodies in a more natural spinal alignment configuration. The spacer 700 of the present embodiment has two channels 755 for receiving stabilizers such as the stabilizer 605, although it is to be understood that in other embodiments, the spacer 700 can have only one channel or more than two channels.

The interbody spacer 700 can be provided with self-retaining clips 780 to help keep the stabilizers attached to the spacer 700 after insertion. The self-retaining clips 780 can be attached to the proximal surface 785 of spacer 700 and partially extend in front of the channels 755. Preferably, the self-retaining clips 780 have a first and a second position. In the first position, the clip 780 is retracted during insertion of the stabilizer. After the stabilizer is inserted, the clip 780 extends, assuming a second position. The self-retaining clips 780 can be made of a resilient material which allows them to bend inward during insertion of a stabilizer. Once the stabilizer is inserted into the spacer, the self-retaining clips 780 can "pop out" towards their original positions to impede withdrawal of the stabilizers.

FIG. 9 illustrates schematically another embodiment of an interbody spacer 900, similar to the spacers seen in FIGS. 8G and 8H depicting various "Novel VC Spinal Spacers" for use in Anterior Lumbar Interbody Fusion (ALIF), which are commercially available from Alphatec Spine™, Inc. (See website at: http://www.alphatecspine.com/products/interbody.asp).

In preferred embodiments, the spacer 900 is used in spinal fusion surgeries, including ALIF procedures, though other implants and procedures are also contemplated.

The spacer 900, shown schematically in FIG. 9, includes first and second opposite surfaces, 920 and 930 respectively configured to engage superiorly and inferiorly the end plates of adjacent vertebrae. These surfaces 920 and 930 may have ridges, bumps or other protrusions to enhance engagement with the vertebral endplates as discussed above, and shown in FIGS. 8A-8M. As shown in FIG. 9, the first and second opposite surfaces, 920 and 930 may define openings 932 to allow for fusion through the openings. In the embodiment shown in FIG. 9, the first and second surfaces 920 and 930 are substantially parallel. However, in other embodiments, the first and second surfaces can be angled relative to each other, so as to better support adjacent vertebral bodies in a more natural spinal alignment configuration, as discussed previously.

The spacer 900 has a proximal face 934 and a distal face 936, the proximal face 934 corresponding to the end that engages a delivery tool, such as with grooves, indentations or a threaded opening 938, similar to that discussed above with reference to FIGS. 8A-8M. For an ALIF procedure, the proximal face 934 corresponds to the anterior face of the spacer and the distal face 936 corresponds to the posterior face of the spacer.

As illustrated in FIG. 9, the spacer 900 has two channels 955 for receiving suitable stabilizers (discussed in further detail below), although it is to be understood that in other embodiments the spacer can have only one channel and in yet other embodiments, the spacer can have any number of channels.

The channels 955 interface with the first and second surfaces 920 and 930 of the spacer 900, as well as with at least the proximal surface 934 of the spacer 900. The channels 955 shown in FIG. 9 extend through the body of the spacer 900, and interface with the distal surface 936 of the spacer 900. However, in other embodiments, the channels do not extend all the way through the spacer body to interface with the distal surface of the spacer and in other embodiments the channels 950 can interface with side surfaces 960 and 970. The channels 955 are preferably precut into the spacer 900 before insertion into the vertebral space during surgery. Where the spacer 900 has openings 932 in the surfaces 920 and 930, the channels 955 may extend through solid portions of the spacer 900 between the openings 940 (such as through the intermediate bar 972 shown in FIG. 9), or they may be interrupted by the openings 932 so that the channels 955 are provided on opposite sides of the openings 932.

FIGS. 10 and 11 illustrate one embodiment of a stabilizer 1000 suitable for use with the spacer 900 of FIG. 9, where FIG. 10 is an end view of the stabilizer 1000 and FIG. 11 is a perspective view of the stabilizer 1000. The stabilizer 1000 is configured to be partially received within the channels 955 of the spacer 900, with a portion extending out of the channel 955 away from the surface 920 or 930 into the adjacent vertebral body. The stabilizer 1000 is preferably thin enough to slice through bone, yet strong enough to hold onto the bone and stabilize the spacer 900 after insertion. The stabilizer 1000, as illustrated, has two plates/walls 1050 and 1060 and a wall/retaining member 1070 attached together and configured in a "T" shape as seen in FIG. 10. The stabilizer 1000 is preferably made of metal but it can also be made of any suitable material including, but not limited to: Ti-6Al-4V, ELI, ASTM F 136, commercially pure titanium (for example, Ti-CP2, ASTM F 67, CPTi, etc.). The plates 1050 and 1060 of stabilizer 1000 preferably have sharp edges 1072 and 1074 which are thin and strong enough to slice through vertebral bone when a sufficient force is applied to the anterior surface 1076 of stabilizer 1000. Stabilizer 1000 can also have self-retaining clips (not shown) attached to it to help keep the stabilizer 1000 attached to the spacer 900 after insertion, as discussed previously.

FIG. 12 is an end view of the spacer 900 of FIG. 9 operably implanted within a spine 1201 from the anterior side of the spine. The spacer 900 is inserted between two bone portions/vertebrae 1210 and 1220 and two stabilizers 1000, according to FIGS. 10 and 11, are inserted into the channels 955 of the spacer 900 and into the adjacent vertebral bodies 1210 and 1220.

During operation, the diseased/damaged disk (not shown) is partially or completely removed and preferably replaced with a spacer 900 with the proximal surface 934 of said spacer 900 facing anteriorly. Stabilizers 1000 are then lined up with the channels 955 of the spacer 900 and driven translationally into vertebral bodies 1210 and 1220 by applying sufficient force to the stabilizers 1000. The stabilizers 1000 are simultaneously driven into the vertebral bones 1210 and 1220 and received into their respective channels 955. However, it is to be understood that in some embodiments, stabilizers 1000 can be inserted into the vertebral bones 1210 and 1220 before spacer 900 is inserted. It is further conceivable, with this and other embodiments, that the stabilizers could be pre-joined to their respective spacer before the stabilizer is translated into the bone portions.

It should be understood that all of the particular structures described in each embodiment may be used in any other embodiment. That is, the invention contemplates that the different features in the embodiments disclosed herein may be interchanged.

Figure 13:
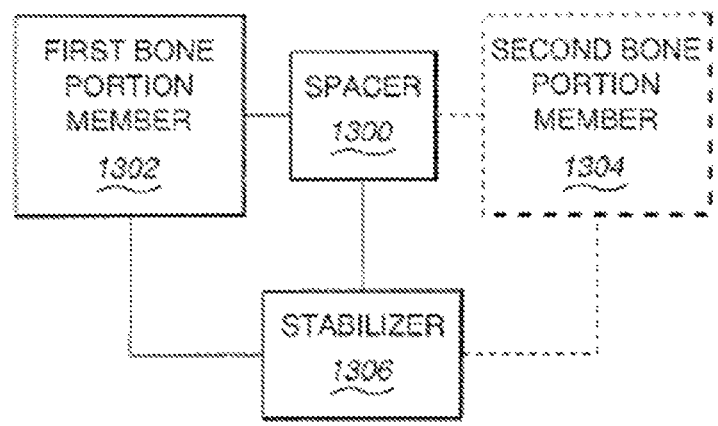
FIG. 13 is a schematic representation of an inventive system, including at least one bone portion/member with an interbody spacer fixed thereagainst utilizing a stabilizer.

As noted previously, it is contemplated that the invention can be practiced as part of any medical procedure involving the placement of a spacer between adjacent bone portions. This generic concept is shown schematically in FIG. 13, wherein a spacer 1300, representing all spacer configurations disclosed herein, as well as others, is operatively joined to at least a first bone portion 1302. It is conceivable that the spacer 1300 would be joined to only the first bone portion 1302. However, more commonly, the invention would be practiced by using the spacer 1300 between the first bone portion 1302 and a second bone portion 1304, which is shown to be optional by the depiction of the latter schematically in FIG. 13 in dotted lines. The stabilizer 1306, as shown in FIG. 13, is intended to represent all stabilizer constructions disclosed herein, as well as others. The stabilizer 1306 operatively interacts between the spacer 1300 and either of the bone portions 1302, 1304.

With the system as shown in FIG. 13, the spacer 1300 is configured to be placed between the first and second bone portions 1302, 1304. The stabilizer 1306 is configured to be joined: a) to each of the first bone portion 1302 and spacer 1300; and b) to at least one of the first bone portion 1302 and spacer 1300 by being translated relative to the at least one of the first bone portion 1302 and spacer 1300 along a first line.

As noted previously, the stabilizer 1306 preferably extends into its associated bone portion 1302, 1304 over a majority of the dimension of that bone portion 1302, 1304 along a corresponding first translation line L, as seen in FIG. 2 for the stabilizer 200.

As seen in FIGS. 2 and 3, the stabilizer 200 has the aforementioned plates/walls 240, 250, 260, with a first and second of the walls 250, 260 having facing surfaces S1, S2, respectively. With the stabilizer operatively positioned, as seen in FIG. 4, a part P1 of the vertebra 420 and a part P2 of the spacer 100 are captive between the facing surfaces S1, S2 to stabilize the spacer and bone portion/member 420.

Because each of the plates/walls 240, 250, 260 has a substantial width dimension transversely to the line L, the connection is stabilized in all critical dimensions. Preferably, the plates/walls 240, 260 extend into the spacer 100 along a majority of the dimension of the spacer 100 along the line L.

More preferably, the spacer walls 240, 250, 260 extend along substantially the entire dimension of the spacer 100 along the line L.

Each of the stabilizer configurations defined herein has surfaces that produce the above captive arrangement. By reason of the depicted configurations, these stabilizers also produce multidimensional reinforcement between the fused components.

As seen in FIG. 4, the spacer surface 120 abuts to an adjacent surface AS1 on the vertebra 410, with the opposite spacer surface 130 abutting the adjacent surface AS2 on the vertebra 420. It is contemplated that the stabilizers 200 extend through at least one of the surfaces 120, AS1 and 130, AS2 at locations where the surfaces abut. More preferably, each stabilizer extends continuously through each of the adjacent faces 120, AS1 and 130, AS2.

It is conceivable that a spacer could be devised having a U-shaped configuration, with spaced legs parallel to each other and the line L, such that the spacer does not penetrate any of the surfaces 120, 130, AS1, AS2. This spacer would be inserted similarly in a translational path.

As seen in FIG. 4, the surfaces 120, 130, AS1, AS2 are shown to be generally flat and parallel to each other. The translation line for the stabilizers 200 during assembly is substantially parallel to each of the surfaces 120, 130, AS1, AS2.

As also seen in FIG. 4, the inventive stabilizer 200 is constructed so that it extends only partially through the dimension of the spacer 100 between the surfaces 120, 130.

As further seen in FIG. 4, each of the components 410, 420, 100 has a peripheral surface, PS1, PS2, PS3. The stabilizers 200 can be constructed so that the stabilizers do not project from any of the exposed peripheral surfaces PS1, PS2, PS3. While preferred, this is not a requirement.

Additional variations of the inventive structure are shown in FIGS. 14-21.

Figure 6J:
Figure 14:
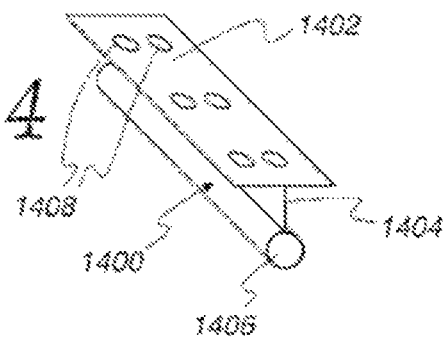
FIG. 14 is a perspective view of a modified form of stabilizer, according to the invention.

In FIG. 14, a fenestrated form of stabilizer 1400 is depicted with a configuration corresponding to the stabilizer 610 in FIG. 6J. The stabilizer 1400 has flat walls 1402, 1404 which combine to produce a "T" shape. A cylindrical wall 1406 is provided at the bottom of the "T".

The wall 1402, that is embedded in the bone, has discrete openings 1408 into which bone can grow to thereby further secure the connection between the stabilizer 1400 and bone.

Figure 15:
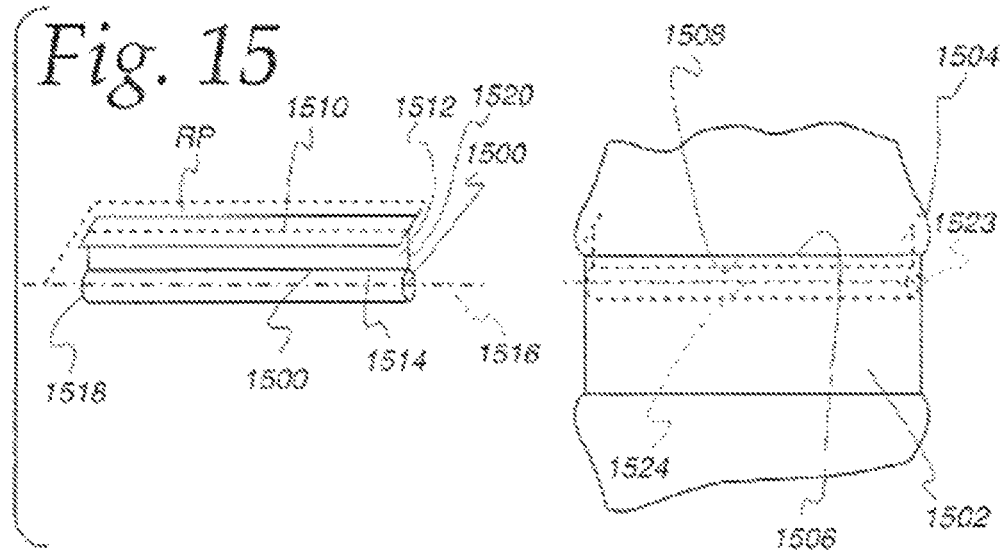
FIG. 15 is a fragmentary, perspective view showing a spacer against a bone portion and a further modified form of stabilizer that is configured to urge the bone portion and spacer towards each other as the stabilizer is inserted.

In FIG. 15, a stabilizer 1500 is shown for use in conjunction with a spacer 1502 and bone portion 1504 to cause facing surfaces 1506, 1508 on the spacer 1502 and bone portion 1504 to be urged towards each other with a progressive camming action as the stabilizer 1500 is inserted.

The stabilizer 1500 has flat walls 1510, 1512 that produce a "T" shape, at the bottom of which a cylindrical wall 1514 is provided. The wall 1510 resides within a reference plane RP. The wall 1514 has a central axis 1516 that is non-parallel to the reference plane RP. More specifically, the axis 1516 is oriented so that the space between the reference plane RP and axis 1516 increases between the trailing end 1518 and leading end 1520.

The spacer 1502 has a channel 1523 to accept the wall 1514 and a part of the wall 1512. The axis 1524 of the channel portion that accepts the cylindrical wall 1514 is substantially parallel to the spacer surface 1506. As a result, as the leading end 1520 is translated into the channel 1523 and the wall 1510 cuts into the bone portion 1504, the movement of the cylindrical wall 1514 into the channel 1523 produces a camming action that progressively urges the surfaces 1506, 1508 against each other.

In FIG. 16, a stabilizer 1600 is shown in relationship to a spacer 1602 and bone portion 1604, wherein a similar camming action is produced by essentially reversing the construction shown in FIG. 15. That is, the axis 1606 on the spacer 1602, that corresponds to the axis 1524, is inclined relative to the spacer surface 1608, whereas the axis 1610 for the cylindrical wall 1612 is substantially parallel to a reference plane RP1 containing the flat wall 1616.

Using the concepts disclosed in FIGS. 15 and 16, the components can be configured to produce the desired compressive force between a spacer and bone portion, as well as potentially producing such a force at both sides of the bone portion.

While the walls 1514, 1612 are shown with a cylindrical shape, it is contemplated that the shape may be non-circular in cross-section so as to be keyed within the cooperating channel to further stabilize the connected spacer and bone portion.

The invention also contemplates that locking assemblies might be incorporated into the stabilizers and spacers to avoid inadvertent backing out or extension of the particular stabilizer at a fusion location. In FIG. 17, one form of locking assembly is shown at 1700. A stabilizer 1702 has the same general construction as the stabilizer 1600 in FIG. 16, with the exception that there is an enlargement 1704 on the trailing end thereof. A cooperating spacer 1706 has a complementary channel 1708 including an enlarged receptacle 1710 that is complementary to the enlargement 1704. The enlargement 1704 and receptacle 1710 define cooperating connecting parts on the locking assembly 1700. With the stabilizer 1702 translated along the line L to a fully inserted position, the enlargement 1704 snap fits into the receptacle 1710 to produce a detenttype action.

In the depicted embodiment, the enlargement 1704 is countersunk so as to not project from the spacer 1706. However, the parts could be configured so that there is a flush relationship or a projection of the enlargement 1704 from the spacer 1706.

With this arrangement, the locking assembly 1700 maintains the stabilizer 1702 in its operative position shown in FIG. 17.

Figure 19:
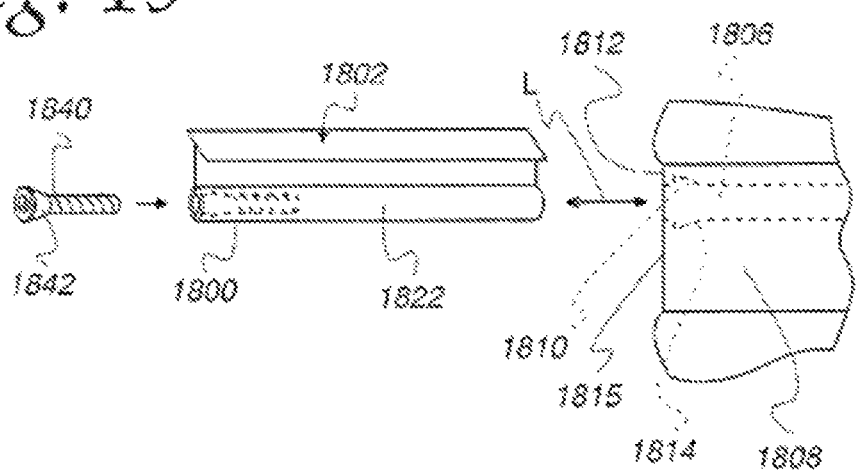
FIG. 19 is a perspective view of a modified form of stabilizer and spacer, similar to that shown in FIG. 18, with a locking assembly thereon in an assembly state, the stabilizer aligned to be directed into the spacer and abutted bone portion and with a spreader element aligned to be directed into the stabilizer to change the locking assembly from the assembly state into a locked state.
Figure 20:
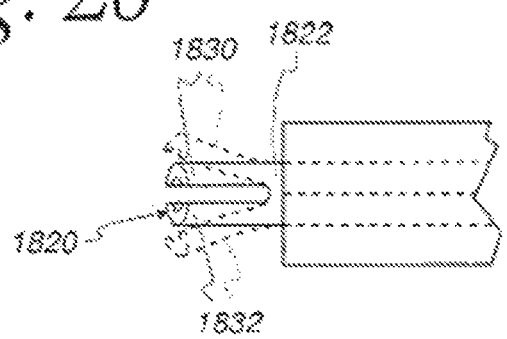
FIG. 20 is an enlarged, fragmentary, plan view of the stabilizer in FIG. 19 with the locking assembly component on the stabilizer shown in solid lines as it is configured with the locking assembly in an assembly state and in dotted lines as it is configured with the locking assembly in the locked state.

Another type of locking assembly is shown in two different forms in FIGS. 18-20. The locking assembly in FIGS. 19 and 20 consists of a reconfigurable body 1800 on a stabilizer 1802. The stabilizer 1802 is directed into a channel 1806 on a spacer 1808. The channel 1806 has a flared region 1810 inset from a wall portion 1812. The flared region 1810 defines an annular shoulder 1814 set inwardly from a surface 1815 on the spacer 1808.

With the stabilizer 1802 translated into the channel 1806, a bifurcated end 1820 of a cylindrical wall 1822 resides at the flared region 1810. The bifurcation at the end 1820 produces diametrically opposite tabs 1830, 1832 between which a threaded spreader element 1840 can be directed. The spreader element 1840 has an outer surface 1842 with a portion having a progressively increasing diameter. By threading the spreader element 1840 into the wall 1822, the tabs 1830, 1832 are reconfigured by bending radially outwardly to seat behind the annular shoulder 1814, whereupon the stabilizer 1802 is blocked from being withdrawn. The spreader element 1840 thus changes the locking assembly from the assembly state, as shown in solid lines in FIGS. 19 and 20, to a locked state as shown in dotted lines in FIG. 20. The tabs 1830, 1832 and flared region 1810 make up cooperating connecting parts on the locking assembly.

In FIG. 18, the locking assembly consists of corresponding tabs 1830', 1832', on a stabilizer 1802', that cooperate with a complementarily-shaped region 1810' of a channel 1806'. The tabs 1830', 1832' may spring oppositely into the region 1810' without requiring insertion of a separate spreader element.

Figure 21:
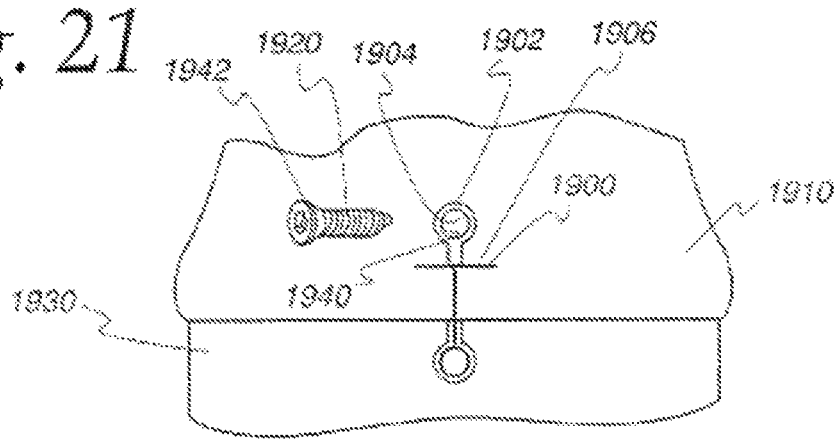
FIG. 21 is an elevation view of a modified form of stabilizer joined with a spacer and bone portion with a locking tab secured against the bone portion with a fastener.

As an alternative form of locking assembly, as shown in FIG. 21, a stabilizer 1900 is provided with a locking tab 1902. The locking tab 1902 has a bore 1904 therethrough and is bent on site or pre-bent to be substantially orthogonal to the plane of a wall 1906 on the stabilizer 1900. With this arrangement, the locking tab 1902 overlies a part of the exposed bone portion 1910 whereby a threaded fastener 1920 can be directed therethrough. The fastener 1920 is preferably a threaded component. A similar tab (not shown) might be provided to be securable to the cooperating spacer 1930 in like fashion.

Threads 1940 might be provided around the bore 1904. The threads 1940 may be interrupted or placed at multiple points to allow for a controlled cross-threading of the head 1942 of the fastener 1920 as it is inserted. This allows the fastener 1920 to be inserted at any optimal angle.

In other variations, stabilizers, such as the stabilizer 1400, may be treated by applying bone ingrowth coating, as on the wall 1402. The coating may be in the form of beads, mesh, or hydroxyappetide. This promotes rapid ingrowth into the openings 1408. This same concept may be used on all other stabilizers described herein.

FIGS. 22A-22D show a further variation of a spacer presented earlier. Like the spacer 900 illustrated in FIG. 9, the spacer/cage 2200 has a body 2290 with side surfaces 2260, 2270, channels 2255, 2265, proximal and distal faces 2240, 2250, respectively, first and second opposite surfaces 2210, 2220, an opening 2232 for graft or other bone substitute material, and protrusions in the form of teeth 2235.

FIGS. 23A-23E show a further modified form of stabilizer 2300. Like the stabilizers 1000, 1400 illustrated in FIGS. 10, 11, & 14, the stabilizer 2300 has a wall/plate 2310, a web/wall 2320, and cylindrical wall/retaining member 2330 with a sharp leading edge 2340 to cut bone against which it is advanced. The stabilizer 2300 has self-retaining clips 2350 in the form of barbs/tabs, generally of the type illustrated at 272 in FIG. 2.

The spacer body 2290 has a height "h" sized to fit within a portion of the intervertebral disc space. The intervertebral space, as defined by the shape/footprint of the vertebral body endplates, is generally "D"-shaped and the implant spacer/cage 2200 preferably has an outer profile shape to fill substantially the entire disc space. Interbody implants may take streamlined profiles, as between anterior and posterior sides, to provide less invasive entry into the intervertebral space during surgery and to help accommodate to the surgical approach. Regardless of their configuration, it is desirable that the combined spacer and stabilizer have a "zero-profile", meaning that no part of either component protrudes from the space between adjacent bone portions. Exemplary differing profiles are illustrated in FIGS. 8A-8M. For example, rectangular or banana-shaped profiles may be used since they are thinner in a width dimension, thereby requiring a smaller/less invasive path of entry into the intervertebral disc space. In one preferred form shown in FIG. 22A, an anterior wall portion 2275 of the implant, that is part of a continuous profile wall 2280 and defines the surface 2260, has a gentle convex arc similar to the anterior wall of the vertebral body and a predetermined width between the surfaces 2260 and 2270 to facilitate minimally invasive entry along an axis/line generally parallel to the lengths of the channels 2255 and 2265.

The outer profile wall 2280 defines one or more openings 2232, 2295 for packing bone graft or other bone substitutes to ultimately facilitate fusion between vertebral bodies. The opening 2232 is completely surrounded by the wall 2280 to hold the graft material within the body 2290. The wall 2280 may have openings partially or fully therethrough for packing graft. As seen in FIG. 22A, two graft apertures/openings 2295 are formed within the wall 2280 and can be utilized for adding additional graft or hydration to the graft within the opening 2232.

The proximal face 2240 of the wall 2280 of the spacer/cage 2200 incorporates features for the attachment of one or more auxiliary instruments utilized to install the spacer/cage 2200 within the intervertebral space. In this embodiment, instrument attachment structure is in the form of two bores 2215a, 2215b with at least one hole/bore 2215a threaded for attachment to a complementarily-threaded insertion facilitating instrument, identified schematically in FIG. 22A at 2205. The second hole 2215b is also shown to be threaded, though this is not required, and configured to engage a boss from the insertion instrument 2205 as a means to counter torque and therein limit rotation between the spacer/cage 2200 and insertion instrument 2205, to be described later. The instrument attachment portion structure could also be in other forms such as a boss, slot, hole, groove or other feature for an auxiliary instrument to attach. If both holes/bores 2215a, 2215b are threaded and usable individually to cooperate with the instrument 2205, the unused hole/bore 2215a, 2215b is available as a backup, as in the event one of the holes/bores becomes stripped.

Figure 22C:
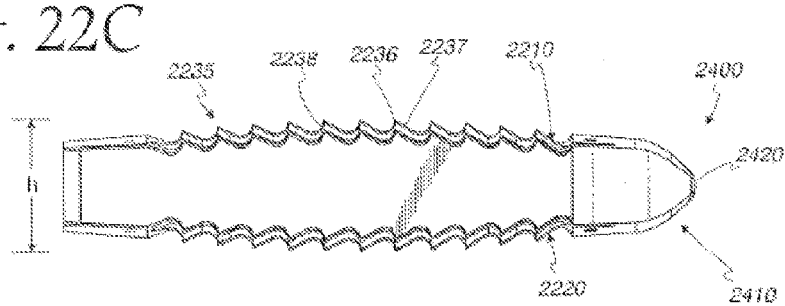
FIG. 22C is a side view of a spacer embodiment.
Figure 22D:
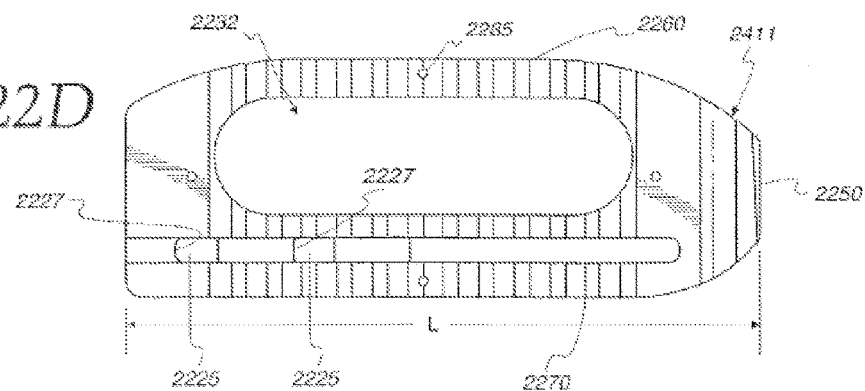
FIG. 22D is a top view of one embodiment of a spacer.

The distal face 2250 of the body 2290 has a nose portion 2400 as seen most clearly in FIG. 22C, configured to ease entry into the intervertebral space by wedging between vertebral endplates during insertion. This nose portion 2400 preferably has a lead in angle taper at 2410, in combination with a radiused end 2420 defining a blunt arrow or bullet shape. As seen from the top view in FIG. 22D, the side surfaces 2260, 2270 may also have a taper or radius 2411 where they blend into the radiused end 2420 at the distal face 2250. This is helpful to wedge soft tissue to the sides of the nose portion 2400 during insertion.

The body 2290 also has a stabilizer attachment or anchor portion 2245 for securement of the stabilizer 2300 to the spacer/cage 2200. This anchor portion 2245 consists of one, and preferably two, of the aforementioned channels 2255, 2265 illustrated and otherwise known as keel tracks in this embodiment. The channels 2255, 2265 are at the site where the stabilizer 2300 attaches and is secured to the spacer body 2290. The channels 2255, 2265 are shown through the surfaces 2210 and 2220, but in some embodiments may be on other surfaces, such as the surfaces 2260 and 2270. The channels 2255, 2265 are preferably configured wherein one channel 2255 is adjacent one bone portion and the other channel 2265 is adjacent another between which the spacer/cage 2200 resides. The channels 2255, 2265 in this embodiment each is in the form of a T-shaped slot preferably extending along a linear path, although the path could be arced, when complemented by an arced stabilizer, or otherwise shaped. The T-shaped slot shown is configured to accept and contain a stabilizer, such as the stabilizer 2300 with a body 2390. The stabilizer body 2390 has one or more reconfigurable tabs/barbs 2350, and in this embodiment two such tabs/barbs 2350 generally of the type 1830, 1832 shown in FIGS. 19 and 20, and described in greater detail below.

At least one of the channels/keel tracks 2255, 2265 has a stabilizer stop portion 2276, here illustrated as a termination of the T-shaped channel 2255 which prevents the stabilizer 2300 from advancing beyond the spacer body 2290 and the implant spacer/cage 2200 from advancing out of the intervertebral space once the stabilizer 2300 is locked in a predetermined operative position within the vertebral body. With the stabilizer body 2390 abutted to the stop portion 2276, the stabilizer 2300 is consistently located in its optimal operative relationship to the spacer/cage 2200. The stabilizer anchor portion 2245 in this embodiment also has a stabilizer lock portion illustrated in FIG. 22B as an undercut region 2225 for receipt of the tabs/barbs 2350 on the stabilizer 2300.

In FIG. 22B, both of the opposite surfaces 2210, 2220 of the body 2290, on the superior and inferior sides thereof, have channels 2255, 2265 respectively formed therethrough with each shown as a T-shaped slot. The body 2290 of the spacer/cage 2200 may have one or more marker housings 2285 shown here in the form of holes or other recess for the placement of tantalum markers M. The markers M assist placement of the implant through imaging in the predetermined intervertebral position.

Figure 24A:
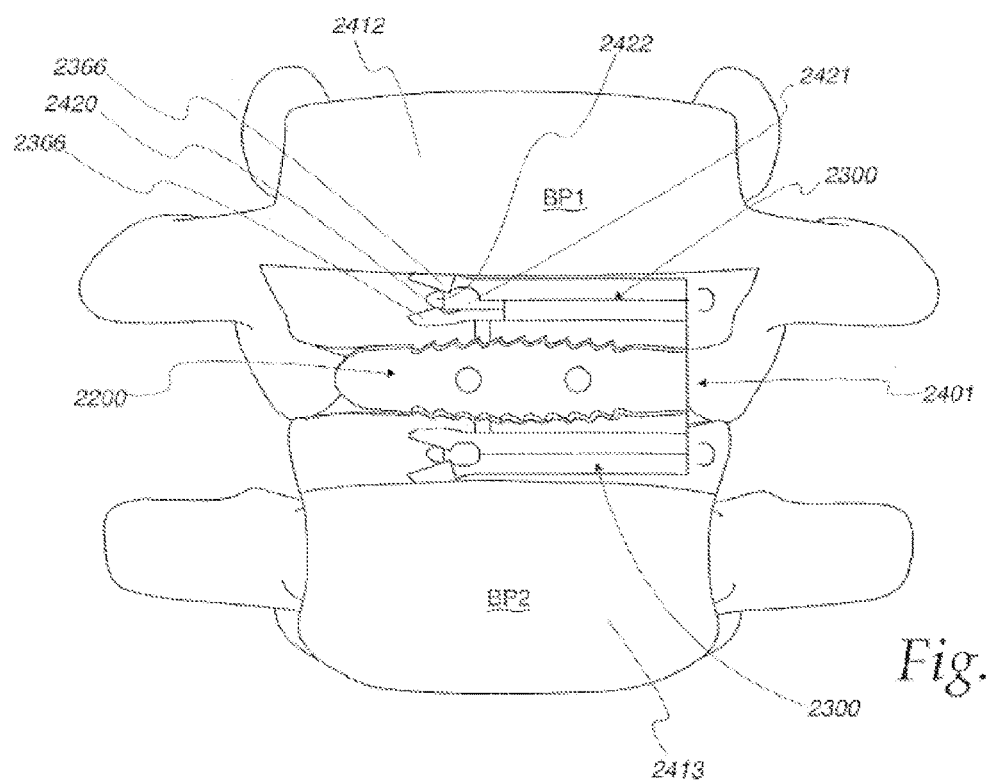
FIG. 24A is a front view of a spacer-stabilizer assembly installed within the intervertebral space, with the superior and inferior vertebral bodies partially resected for viewing of the deployed stabilizers as they would reside in the bone.

As shown in FIGS. 22A and 22C, the first and second opposite surfaces 2210, 2220 of the implant body 2290 ride directly against bone. One or both surfaces 2210, 2220, as shown, may have one or more of the teeth 2235 or other protrusions to assist securement of the spacer/cage 2200 in its predetermined operative position between the vertebral body bone portions BP1, BP2, as seen in FIG. 24A. The teeth 2235 preferably each has a peak 2236 which may be in the form of a point, or broader surface such as a line, preferably extending generally transverse to the entry line/axis. Each tooth 2235 has an entry face 2237 that may be sloped to assist moving the implant body 2290 into the intervertebral space, and a trailing face 2238 that is more steeply sloped to engage a bone portion to prevent the implant body 2290 from backing out of the implant space. The teeth 2235 are sized deep enough to dig into bone yet shallow enough to avoid substantial loss of intervertebral space following implant insertion once there is subsidence of the teeth or other protrusions 2235.

The opposite surfaces 2210, 2220 are preferably optimized to have enough area to adequately support and distribute the forces between the vertebral body endplates while having adequate sized openings 2232 for a strong fusion. In turn, the wall 2280 of the body 2290 is thick enough such that it will not buckle under the endplate forces, dependent on the material of construction. The distance h, between the surfaces 2210, 2220, is generally equal to the distance between vertebral body endplates when separated by a healthy intervertebral disc. These surfaces could be generally flat; however, they are preferably contoured to match the contour of the facing vertebral endplate, which is typically slightly convex. An example of the contour can be seen in FIG. 22C with the height bulged slightly near the middle of the spacer/cage 2200. Similarly, the opposite surface portions 2210, 2220 may be angled in relation to each other to accommodate to the intervertebral space. This space is commonly angled from anterior to posterior. As an example, the embodiment in FIG. 22C is angled 6 degree, as reflected by a slightly greater height on the anterior portion of the implant and sloping to a slightly shorter height on the posterior portion of the implant. This corresponds to the normal angulation in the lumbar spine.

The stabilizer 2300 functions to: secure the body 2290 portion in a predetermined operative position relative the adjacent bone portions; assist against back out and over travel of the spacer/cage 2200 from this position; and help positively hold surrounding bone close to the spacer 2200, thereby facilitating a successful fusion. The wall/retaining member 2330 on the stabilizer 2300, in the preferred embodiment depicted, has a cylindrical shape. The stabilizer 2300 has a reconfigurable body 2390, generally of the type illustrated in FIGS. 19 and 20, but could have a multitude of other configurations also described elsewhere. The stabilizer 2300 may be integrated with the spacer/cage body 2290, but it is preferred that it be a separate component as shown clearly in FIGS. 23A and 23B. The stabilizer 2300 has a spacer anchor 2370 that resides within the stabilizer anchoring portion 2245 on the spacer/cage 2200 with the spacer/cage 220 and stabilizer 2300 operatively connected.

The base wall 2310 is flat and configured to be directed into a complementarily-shaped portion of either of the channels 2255, 2265 on the body 2290. In this case, the base wall 2310 and the flat web wall 2320 form a "T"-shaped portion to slide in and reside in one of the Tshaped channels 2255, 2265. The cooperating "T" shapes are such that the spacer anchor 2370 can be guided consistently within the channels 2255, 2265 along the assembly line/axis without excessive resistance but will be closely enough matched to be stabilized in multiple dimensions relative to the spacer/cage 2200 without appreciable wobble. The lower region of the web wall 2320 is thickened where it engages the spacer/cage 2200. The exemplary channel 2255 is bounded by a surface 2266.

The complementary shapes of the channels 2255, 2265 and spacer anchor 2370 may take many other forms besides a "T" shape. For example, the base wall 2310 could have a triangular, elliptical, or round profile. A leading nose 2311 on the base wall 2310 serves to lead the base wall 2310 into a channel 2255, 2265 of the stabilizer anchor 2245. Similar to the spacer nose 2400, it is preferred that the nose 2311 is tapered and radiused to ease entry. As seen in FIG. 23C, the base wall nose 2311 extends slightly ahead of a reconfigurable nose 2361 on the body 2390 such that the base wall 2310 can begin to seat in one of the channels 2255, 2265 before the reconfigurable nose 2361 is situated to seat in the body of the vertebrae, thereby easing insertion complications.

Figure 23A:
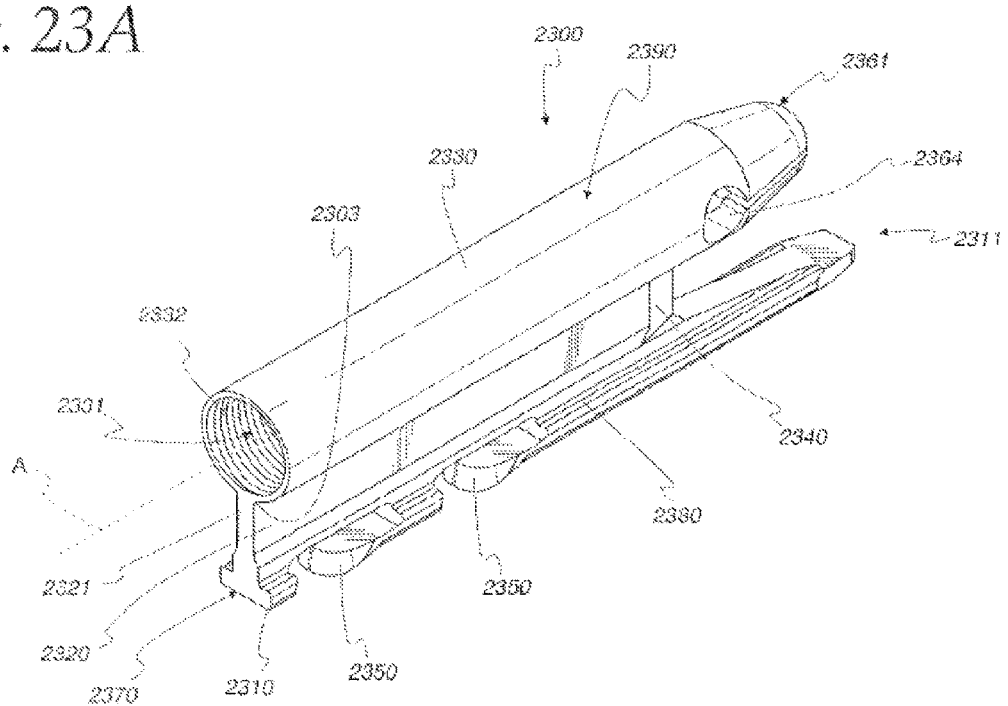
FIG. 23A is a perspective view of one embodiment of a stabilizer.
Figure 23B:
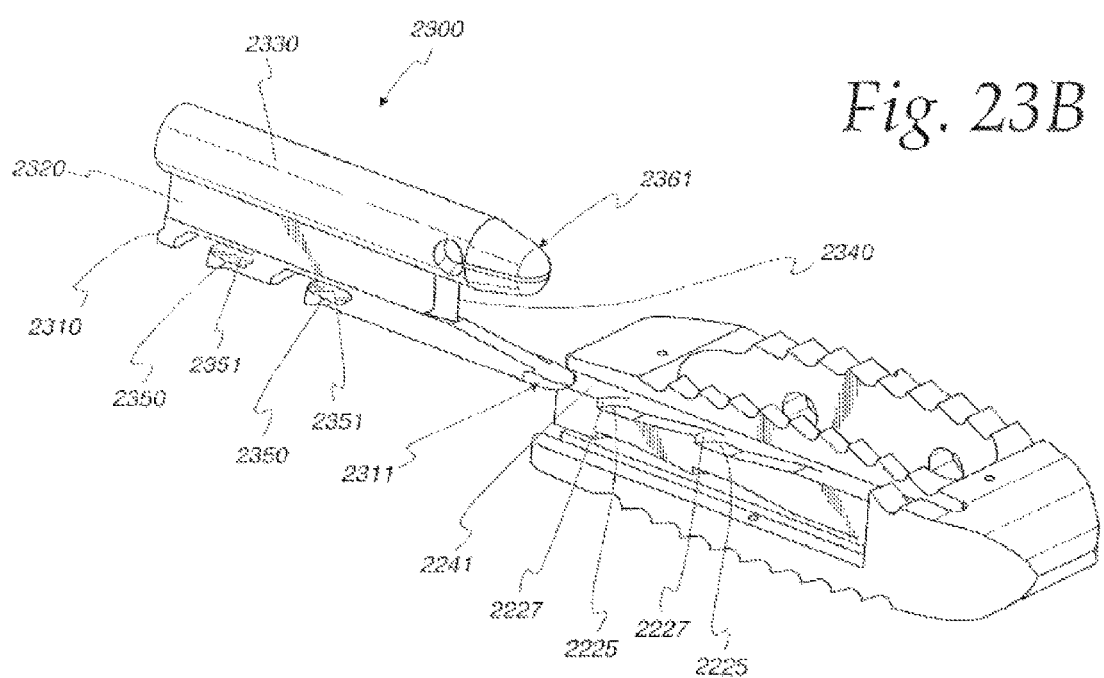
FIG. 23B is a perspective view of a stabilizer with its base nose just beginning to enter into a channel of a spacer, with a portion of the spacer resected for reviewing purposes.

Any portion of the spacer anchor 2370, but preferably the base wall 2310, includes a self-retaining portion. The base wall 2310 has a generally flat wall surface 2380 that is abuttable to the spacer/cage surface 2266 to prevent pullout of the base wall 2310 from the channel 2255 in a direction transversely to the channel length. A preferred configuration of the self-retaining portion is shown in FIG. 23B in the form of the aforementioned tab/barb 2350. One or more of the tabs/barbs 2350 may be used. These tabs/barbs 2350, shown as two in number, are each configured to engage the stabilizer lock portion, shown in the form of a like number undercut regions 2225. The tabs/barbs 2350 are formed on the stabilizer base wall 2310 and extend slightly below the base wall 2310. As the base wall 2310 is inserted into exemplary channel 2255, resilient arms 2351 on each tab/barb 2350 serially engage an edge 2239 where a face 2241 bounding the channel 2255 meets the proximal face 2240 and deflects up then re-seats itself under a restoring force when it aligns over an undercut region 2225 on the stabilizer interlock. This progression is illustrated in FIGS. 23B through 23E.

A portion of the stabilizer body 2390 is cut away in the illustrations for enhanced visualization. FIG. 23B illustrates the leading base wall nose 2311 approaching one of the channels 2255 with the spacer 2200 and stabilizer in a pre-assembly relationship. FIG. 23C illustrates the stabilizer 2300 partially seated into the spacer/cage 2200 but before the tabs/barbs 2350 are engaged. FIG. 23D illustrates the stabilizer 2300 further translated into the spacer/cage 2200. The underside surface of each self-retaining tab/barb 235 abuts the bottom surface 2241 of the channel 2255 and is guided therealong until the tabs/barbs 2350 align over their respective undercut region 2225 whereupon a restoring force in the deflector arms 2351 drives them into the undercut regions 2225. A curved edge/blocking surface 2227 bounding each undercut region 2225 confronts the trailing edge/blocking surface of one of the tabs/barbs 2350 to block the stabilizer 2300 from backing out. FIG. 23E illustrates the stabilizer 2300 fully translated into the channel 2255 and the spacer 2200 and stabilizer in assembled relationship. Stop 2275 prevents further translation of the stabilizer 2300 moving in its assembly direction. The stabilizer 2300 is thus fully locked consistently in a preselected, optimal operative position relative to the spacer/cage 2200.

The tabs/barbs 2350 may each have a sloped leading surface 2353 to assist deflection of the tabs/barbs 2350 upon entry and a steeper surface 2354 on the trailing end of the tabs/barbs 2350 to confront the edges 2227 bounding the undercut regions and prevent backout. The transition between the leading surfaces 2353 and trailing surfaces 2354 may be rounded to prevent hang-ups. The spaces above the tabs/barbs 2350 are open to form relief pockets 2352 to allow for adequate deflection of the tabs/barbs 2350 when inserting into the channel, as described previously. The barb arms 2351 are long enough to assure adequate deflection of the barbs 2350 while minimizing plastic deformation. The backout stop edges 2227 are each in the form of a steep wall located at the trailing end of the undercut regions 2225, one of which is adjacent the proximal face 2240 with the spacer 2200 and stabilizer 2300 in operative relationship. The stop edges 2227 secure the stabilizer 2300 captively in conjunction with the stop portion 2276 and help prevent the tabs/barbs 2350 from slipping out of the undercut regions 2225 as might allow unintended release of the stabilizer 2300 from the spacer 2200.

With this arrangement, the stabilizer 2300 can be translated in a first direction in a first path relative to the spacer/cage 2200 and thereby snap-fit consistently into the same operative relationship therewith. The trailing surface 2354 and edges 2227 function as oppositely facing/blocking surfaces that confront each other to prevent separation of the operatively joined stabilizer 2300 and spacer/cage 2200 with the spacer/cage 2200 and stabilizer 2300 in operative relationship.

One preferred interface between the flat base wall 2310 and the channels 2255, 2265 is the depicted "T"-shaped configuration. Although clearly other shaped channel interfaces can be used, such as triangular, this "T"-shaped interface creates good stability between the stabilizer 2300 and the spacer/cage 2200 and in turn results in greater stability of the adjacent bone portions. The "T"-shaped profile has beneficial strength to thickness ratio; that is, the base wall 2310 is thin yet strong, therein maximizing the material thickness of the spacer/cage 2200 available to secure the stabilizer 2300 thereto. This permits narrower implants to be created for use in patients having small stature or narrow disc spaces. It is preferred that the interface gap between the surfaces of the base wall 2310 and the walls bounding the channels 2255, 2265 is large enough to allow insertion of the stabilizer 2300 into the track without struggle, yet small enough to minimize motion between the two components, thereby adequately stabilizing the surrounding bone.

Depending on where the implant is used in the skeleton, or elsewhere as is also contemplated, the positioning of the stabilizer 2300 on the spacer/cage 2200 may affect performance and/or ease of insertion. Therefore the stabilizer 2300 may be positioned midline or asymmetrically or at any number of angles with respect to the body portion of the implant. For example, in the illustrated and preferred embodiment of FIG. 22B, preferably utilized for a lateral surgical approach, the stabilizer 2300 is positioned to the posterior side of the implant as illustrated by the position of the stabilizer anchor channels 2255, 2265. When appropriately placed in the intervertebral space, this position locks the stabilizer 2300 to the endplate of the vertebrae near the center of axis of rotation between the vertebral bodies. This placement is also particularly effective at resisting the vertebral endplate from lifting away from the opposite surface portions 2210, 2220 of the implant body 2290. In this embodiment, the asymmetrical positioning of the stabilizer 2300 also makes possible the use of a single large opening 2232 for the bone graft instead of two smaller ones. In most cases, the channels/keel tracks 2255, 2265 will be generally collinear with the path of entry of the surgical approach.

The web wall 2320 is typically in the form of a thin wall, preferably about 1 mm or less, with a sharp leading edge 2340 to slice through bone as the stabilizer is advanced in its assembly direction and path, and has a profile narrower than the diameter of the cylindrical wall 2330 so the cylindrical wall 2330 is captive and cannot be pulled through the bone space created by the web wall 2320, thereby securing the bone tightly to the opposite surfaces 2210, 2220 of spacer/cage 2200. The web wall 2320 spans along a majority of the length of the stabilizer 2300 between the cylindrical wall 2330 and flat base wall 2310. It is preferred that the cylindrical wall 2330, the web wall 2320, and the base wall 2310 all extend fully to the stabilizer's proximal face 2321, that is substantially flat and resides in a plane generally orthogonal to the length of the stabilizer 2300. The web wall 2320 is shown as the shortest of the three walls. This wall length difference facilitates insertion since the sharp edge 2340 will not encounter the wall of the vertebral body until after the reconfigurable nose 2361 and the base wall nose 2311 are at least partially inserted into the vertebral bone and channel 2255, 2265, respectively.

This web edge 2340 is sharpened to cut through bone during insertion. This sharpened edge 2340 may be vertical or sloped forward or back to facilitate the cutting action. In the preferred embodiment, the web edge 2340 is straight, but may also be curved or serrated. It is preferred that the web wall 2320 be continuous, but it may include apertures for eventual bone ingrowth. However, these should be limited so as to not substantially weaken the web wall 2320. A continuous web will also ease future removal, if necessary, since bone cannot grow through the web openings. The web wall 2320 in FIG. 23A rises vertically from the flat wall track 2310; however, this web could rise at an angle or in a curved path if so desired, as did those in earlier embodiments, such as that in FIG. 2.

The cylindrical wall 2330 in this preferred embodiment is a portion of the stabilizer 2300 that is configured with a surface 2303 that faces the base wall surface 2380, to prevent the stabilizer from being pulled through bone as the cooperating bone portion attempts to pull away from the spacer/cage 2200 during normal movements of the patient. For purposes of the description and claims herein, the surfaces 2303, 2380 are considered to be "facing" over the extent to which they are cooperatively capable of exerting a captive force on components therebetween. Essentially, the convex surface 2303 faces the base wall surface 2380 at all locations where the surface 2303 faces the plane within which the surface 2380 resides. The cylindrical shape of the wall 2330 affords a substantial bone contact area and thus improves overall stability without occupying a detrimentally large bone volume. The surface 2380 does not have to be formed as part of a continuous cylindrical surface as depicted, but is preferably convex where it faces the base wall surface 2380. The convex portion preferably has a radius at or adjacent the lengthwise central axis shown for the cylindrical wall 2330. The cylindrical wall 2330 may alternatively be an enlarged portion of the implant such as an elongated bulb or cylinder and is configured to prevent pullout from the vertebrae like the "T" shaped walls of the stabilizer spacer anchor 2370 prevent pullout from the channels 2255, 2265. The cylindrical shape of the cylindrical wall 2330 is well suited to occupy the space created by a drilled hole in the body of the vertebrae. This is advantageous since drills are one of the tools of choice for orthopedic surgeons since they perform well in narrow spaces, are easy to control, and can be used to form bores quickly. The cylindrical bore produced by drilling also is desirable from the standpoint of avoiding crack propagation. The continuously curved surface produced by boring does not have sharp corners or intersections at which there may be stress concentration.

Of course, other than a cylindrical shape for the wall/retaining member 2330 is contemplated. Other shapes, derivable by those skilled in the art, may be utilized to prevent the wall/retaining member from pulling through the bone. For example, a "T"-shaped component could be utilized and has a more compact shape. Further, a convex surface may be formed without a full cylindrical shape.

The stabilizer cylindrical wall 2330 preferably has a reduced lead-in portion to ease insertion of the stabilizer 2200 into the bone. This is illustrated in FIGS. 23A and 23B in the form of a bullet tip-shaped nose 2361 with a tapered surface portion angled between a leading end and the surface 2303. As the stabilizer 2300 is advanced in its assembly path in the assembly direction, the tapered surface portion bears against the bone portion into which it is directed and progressively wedges that bone portion towards the spacer 2200. The nose 2361 is part of another reconfigurable body portion 2360. The reconfigurable body portion 2361 prevents backout of the stabilizer 2300 from the bone portion as well as preventing movement of the joined stabilizer and spacer relative to the bone portions in the assembly/advancing direction beyond the optimally identified location.

The reconfigurable body portion/nose 2361 is in the form of an expandable bulb 2362 at the leading end of the stabilizer cylindrical wall 2330. The reconfigurable body portion 2361 can take other forms such as a series of self-retaining clips or barbs deflected out into the bone. As illustrated in FIG. 23E and also in a similar arrangement in FIG. 19, the expandable bulb 2362 has one or more deflection gaps 2363 that bifurcate the reconfigurable nose 2361 into two or more parts. The deflection gap 2363 terminates at a relief bore 2364. The relief bore 2364 is preferably circular to minimize stress, thereby preventing material fracture. The material between the outer surface of the cylindrical wall and the relief bore defines hinged deflection walls 2365 that function as live hinge portions. The deflection walls 2365 are the portions of the bulb 2362 that undergo deformation, therein allowing separate repositionable body tabs 2366 to deflect about the hinge portion out to a diameter greater than that of the cylindrical wall 2330 and into bone, thereby retaining implant position. In the preferred embodiment, the two tabs 2366 expand to a diameter approximately 30% greater than the cylindrical wall diameter.

FIG. 24A is an illustration of an implanted spacer-stabilizer assembly 2401 with the tabs 2366 in the expanded and locked positions. The stabilizer wall 2330 in FIG. 24A is in a second position to which it has been moved, from a first position prior to entry into the bone portion BP1, wherein the stabilizer wall is aligned to initially enter the bone portion BP1. The spacer/cage 2200 is secured in the intervertebral space between the vertebral bodies 2410 (BP1), 2420 (BP2), with the spacer/cage 2200 and stabilizer in operative relationship with each other and the bone portions/vertebral bodies 2410, 2420. In this state, parts of each of the bone portion BP1 and the spacer 2200 are captive between the facing surfaces 2303, 2380. A portion of the vertebral body is cut away to illustrate the position of the stabilizers 2300 in the bone.

Figure 25A:
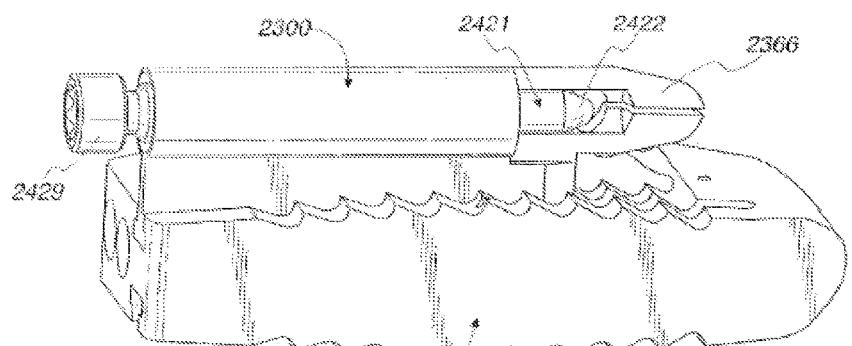
FIG. 25A is a perspective view of a spacer with a stabilizer docked therein, with a spreader partially seated within the stabilizer.
Figure 25B:
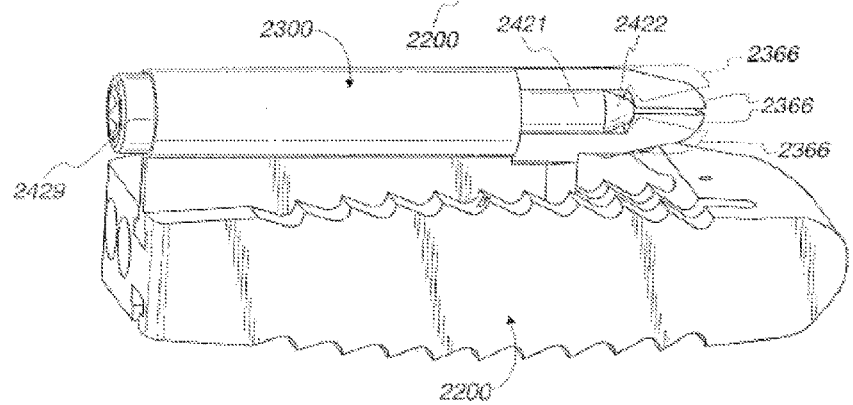
FIG. 25B is a perspective view of a spacer with a stabilizer docked therein, a spreader partially seated within the stabilizer wherein the nose of the spreader begins contact with the internal surface of the stabilizer tabs.

This stabilizer cylindrical wall 2330 has a central bore 2331 (FIG. 23A) terminating at, and contiguous with, the relief bore 2364. The bore 2331 has a central axis A. A portion of this bore, preferably at the trailing end, has threads 2332 or alternative connection mechanism, such as a bayonet connection, to securely contain a spreader 2421 (FIG. 24B) within the central bore 2331. The spreader 2421 has a diameter to occupy the central bore 2331 so that it will be guided in sliding movement therewithin. along the axis A. At the trailing end of the spreader 2421 are threads 2425, or other connection mechanism, to cooperate with the threads/connection mechanism 2332, wherein the spreader 2421 is pushed into and then advanced by threaded rotation into the bore 2331, as seen in the transition between FIGS. 25A and 25B. As an outer surface of a tapered nose 2422 at the leading end of the spreader 2421 abuts the internal surface of the tabs 2366 of the reconfigurable stabilizer 2300, as seen in FIG. 25B, further advancement of the spreader 2421 causes the reconfigurable body tabs 2366 to deflect, with the upper tab 2366 in FIG. 25B deflected outwardly into the surrounding bone, thereby securing the stabilizer 2300 in place. The tabs 2366 are consistently fully deflected when a shoulder stop 2426 abuts the stabilizer proximal face 2321 and the internal surfaces of the tabs 2366 rest on a shaft face 2423.

Located at the proximal/trailing end of the spreader 2421 is a drive head 2429 which in this embodiment is a drive pocket 2427 with a regular array of drive faces 2424 thereon. The pocket 2427 is configured to receive and intermesh with drive faces 2434 on a drive head 2433 of a spreader driver 2430 (FIGS. 24C and 24D) such that turning of the spreader driver 2430 through a hand-graspable driver handle 2431 will advance spreader 2421 into the stabilizer 2300 for locking. The leading end of the drive head 2433 may be configured for eased insertion into the drive pocket 2427 by using a taper 2432, radius, or other means and may also have a shoulder 2435 to block insertion consistently at a preferred depth.

To prevent unintended separation of the spreader driver 2430 from the spreader 2421, the drive head 2433 may incorporate an anti-separation feature. For example, in this embodiment the drive head 2433 may be bifurcated one or more times to create repositionable arms 2437 separated by one or more deflection gaps 2436. It is preferred that the arms 2437 elastically spring out to create an outside diameter of drive head 2433 that is slightly larger than that of the drive pocket 2427 so that, when inserted, a frictional fit of the drive head 2433 within the drive pocket 2427 is created with the arms 2437 wedged towards each other, wherein the spreader 2421 is not prone to unintentionally falling off yet is easily released when needed by the surgeon by intentional retraction of the spreader driver 2430. The spreader driver may include one or more alignment faces 2438 as illustrated in FIG. 24D to assist centering in the drill guide cylinder. In addition, handle 2431 may assume other hand fitting profiles such as a teardrop.

Different forms of instruments usable to install spacer/stabilizer assemblies into the affected intervertebral spaces are described below.

One embodiment of a spacer/cage inserter tool is shown at 2600 in FIG. 26A-28B. The tool 2600 is attached to the spacer body 2290 at an instrument attachment portion 2208 of the implant spacer/cage 2200. The inserter tool 2600 has a connection tip portion 2640 at the distal end of a guide bar body 2630 which, in this embodiment, is in the form of a threaded prong 2632 and a non-threaded prong 2631 for engagement in the threaded attachment holes 2215a, 2215b in the implant body 2290. The non-threaded prong 2631 resides in the one of the instrument attachment holes 2215a, 2215b of the implant spacer/cage 2200 that may be unthreaded. As noted above, the holes/bores 2215a, 2215b are both shown to be threaded, for reasons stated. However, one hole may be unthreaded. The threaded prong 2632 threads into the other, threaded hole 2215a, 2215b and holds the implant spacer/cage 2200 tight to an inserter face 2633. Together, both prongs 2631, 2632 serve to maintain consistent alignment of the spacer inserter instrument 2600 with the implant body 2290 thereby controlling the implant spacer 2200 during insertion. The connection tip 2640 portion may take other forms such as a bayonet connection or clamping arms. The instrument attachment portion 2208 is configured accordingly with a complementary structure.

The guide bar body 2630 (FIG. 26A) has a handle portion 2620 for user control over the inserter tool 2600. This handle 2620 has a graspable length that is preferably oriented to be angled, in one form on the order of 90 degree, to the central axis of the body 2630. The guide bar body 2630 houses a locking shaft 2614 illustrated in FIG. 26B. A threading spool 2611, here illustrated as an enlarged portion of the shaft is used to turn the locking shaft 2614, which terminates at the threaded prong 2632. As the threading spool 2611 is hand rotated, the threaded prong 2632 seats into one of the threaded attachment holes 2215a, 2215b on the implant, therein securing the implant spacer/cage 2200 to the inserter tool 2600.

The surgeon may then grasp the handle 2620 and guide bar body 2630 to control insertion of the spacer/cage 2200 into the intervertebral space. The nose 2400 of the implant spacer/cage 2200 is guided into a predetermined position between the vertebral endplates. The surgeon may choose to tap an impact fitting 2610 with a hammer to assist driving the implant spacer/cage 2200 into the intervertebral space. This impact force is transmitted from a transmission face 2613 to the adjacent face of the guide bar body 2630 then through inserter face 2633 to the spacer proximal face 2240. The proximal end of locking shaft 2614 may include a collar 2636 for engagement with an extended handle thereby providing the user greater control over the shaft.

The guide bar body 2630 may have one or more access apertures 2634 to facilitate viewing and/or cleaning. The length of the guide bar body 2630 is preferred to extend long enough that the handle 2620 can be grasped a comfortable distance outside of the patient's skin. The distal portions of the inserter tool 2600 are sized to pass through the internal channel formed by a tissue retractor.

Figure 26A:
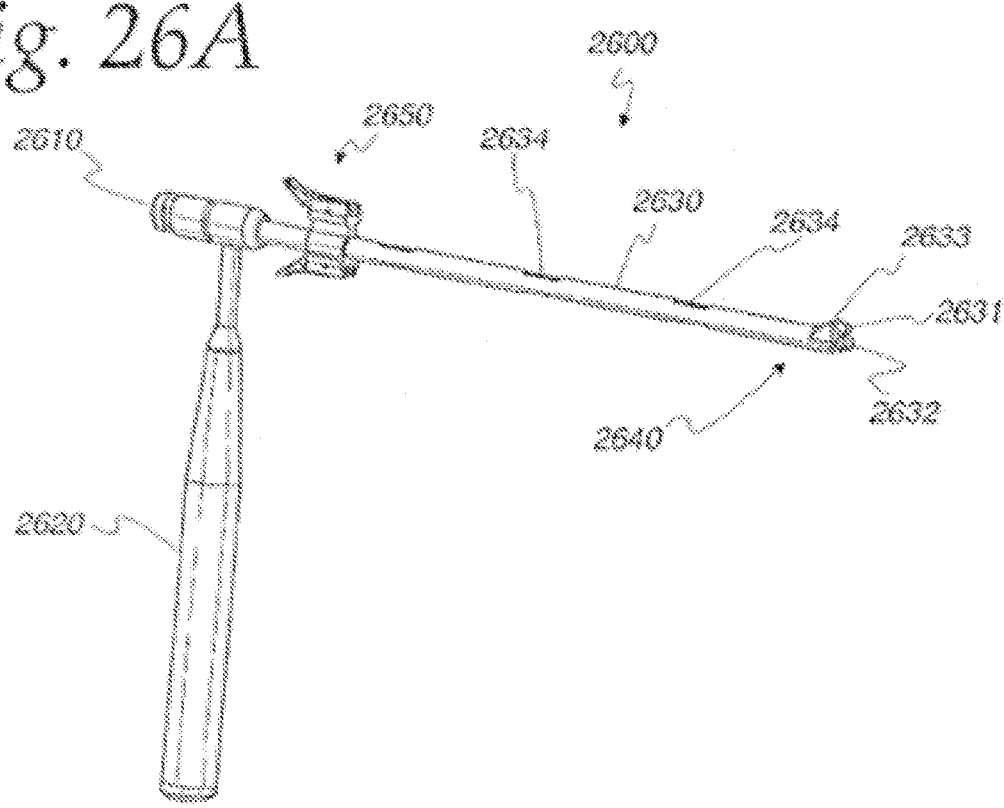
FIG. 26A is a perspective view of a spacer/cage inserter tool.
Figure 26B:
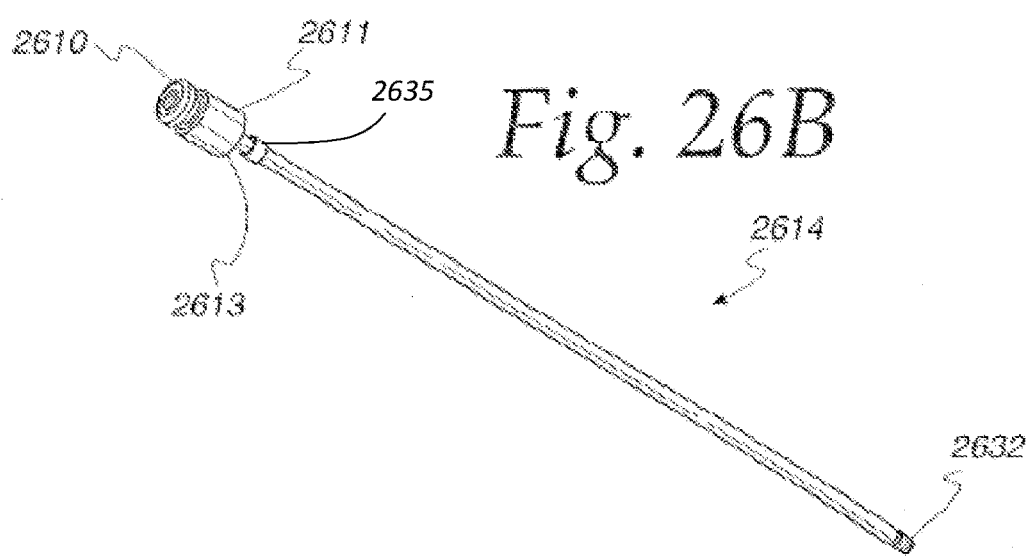
FIG. 26B is a perspective view of a locking shaft utilized inside the spacer/cage inserter tool for holding the spacer tight to the inserter tool.
Figure 26C:
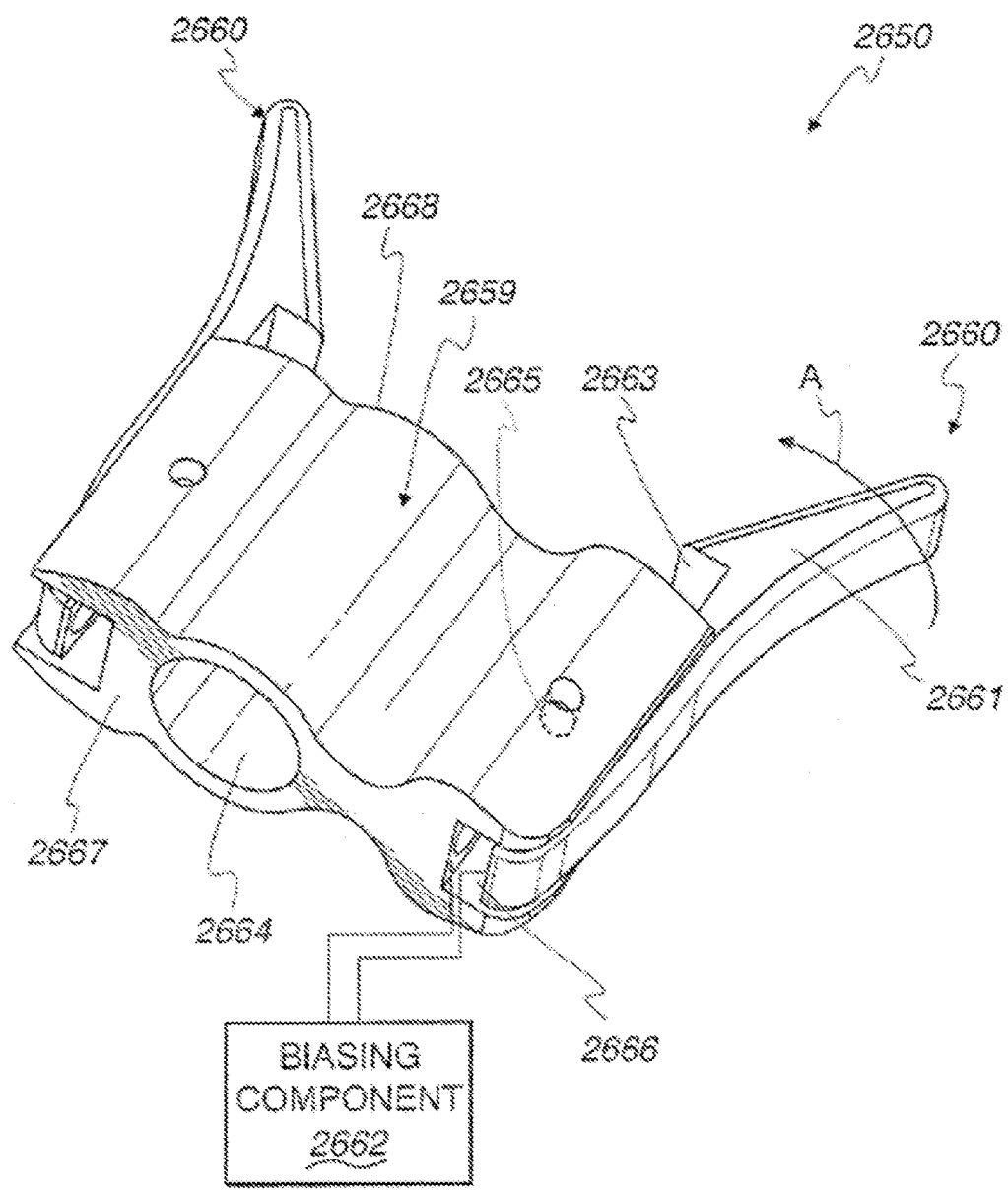
FIG. 26C is a perspective view of an accessory guide holder illustrating a locking mechanism.
Figure 26D:
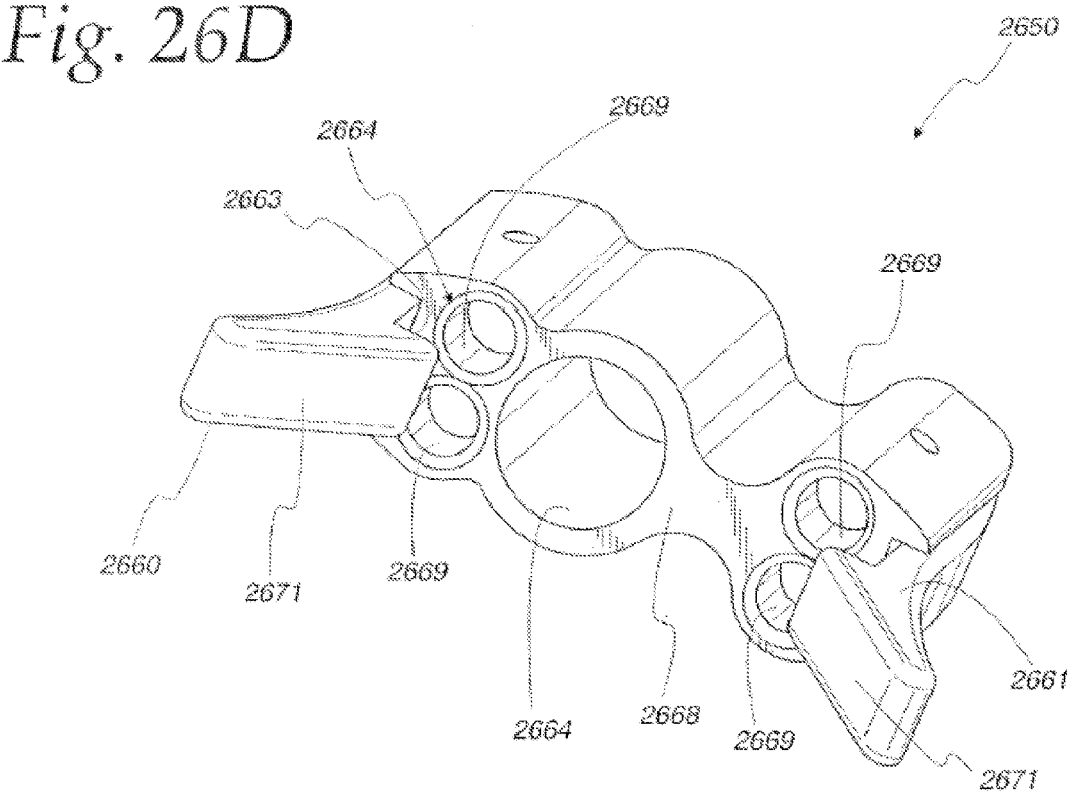
FIG. 26D is a perspective view of an accessory guide holder illustrating an opposing view of a locking mechanism.

The guide bar body 2630 may also cooperate with an accessory guide holder 2650, shown in FIGS. 26C and 26D, secured on or integrated into the outer surface of the body 2630 to hold and guide accessories/tools such as drill bits and drivers used in conjunction with the inserter 2600. The guide holder 2650 may have one or more accessory retainer portions 2660, with each of the two shown in the form of a spring-biased locking arm 2661. Each locking arm 2661 may have a resilient body integral with a main frame 2659 on the guide holder 2650 that springs toward a locking face 2663. This version is not shown in the drawings. FIGS. 26C and 26D illustrate, as a preferred alternative, a rigid locking arm 2661 movable about a pivot pin 2665. In a pivot gap 2666, a space is provided for a compression spring, or other biasing component 2662, to bias the locking arm 2661 in the direction of the arrow A to reposition the locking face 2663 thereon.

The accessory guide holder 2650 has a proximal face 2668 and a distal face 2667. Situated, preferably on at least the proximal face 2668, is an accessory positioner 2664 shown here in the form of a recess/aperture. In this embodiment, multiple, additional positioning recesses 2669 are provided. Some of the positioning recesses 2669 are shown as full, or blind, bores located different distances from the central axis of the guide bar aperture 2664 to reflect positioning required by accessories to be attached.

Figure 27A:
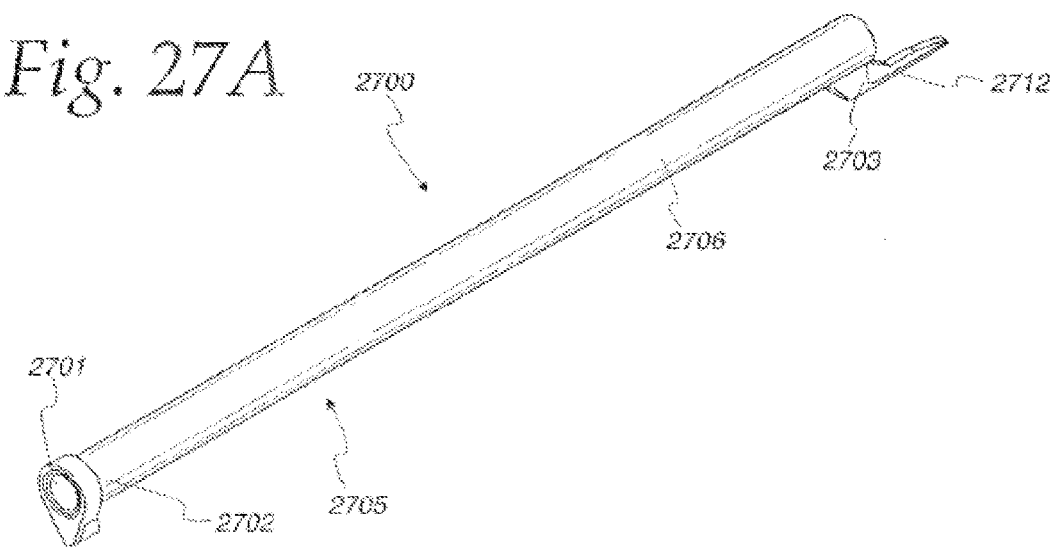
FIG. 27A is a perspective view of a drill guide.
Figure 27B:
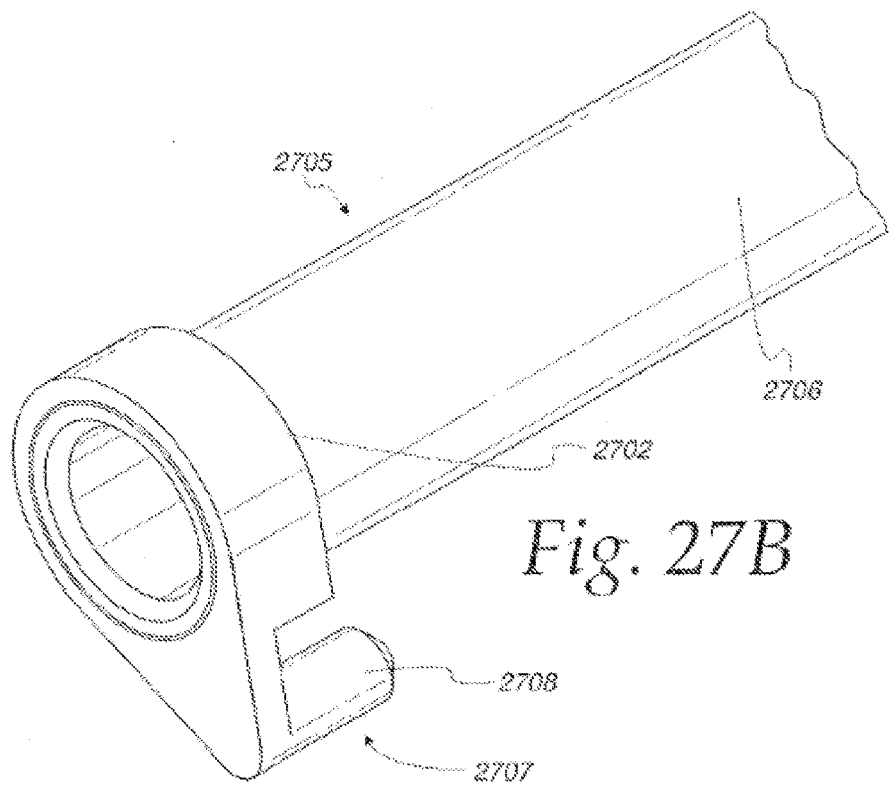
FIG. 27B is a perspective view of the proximal portion of a drill guide illustrating a positioner for docking with the spacer inserter tool.
Figure 27C:
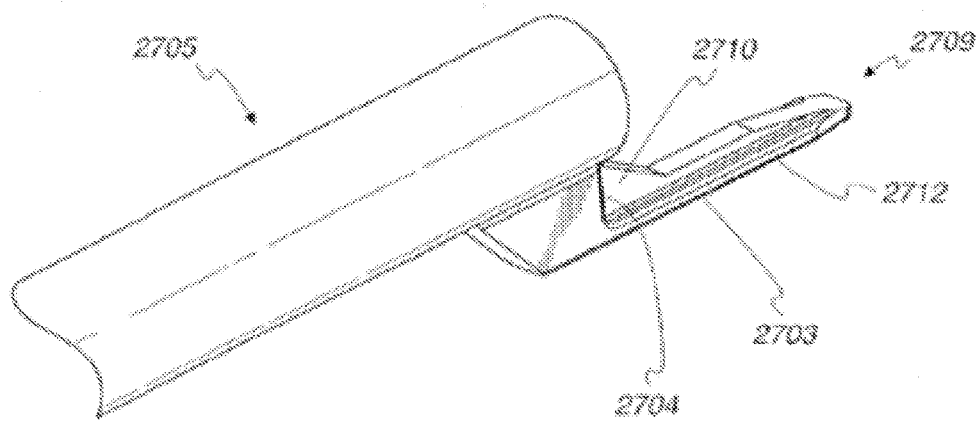
FIG. 27C is a perspective view of the distal portion of a drill guide illustrating the drill guide tip.
Figure 27D:
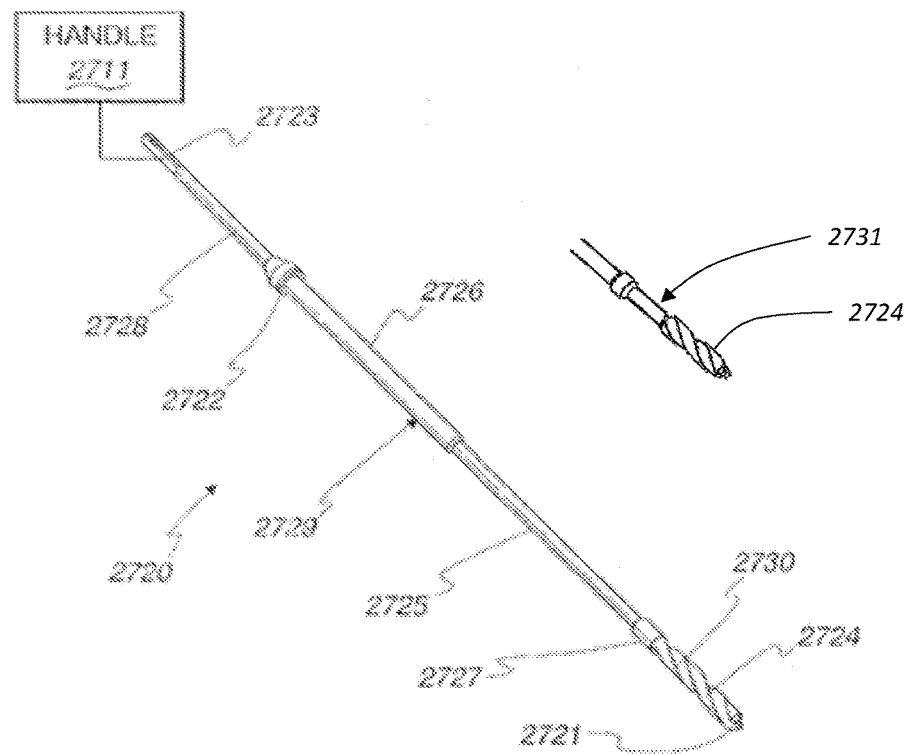
FIG. 27D is a perspective view of a drill configured for use with a drill guide and a partial view of a drill illustrating a collection recess.
Figure 27E:
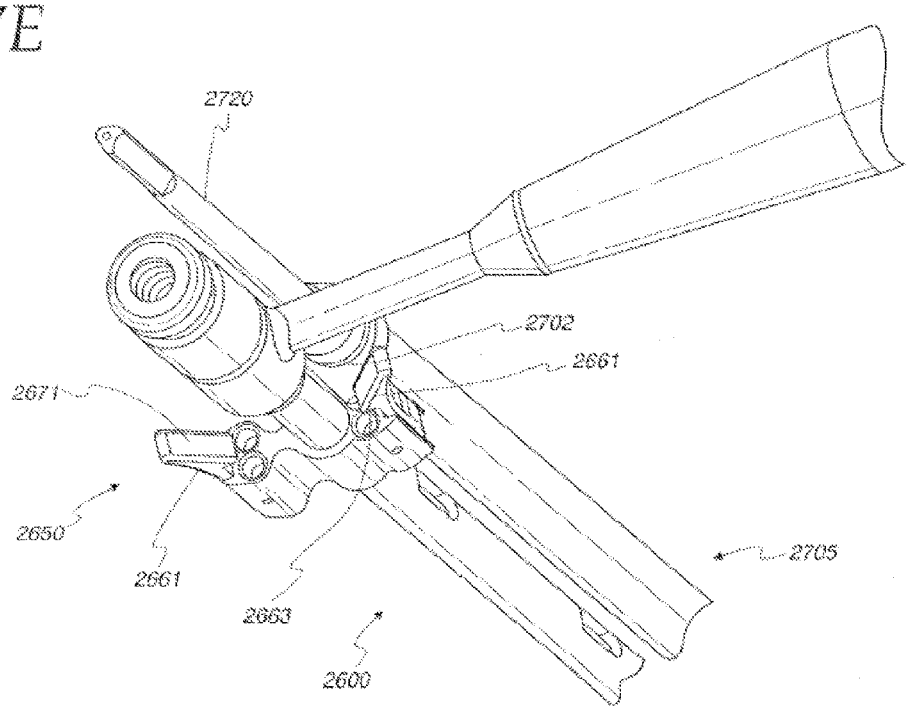
FIG. 27E is a perspective view of a drill guide body and drill docked with a spacer inserter tool.
Figure 27F:
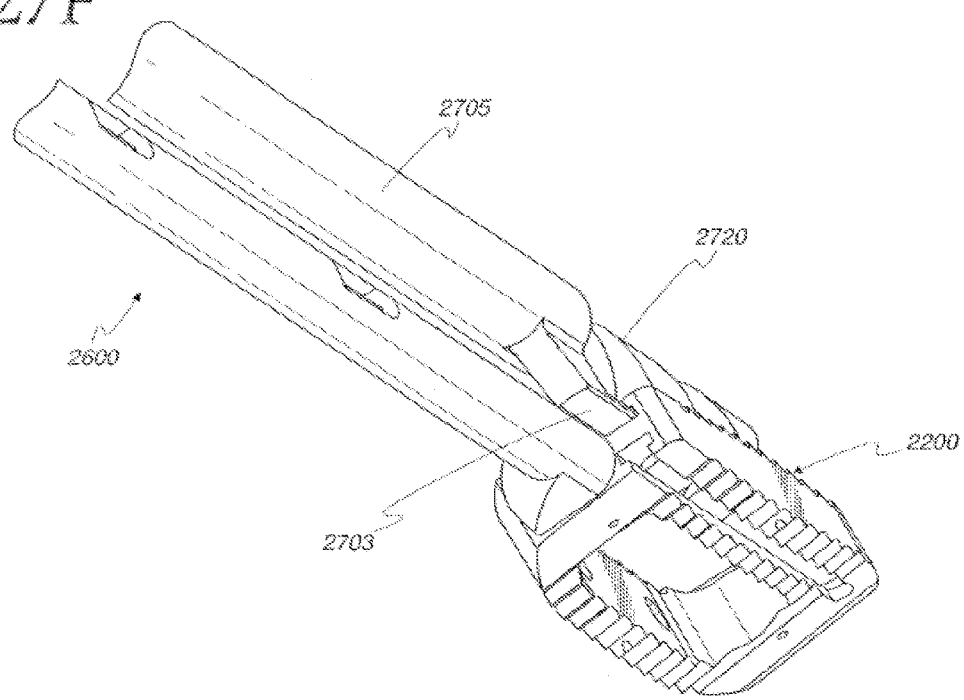
FIG. 27F is a perspective view of the distal portion of a drill guide-spacer inserter assembly illustrating the interface between a tool and spacer.
Figure 27H:
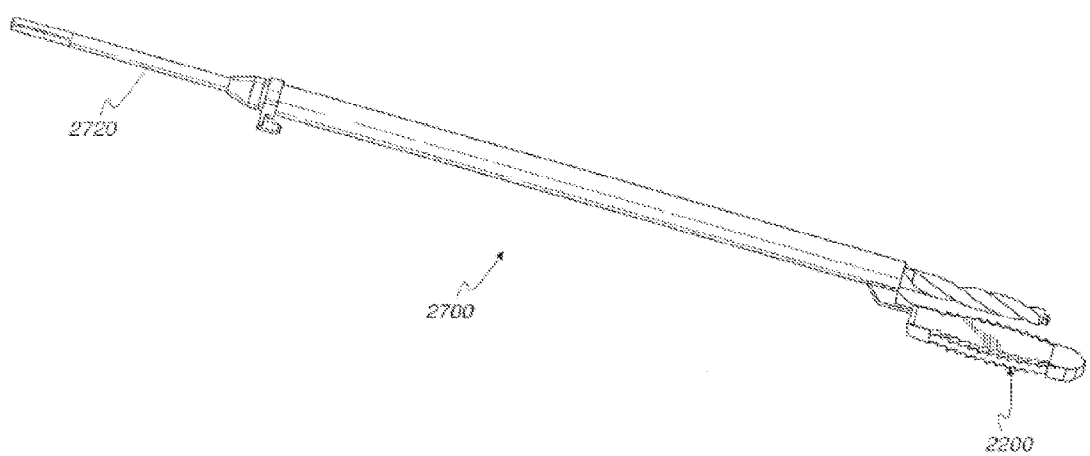
FIG. 27H is a perspective view of a drill guide docked to a spacer with drill fully inserted in the drill guide, with the spacer inserter tool hidden.

Illustrated in FIGS. 27A-27G are various exemplary instruments/components including a drill guide-drill assembly 2700, as shown in FIG. 27H. In one preferred form, the drill guide 2700 is interconnected with the spacer inserter tool 2600 to create an interdependent assembly that will improve stability of the drill guide 2700 and accuracy in placement of the spacer/cage 2200. This combined drill guide-spacer inserter assembly is shown at 2790 in FIG. 27G. It is possible, although less preferred, that the spacer inserter tool 2600 and the drill guide-drill assembly 2700 are not interconnected. In this configuration, the drill guide 2700 may have its own handle 2711 depending from a proximal end. FIG. 27H illustrates the drill guide-drill assembly 2700 without the spacer insert tool 2600.

A preferred embodiment of the drill guide 2700 is illustrated in FIGS. 27A-27C. A drill guide body 2705 spans between a drill guide tip 2703 and a drill guide shoulder 2702. The drill guide body 2705 has an outer drill guide wall 2706, which in this case defines a drill guide cylinder 2701 to receive and guide a drill 2720 as shown in FIG. 27D. Although the wall 2706 is illustrated as a continuous cylinder, the wall 2706 may be discontinuous. For example, the wall 2706 may be in the form of a plurality of tabs extending from the drill guide body 2705 yet still functioning to contain and guide the drill 2720. Preferably at the proximal end of the drill guide body 2705, although it could be positioned elsewhere, the drill guide shoulder 2702 is provided. This shoulder 2702 interfaces with a drill guide stop 2722 on the drill 2720 to stop penetration of the drill 2720 into the bone at a predetermined depth. Also, preferably at the proximal end of the drill guide body 2705 is a positioner 2707 shaped to complement the accessory positioner 2664 on the accessory guide holder 2650. The positioner 2707 in this embodiment is in the form of a positioning boss 2708 configured to fit in one of the positioning recesses 2669.

The distally located tip 2703, seen clearly in FIGS. 27A and 27C, is configured in profile and size to complement the spacer's stabilizer anchor 2245, in this case to be slid into one of the spacer channels 2255, 2265 with which it has a complementary shape. The tip 2703 has a "T"-shaped configuration much like the stabilizer's spacer anchor 2370 in FIG. 23A. Similarly, the drill guide tip 2703 has a flat track or base wall 2712, a web wall 2710, and a base nose 2709. The base nose 2709 is tapered and radiused much like the stabilizer base wall nose 2311 to simplify insertion into one of the channels 2255, 2265. The web wall 2710 extends upright from the base wall 2712 and is integrated into, or otherwise attached to, the drill guide body 2705. The tip 2703 also has a drill guide stop 2704, here in the form of a ridge extending out from the web wall 2710, to limit overinsertion once the stop 2704 abuts the proximal face 2240.

In a preferred embodiment, as shown most clearly in FIG. 27D, the drill 2720 has an elongate body 2729 with several features thereon. The proximal end of the drill 2720 has a drive shaft 2728 with drive faces 2723 thereon defining a polygonal outer drive surface. The drive faces 2723 are configured to be directed into a complementary shaped receptacle on the handle 2711. Alternatively, the drive shaft could be configured in the shape of a handle. The drill stop 2722 is configured in this case to abut the drill guide shoulder 2702 when the drill 2720 has reached its predetermined depth. The body 2729 may also include one or more radially enlarged, cylindrical alignment faces. This embodiment has a proximal alignment face 2726 and a distal alignment face 2727. When the drill body 2729 is situated within the drill guide wall 2706, these alignment faces 2726, 2727 are sized to have a diameter slightly less than the inner diameter of the drill guide cylinder 2701 to maintain alignment and minimize wobble of the drill 2720 during use. A base region 2725 is a recessed area in the body which may be configured to separate the alignment faces 2726, 2727 and for collection of bone chips as the drill 2720 engages with and removes bone. In other embodiments, this collection recess 2731 may be directly adjacent cutting flutes 2724 as shown in the partial view of FIG. 27D. At the distal end of the drill 2720 is a cutting tip 2721 which is preferably tapered back to engage the bone from a starting point. Cutting flutes 2724 extend back helically from the tip 2721 to carry bone chips away from the cutting tip 2721. The flutes 2724 and tip 2721 have sharp cutting faces 2730 on edges thereon to ease cutting through bone.

FIG. 27E is a close-up view of the proximal end of the drill guide-spacer inserter assembly 2790 of FIG. 27G. As the drill guide tip 2703 is inserted and translated into one of the channels 2255, 2265, the stop 2707 of the drill guide 2700 will approach the accessory positioner 2664. For this embodiment, the leading end of the positioning boss 2708 will align with a predetermined positioning recess 2669 and eventually be moved therein. As the leading end of the drill guide shoulder 2702 contacts the sloped entry face 2671 of the locking arm 2661, the locking arm 2661 will be cammed back until the trailing face of the drill guide shoulder 2702 passes and then is captured by the locking face 2663 once the locking arm 2661 springs back into position. In this state, the drill guide tip 2703 is fully seated in a channel 2255, 2265 and the drill guide stop 2704 abuts the proximal face 2240 of the spacer/cage 2200. The drill guide 2700 is thus fully docked to the spacer inserter tool 2600.

Tools to measure the anatomical void where a spacer will be placed may be used to determine correct spacer size. For example, trial spacer 3300 (FIG. 38A) comprises a trial insert 3302. The trial insert 3302 comes in various sizes and are generally the same shape of the implants offered. The surgeon slips various trial inserts in the void until an appropriate size is determined. The trial spacer includes a trial rod 3303, a trial handle 3301 for controlling the trial spacer 3300 within the surgical corridor, and a pod 3304 for connection purposes or for tapping with a surgical hammer. In some cases an extension handle, such as illustrated in FIG. 38B, may be utilized to extend the reach of an instrument. It includes a grip portion 3400 and a pod clasp 3401 which may be used for example to slide over and connect with the handle of another instrument by way of pod 3304. Clasp 3401 may include a retention mechanism, here illustrated in the form of a ball detent.

The surgical technique begins by preparing the patient using standard pre-op procedures. The patient is positioned on the operating room table consistent with the surgical approach required to gain disc space access. For example, the spacer illustrated in FIG. 9 is adapted best for an anterior surgical approach wherein the patient would be positioned supine on the operating table for an ALIF procedure. A surgical technique for a lateral approach is described below, as the spacer-stabilizer assembly of FIG. 24A is well suited to be inserted laterally. Clearly, the surgical technique can be easily adapted for other approaches.

For the lateral approach, the patient is typically positioned sidelying on the contralateral side of the incision site. EMG monitoring may be useful during surgery to help the surgeon steer clear of nerves near the surgical path.

Incisions from the lateral side, to open access to the surgical site, are made. Tissue dilators and/or retractor systems may be used to access the affected disc space along with access lighting. Using instruments such as shavers, curettes, and rongeurs, the diseased disc material is removed and the endplates are prepared and roughened to expose bleeding bone. Disc space sizing instruments, such as trial spacers and/or imaging, may be used to correctly size the spacer/cage 2200 and stabilizers 2300 required for the patient. The spacers and stabilizers may be provided in one or more surgical kits in a variety of sizes to suit the patient's anatomy along with instruments described above. This sizing may include not only measuring the gap between endplates, but also angles between the endplates, and the overall footprint size of the endplates.

The dimensions of the spacers 2200 of this embodiment will generally range from 7 mm to 17 mm in height (h), between 35 mm and 65 mm in length (L), and 11 mm to 21 mm in width (W). The angle between the superior and inferior endplate facing surfaces of the spacer generally ranges from 0-12 degrees.

The selected spacer is chosen from the surgical kit and just before or after attachment to the spacer inserter tool 2600 (as previously described), the spacer opening 2232 may be packed with a chosen graft material. The inserter tool 2600 with the selected spacer attached is then guided through the incision, down the corridor created by the retractor, until it has reached its predetermined position in the intervertebral space. The placement of the implant may be checked by imaging and readjusted. Markers placed in the marker housings 2285 will show on imaging therein, assisting the surgeon in properly positioning the spacer. Unless preassembled, the tip 2703 of the drill guide 2700 is then guided along the guide bar body 2630 of the spacer inserter tool 2600 and directed into one of the channels/tracks 2255, 2265 of the spacer/cage 2200. The drill guide 2700 is translated until the drill guide 2700 abuts against the spacer/cage 2200 and/or the drill guide shoulder 2702 is captured under the locking face 2663. The drill guide tip 2703 is preferably configured in a "T" shape sized to easily slide into the spacer's channel 2255, 2265 with minimal play.

A drill 2720 of predetermined diameter is inserted into the cylinder 2701 of the drill guide 2700. The surgeon, utilizing hand force or power on the drive faces 2723, creates a bore/channel into the wall of the vertebrae by advancing the drill 2720 into the drill guide cylinder 2701 and vertebral body until the drill stop 2722 on the drill 2720 abuts the drill guide shoulder 2702, indicating that the full predetermined depth of the drill has been reached. The drill 2720 and guide 2700 are then removed. Locking the drill guide 2700 to the channel/keel track 2255, 2265 assures precise control over the starter hole position and angulation therein, assuring easy insertion of the stabilizer cylindrical wall 2330 later.

The stabilizer 2300 is now attached to a stabilizer inserter 2800, illustrated in FIGS. 28A and 28B. The stabilizer inserter 2800 has an elongate tube or shaft body 2801 with an insertion tip 2802 at a leading end. The insertion tip 2802 has a reduced diameter leading prong 2803 sized to occupy the central bore 2331 of the stabilizer cylindrical wall 2330. The prong 2803 assists to control the stabilizer 2300 during insertion. Stepped back from the prong 2803 is a threaded section 2804 of the insert 2800 configured to engage the internal threads 2332 of the stabilizer bore 2331. A stop 2805 abuts the proximal face 2321 of the stabilizer 2300 when the inserter 2800 is fully advanced and seated in the stabilizer 2300. The trailing end of the stabilizer inserter 2800 has an impact surface 2807 for tapping the stabilizer 2300 into position. A graspable handle 2806, in a preferred embodiment, has an enlarged tip 2809 upon which the surface 2807 is defined and which will contact the impact face 2612 of the spacer/cage inserter tool when the stabilizer is fully seated thereby preventing over penetration of the stabilizer 2300.

Utilizing the handle 2806 of the stabilizer inserter instrument 2800 to steer and advance down the retracted surgical corridor, the base nose 2311 at the leading end of the stabilizer is inserted into a keel track channel 2255, 2265 and advanced in a first direction in a linear path by the surgeon, tapping at the trailing end of the stabilizer inserter instrument 2800 into the vertebrae until the stabilizer 2300 reaches the stabilizer stop 2276 and achieves an operative relationship with the spacer 2200. As the stabilizer is advanced, the leading edge 2340 cuts through the bone portion between the drilled bore/channel and the adjacent surface on the bone portion. Alternatively, a complementary slot for receiving the web 2320 can be pre-formed in the bone portion, making the sharp leading edge 2340 potentially unnecessary. Even if this slot is pre-formed, the sharp leading edge 2340 may still perform a valuable function in aligning/guiding the web 2320 at the slot. The self-retaining tabs/barbs 2350 will prevent backout of the stabilizer 2300 from the spacer channels 2255, 2265. The stabilizer inserter 2800 is then unthreaded from the stabilizer 2300 and removed.

A threaded spreader 2421, as shown in FIG. 24B, is then attached to the spreader driver 2430 in a first position and advanced by being turned around its lengthwise axis into the stabilizer 2300 central bore 2331 into a second position, wherein the spreader is fully seated. FIG. 25B illustrates a spacer/cage 2200 with a stabilizer 2300 inserted therein. The spreader 2421 is partially seated within the stabilizer 2300 wherein the nose 2422 of the spreader 2421 begins contact with the internal surface of the stabilizer tabs 2366, as shown in FIG. 25B. FIG. 25A is a similar illustration, but the spreader 2421 has yet to contact tabs 2366. A portion of the stabilizer is resected for viewing purposes.

The reconfigurable stabilizer 2300 is fully secured when the spreader 2421 is fully seated, and changed from this first state by causing tabs 2366 to be deflected from a first relaxed position into a second position and forcibly into the surrounding bone, representing a locked state for the stabilizer. The bone-engaging tabs 2366 produce a localized compression that reconfigures the adjacent bone so as to further enhance compression between that bone portion and the spacer. The spacer stabilizer assembly 2400, situated within the partially resected vertebrae and with stabilizer tabs 2366 fully deployed, is illustrated in FIG. 24A. The spreader driver 2430 may now be removed. Following the steps above, bores for other stabilizers can be drilled and other stabilizers can be inserted and locked into position in like manner to engage both bone portions 2412, 2413. The spacer inserter tool 2600 is then removed. The wound closure procedure may then be initiated. The instrumentation preferably functions by movement along an axis/line coincident with the implant insertion axis, thereby minimizing the incision size.

The joined spacer/cage 2200 and stabilizer 2300 implant may be removed by unscrewing and therein unlocking the spreader(s) 2421 and removing it. The spacer/cage 2200 and stabilizer 2300 implant can then be removed by reattaching the inserter tool 2600 and pulling opposite to the path/line of insertion. If necessary, the stabilizer 2300 may be backed out from the channels/tracks 2255, 2265 by shearing the spacer track material, thereby releasing the tabs/barbs 2350.

Insertion and removal of the spacer and stabilizer is affected by movement of those components in a single plane, and in a preferred form in parallel lines, whereby the overall procedure is minimally invasive.

One or more surgical kits may be provided containing all implants and instruments required to perform the surgery. These kits may include implants such as various sized spacers, stabilizers, and spreaders. They may also include instruments that directly interface with these implants such as spreader drivers, spacer inserter tools, stabilizer inserters and drill guides. In addition, the kits may contain scalpels, drills, guide wires, dilators, retractors, lighting sources, and instruments for disc preparation such as shavers, curettes, and rongeurs. A kit containing a nerve monitoring system may also be provided.

In the preferred embodiment, the distance from the central axis of the drilled hole in the vertebral bodies to the nearest spacer opposing surface is on the order of 0.5 mm greater than the distance between the central axis of the stabilizer cylindrical wall and the nearest spacer opposing surface that produces a captive force. In other words, the first surface 2380 of the base wall 2310 is spaced from the axis A of the wall 2330 a distance that is less than the distance between the surface 2266 bounding the channel 2255 and the central axis of the drilled bore/channel in the bone portion. This discrepancy in distance causes there to be approximately 0.5 mm movement that preferably causes compression of parts of the spacer and bone portion between the cylindrical wall surface 2303 and the opposing surface 2380 that is progressively developed as the spacer and stabilizer are moved from their pre-assembly relationship into their operative relationship. This compression force resulting from the cooperative interaction of the stabilizer, bone portion, and spacer, as the spacer and stabilizer are placed into operative relationship with each other and the bone portion, assures that the vertebral body/bone portion is held tightly against the adjacent interbody/spacer surface, therein, apart from imparting stability, improving the opportunity for a successful fusion. Also, by keeping the cylindrical wall relatively close to the endplate (approximately 5 mm above the endplate), by applying a bearing force over a majority of the end plate extent where the stabilizer overlies the same, the cylindrical wall is securely kept in the hard endplate bone. If the cylindrical wall is too deep into the vertebrae (web wall is too tall), the cylindrical wall will reside in the softer bone of the vertebral body and therein is more likely to deform the softer bone, potentially allowing the implant to loosen.

Biomechanical testing of the spacer stabilizer assembly 2400 revealed static torsion of 36 Newton Meters with 9 degrees rotation. This is roughly triple the results of a pedicle screw corpectomy model. Other performance measures of this assembly include static yield compression of 4190 Newtons, and an ultimate compression strength of 4798 Newtons. Stability was demonstrated in all planes of movement. This positive fixation results instantaneously and is only further enhanced by eventual bone ingrowth.

The bodies 2290 of the spacers in these embodiments are preferably manufactured using biocompatible polymer such as PEEK (polyetheretherketone) or similar materials, but could be made using metals such as titanium or titanium alloys such as Ti64, or stainless steel alloys, or other biocompatible materials. The stabilizer is preferably manufactured using these metals although strong polymers or composites are also usable. Materials discussed and disclosed earlier may also be used. The implant may utilize coatings such as hydroxyapatite or other surface treatments to assist surface bone adhesion to the implant.

The spacer is shown with a symmetrical configuration for insertion selectively in either of opposite directions between vertebrae and in an inverted orientation.

The spacer, such as the form illustrated in FIGS. 22A-22D, and the stabilizer, such as the form illustrated in FIG. 23A, may be inserted utilizing an alternative form of spacer/cage inserter 3000 illustrated in FIGS. 29-33. The inserter tool 3000 is attached to the spacer body 2290 at an instrument attachment portion 2208 of the implant spacer/cage 2200. The spacer inserter 3000 has a connection tip portion 2640 at the distal end of a guide bar body 2630 which, in this embodiment, the connection tip portion is also in the form of a threaded prong 2632 and a non-threaded prong 2631 for engagement in the attachment holes of implant body 2290 illustrated in FIG. 22A as 2215a, 2215b. These holes/bores 2215a, 2215b are both shown to be threaded for reasons stated earlier although one may be unthreaded. The non-threaded prong 2631 resides in the one of the instrument attachment holes 2215a, 2215b of the implant spacer/cage 2200 that may be unthreaded. The threaded prong 2632 threads into the other threaded hole 2215a, 2215b and holds the implant spacer/cage 2200 tight to an inserter face 2633. Together, both prongs 2631, 2632 serve to maintain consistent alignment of the spacer inserter instrument 3000 with the implant body 2290 thereby controlling the implant spacer 2200 during insertion.

The connection tip 2640 portion may take other forms such as a bayonet connection or clamping arms or non-circular boss end. The instrument attachment portion 2208 is then configured with a structure complementary to these other forms to impart control on the spacer 2200.

Figure 29:
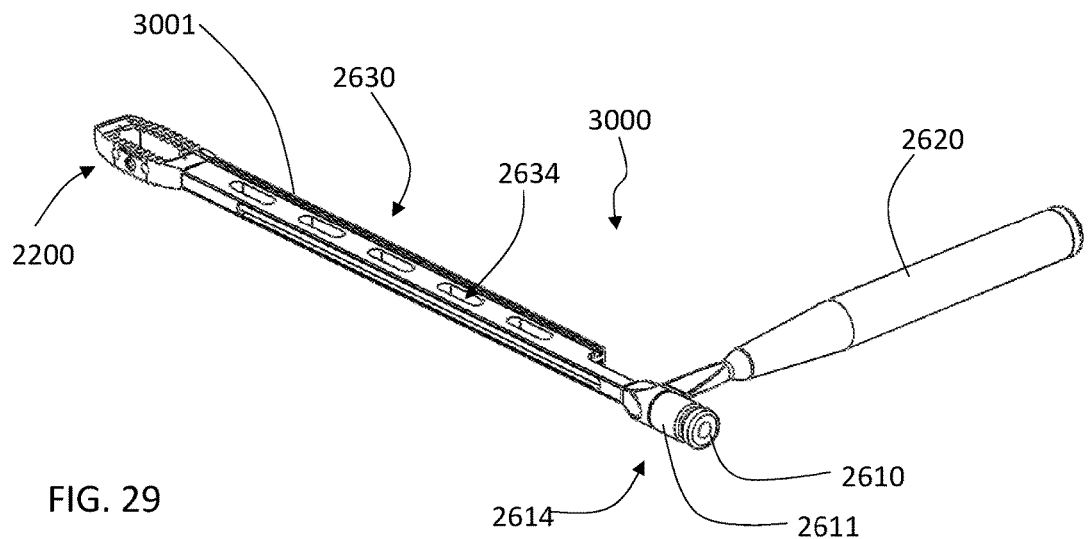
FIG. 29 is a perspective view of a preferred embodiment of an assembly of a spacer, an alternative spacer inserter, and locking shaft.
Figure 30:
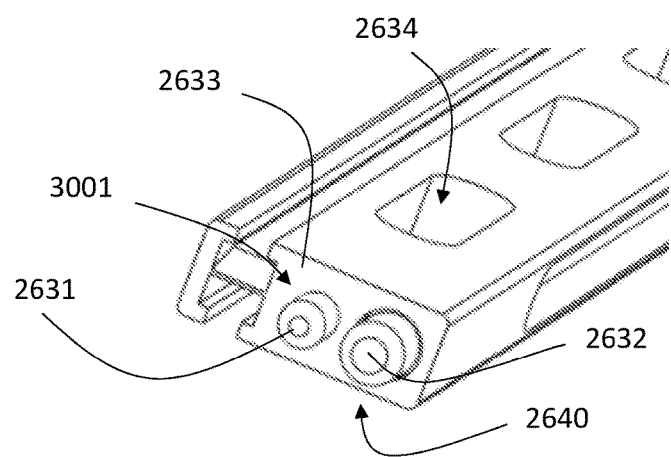
FIG. 30 is a close-up perspective view of the end of a spacer inserter.

The guide bar body 2630 may include a handle portion 2620 for user control over the inserter tool 3000. This handle 2620 has a graspable length that is preferably oriented to be angled, in one form on the order of 90 degrees to the central axis of the body 2630. In some embodiments, the handle portion may be extended proximally on the guide bar body 2630 by stem section 2637 to provide improved access. The guide bar body 2630 houses a locking shaft 2614 (FIG. 26B) within a locking shaft aperture 3005 as illustrated in FIG. 29. A threading spool 2611, sized and shaped for finger advancement, is provided for the user to advance the locking shaft 2614, which terminates at the threaded prong 2632 as illustrated in FIG. 30 (threads not shown). One or more alignment face 2635 may reside on locking shaft 2614 for alignment within the guide bar body 2360. As the threading spool 2611 is hand rotated, the threaded prong 2632 seats into one of the threaded attachment holes 2215a, 2215b on the implant, therein securing the implant spacer/cage 2200 to the inserter tool 3000. The non-threaded prong 2631 seats in the remaining attachment hole to prevent rotation of the implant relative to the guide bar body.

The handle 2620 and guide bar body 2630 may be used by the surgeon to control insertion of the spacer/cage 2200 into the intervertebral space. The nose 2400 of the implant spacer/cage 2200 is guided into a predetermined position between the vertebral endplates. An impact fitting 2610 on the proximal end of locking shaft 2614 may be tapped with a hammer to assist driving the implant spacer/cage 2200 into the intervertebral space. This impact force is transmitted from a transmission face 2613 of locking shaft 2614 to the adjacent transmission face 3006 of the guide bar body 2630 then through inserter face 2633 to the spacer proximal face 2240.

The guide bar body 2630 may have one or more access apertures 2634 along the length of body 2630 to facilitate viewing and/or cleaning. The length of the guide bar body 2630 is preferred to be of sufficient length wherein an attached handle 2620 can be grasped a comfortable distance outside of the incision above the patient's skin. The distal portions of the inserter tool 3000 are sized to pass through the internal channel formed by a tissue retractor or surgical tube.

Figure 31:
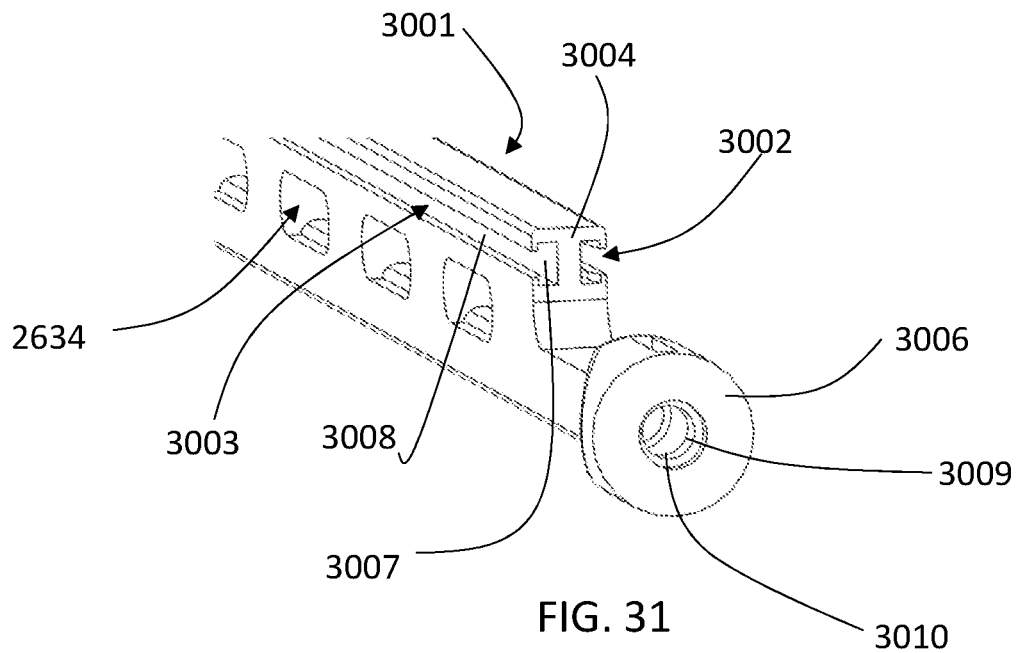
FIG. 31 is a partial perspective view of the proximal end of a spacer inserter body.
Figure 32:
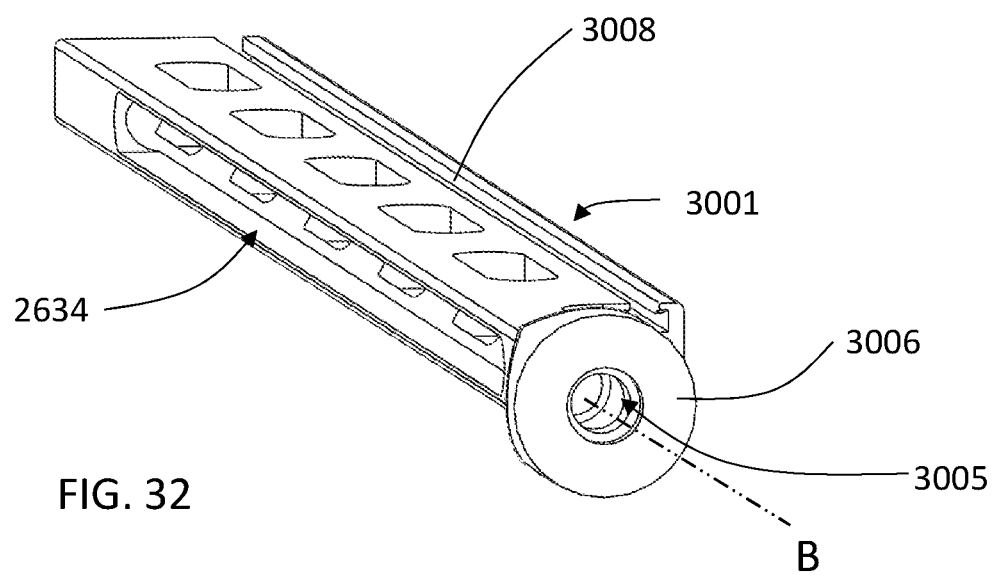
FIG. 32 is perspective view of the proximal end of a spacer inserter body.
Figure 33:
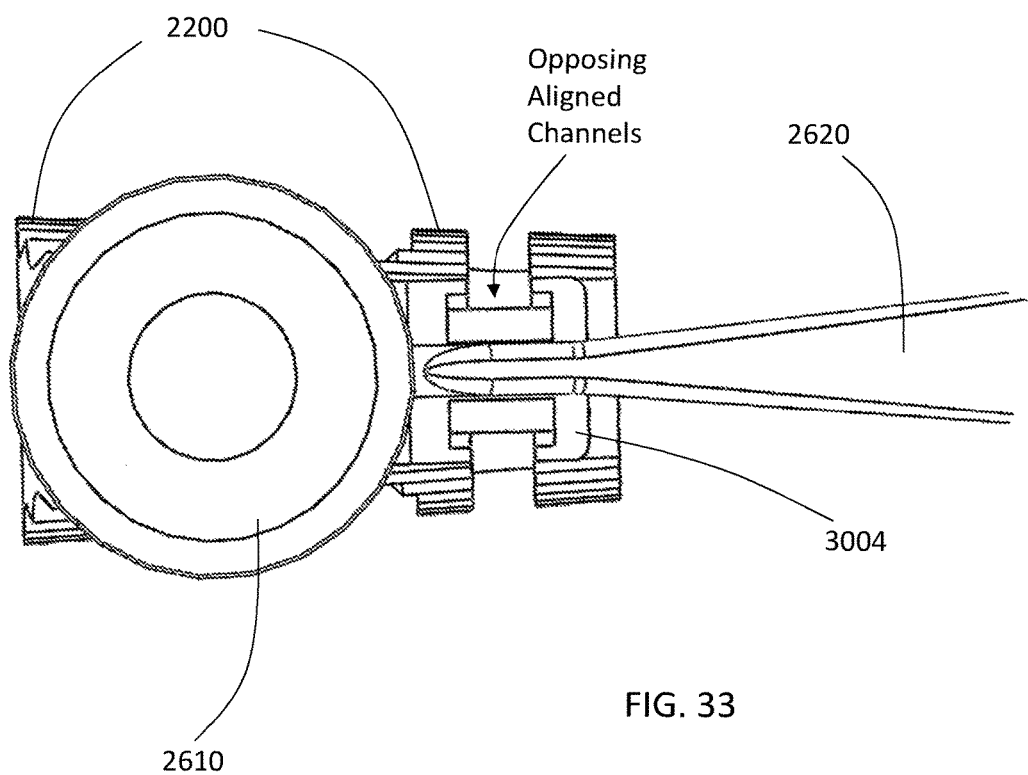
FIG. 33 is a proximal end view of the inserter illustrated in FIG. 29 with attached spacer. The view illustrates alignment of the channels from instrument to implant (longitudinal guide of inserter to anchor portion of spacer).
Figure 34:
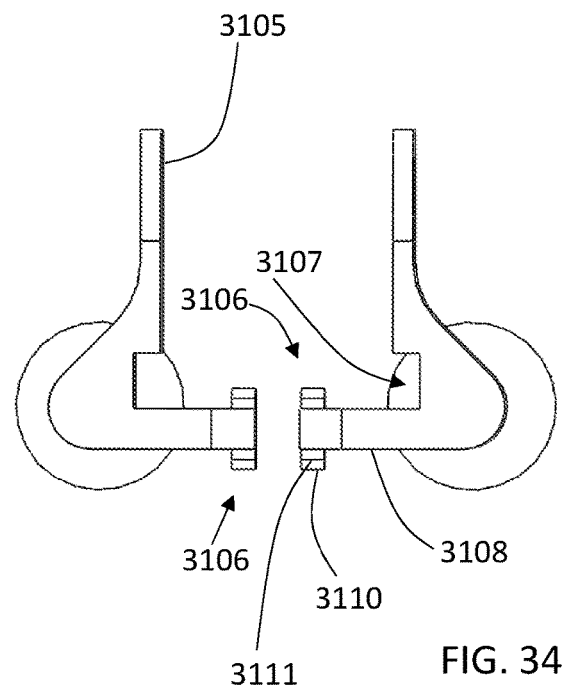
FIG. 34 is a distal end view of opposing graft blocks.
Figure 35:
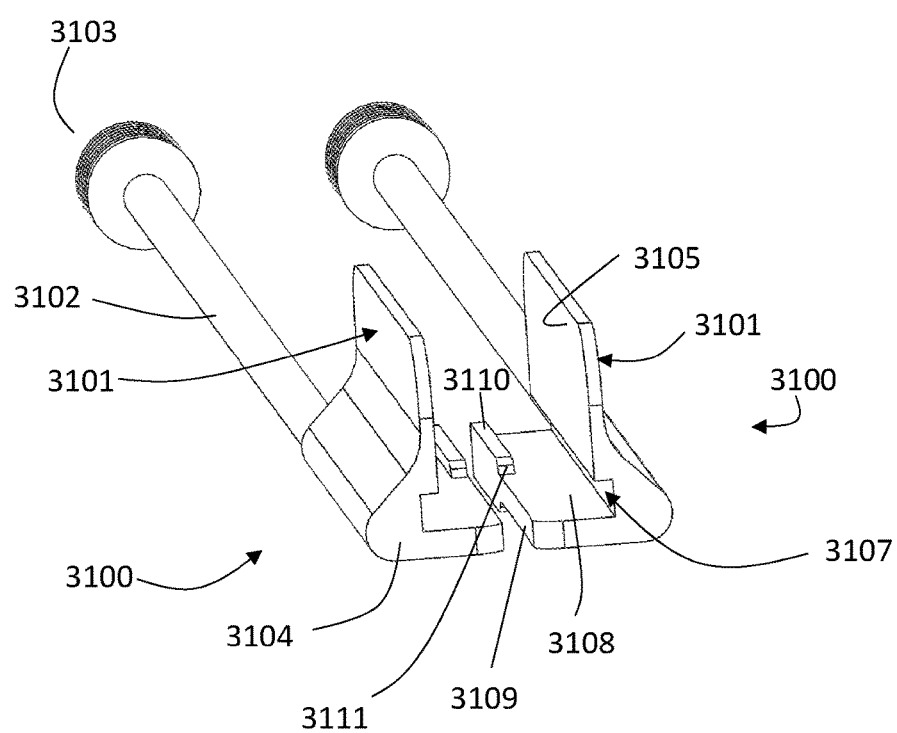
FIG. 35 is an end perspective view of opposing graft blocks.

The guide bar body 2630 illustrated in assembly in FIG. 29, includes a longitudinal guide 3001 illustrated in FIG. 31 in the form of opposing T-shaped channels 3002 and 3003. The T-shaped channels 3002, 3003 are defined by guide walls 3007 with guide surfaces 3008 on each guide wall 3007. The profile of the T-shape may vary in width along the length of the channel and entry into the channels from a proximal or distal end may be sloped to provide eased entry into or out of the channel by other implant or instrument parts. Channels 3002 and 3003 are preferably configured of similar profile and dimension and align with spacer channels 2255 and 2265 when inserter 3000 is secured to spacer 2200 as illustrated in FIG. 29. FIG. 33 further illustrates the alignment between channels in the instrument and implant. Like spacer channels 2255 and 2265, it is preferred channels 3002 and 3003 are configured to capture implant components and instruments for linear sliding engagement down guide bar body 2360 and into spacer channels 2255 and 2265 to assure alignment of additional implants and instruments with the spacer and bone portions. For example, the spacer anchor 2370 (FIG. 23A) of stabilizer 2300 may be inserted at proximal channel face 3004 of inserter 3000 into channels 3002 and 3003. In this configuration, stabilizer 2300 and instruments such as drill guides are guided from the entrance of the incision down to their pre-determined location within the body therein avoiding the challenges of aligning these structures deeper within the incision site when surgical vision is compromised by surrounding tissue. At the proximal end of the inserter body 2630 is inserter transmission face 3006 positioned to transfer impact forces applied by a hammer to impact fitting 2610, as well as fixation forces by transmission face 2613 of locking shaft 2614 when locking spacer 2200 to inserter 3000. An elongated locking shaft aperture 3005 extends the length of guide bar body 2630 and is sized to house locking shaft 2614. The shaft aperture is defined by shaft aperture walls 3009 and shaft aperture surface 3010.

The accessory guide holder 2650, illustrated in FIGS. 26C and 26D is unnecessary in this embodiment (FIG. 29) because the longitudinal guide 3001 serves this function of holding and guiding the stabilizer 2300 and other instruments from a proximal position near the incision opening to predetermined surgical locations.

Illustrated in FIGS. 34-38 are exemplary instruments configured for use with inserter tool 3000. One or more graft blocks 3100 may be utilized to secure bone graft or other bone substitutes within opening 2232 of spacer 2200 during insertion of the spacer into the predetermined surgical space. In this embodiment, the graft blocks 3100 are paired and are generally mirror images of each other. Each graft block 3100 is configured to enclose a graft opening of a spacer and therefore may assume other shapes as required for this function. Here the graft blocks 3100 are in the form of generally rectangular shaped paddles 3101 with containing face 3105 facing opening 2232 of spacer 2200. Paddle arm 3102 extends from paddle 3101 and terminates in handle 3103 for grasping by surgeon. The handle portion may be enlarged and may be knurled or include other textures to improve grip. At the distal end of paddle 3101 is stop face 3104 for abutting bone or other mechanical stops. One or more channel locks 3106 align the graft block within the inserter tool 3000 and spacer 2200. In this embodiment, the channel locks 3106 are in the form of opposing alignment bosses 3110 shaped for capture and sliding engagement within channels 3002 or 3003 of longitudinal guide 3001. Although channel lock 3106 is illustrated here in the form of a T-shaped complementary engagement, other shapes and forms may be assumed. Channel lock 3106 may include a butt face 3111 to abut against a stop on spacer to indicate proper paddle alignment over the graft apertures.

Relief groove 3107 may be provided to assist sliding of paddles 3101 along guide bar body 2630 and to provide deflection of paddle 3101 to accommodate various sizes of spacers 2200. Spacing wall 3108 distances paddle 3101 a predetermined distance from axis-B sufficient for paddle to cover the graft opening. Bottom paddle surface 3109 glides along bottom surface of channel 3002 or 3003.

Figure 36:
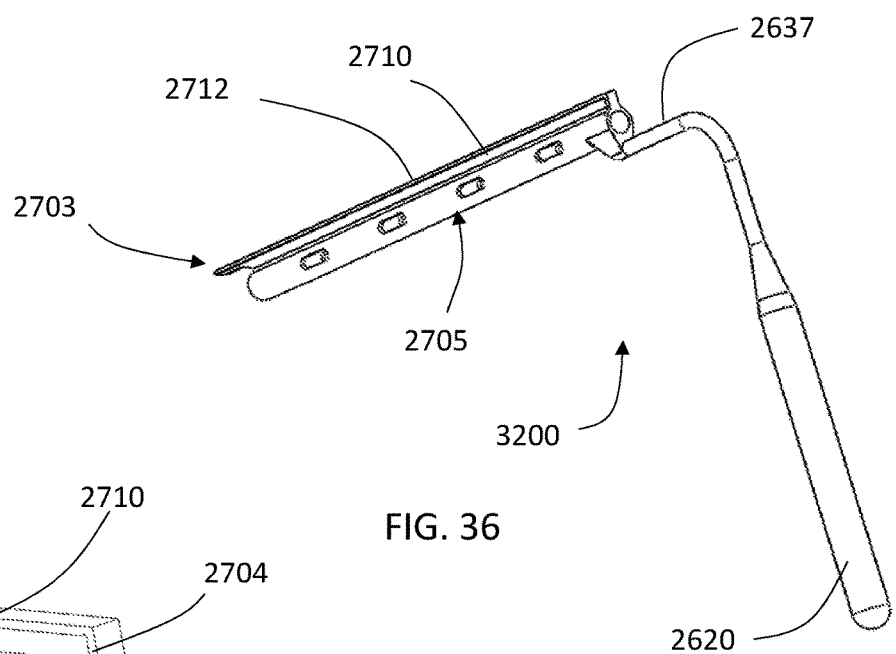
FIG. 36 is a perspective view of a preferred drill guide.
Figure 37A:
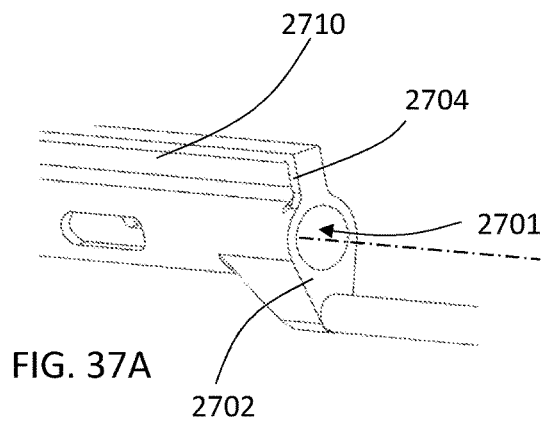
FIG. 37A is a close-up proximal perspective view of the drill guide of FIG. 36.
Figure 37B:
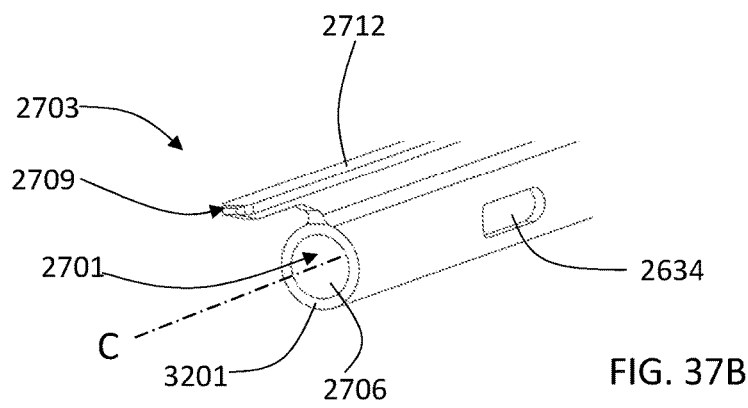
FIG. 37B is a close-up distal perspective view of the drill guide of FIG. 36.
Figure 49:
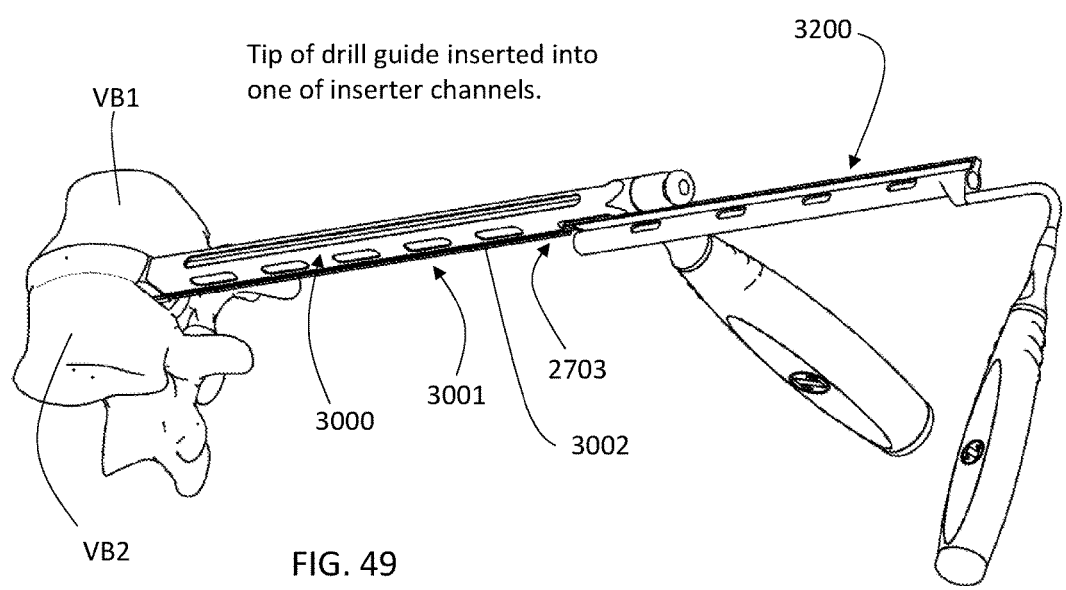
FIG. 49 is a partial perspective view of the drill guide inserted into an inserter channel.
Figure 50:
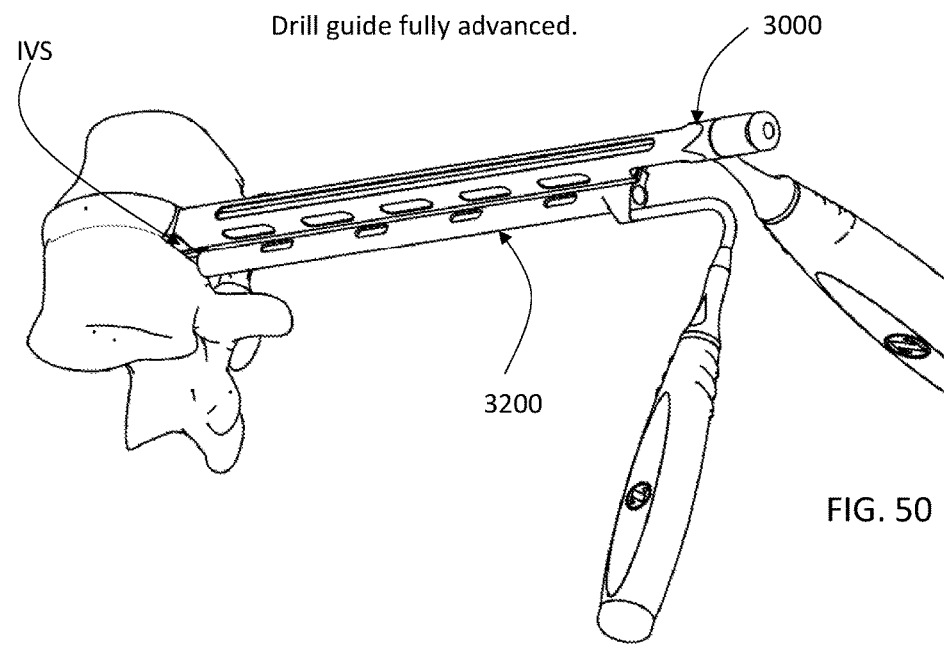
FIG. 50 is a partial perspective view of the drill guide fully advanced on the inserter and prepared for entry of the drill.
Figure 51:
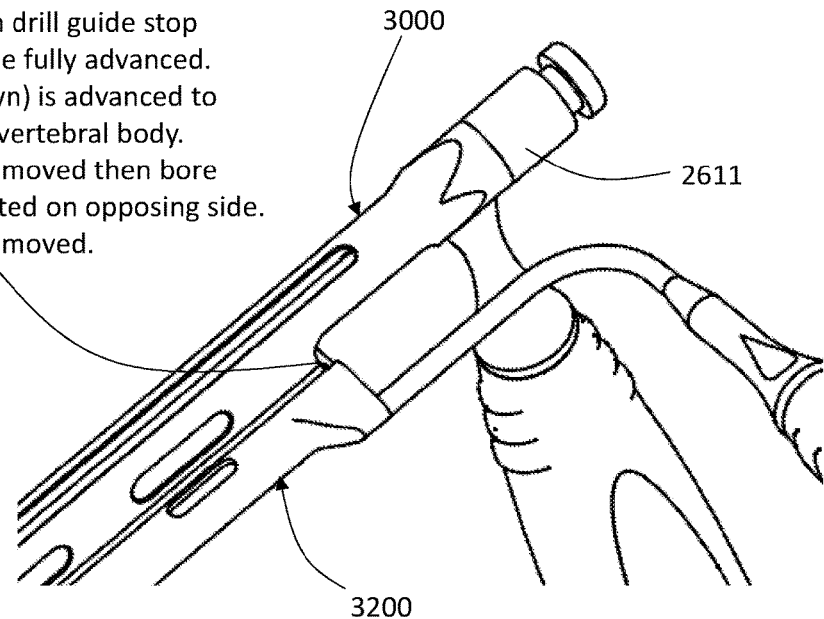
FIG. 51 is a partial close-up view illustrating the drill guide stop fully advanced.

Illustrated in FIGS. 36-38 is drill guide 3200 configured for compatibility with inserter 3000 wherein drill guide 3200 is an alternative to drill guide 2700. During portions of surgery, drill guide 3200 is interconnected with the longitudinal guide 3001 of the spacer inserter tool 3000. This relationship assures the drill guide 3200 is held stable in the incision and accurately positioned on a predetermined bone portion site for drilling of a stabilizer hole. This combined drill guide-spacer inserter assembly is illustrated in FIG. 49-51.

Drill guide body 2705 (FIG. 36, 37A, 37B) spans between a drill guide tip 2703 and a drill guide shoulder 2702. The drill guide body 2705 has a drill guide wall 2706, the face of which in this case defines a drill guide cylinder 2701 to receive and guide a drill 2720 such as shown in FIG. 27D. Although the wall 2706 is illustrated as a continuous cylinder, the wall 2706 may be discontinuous. For example, the wall 2706 may be in the form of a plurality of tabs extending from the drill guide body 2705 yet still functioning to contain and guide the drill 2720. Preferably at the proximal end of the drill guide body 2705, although it could be positioned elsewhere, the drill guide shoulder 2702 is provided. This shoulder 2702 interfaces with a drill guide stop 2722 on the drill 2720 to stop penetration of the drill 2720 into the bone at a predetermined depth. The drill exits the distal cylinder face 3201 before engaging the vertebral body.

Tip 2703 (FIG. 36, 38) of this embodiment is distally located on drill guide body 2705 comprising similar features illustrated in FIG. 27C. As illustrated in FIG. 36, tip 2703 is configured in profile and size to fit within inserter channels 3002 and 3003 as well as spacer channels 2255, 2265. The drill guide tip 2703 of drill guide 3200 comprises a flat track or base wall 2712, a web wall 2710, and a base nose 2709. The base nose 2709 is tapered and radiused much like the stabilizer nose 2311 to simplify insertion into one of the channels 3002, 3003. The web wall 2710 extends upright from the base wall 2712 and is integrated into, or otherwise attached to, the drill guide body 2705, however in this embodiment, although not necessary, the web wall extends substantially the entire length of guide body 2705 parallel to axis-C. A drill guide stop 2704 is located near the proximal end of body 2705 at web wall 2710 and is in the form of a ridge extending out from the web wall 2710. Drill guide stop 2704 limits overinsertion of the drill guide once the stop 2704 abuts proximal channel surface 3004.

A bone drill, such as the one illustrated in FIG. 27D is compatible with drill guide 3200.

In view of the surgical technique described earlier, minor modifications to the technique are made when substituting tools such as inserter tool 3000, graft blocks 3100, and drill guide 3200. These surgical instruments as illustrated are also well suited for a lateral surgery approach but may be adapted for other surgical approaches.

Once again the technique begins by preparing the patient using standard pre-op procedures and the patient is positioned on the operating table laying with the lateral entry side facing superiorly. EMG monitoring may be used to steer away from nerves. Incisions from the lateral side to open access to the surgical site are made. Tissue dilators and/or retractor systems may be used to access the affected disc space along with access lighting. As described previously, the diseased disc material is removed and endplates are prepared.

Figure 38A:
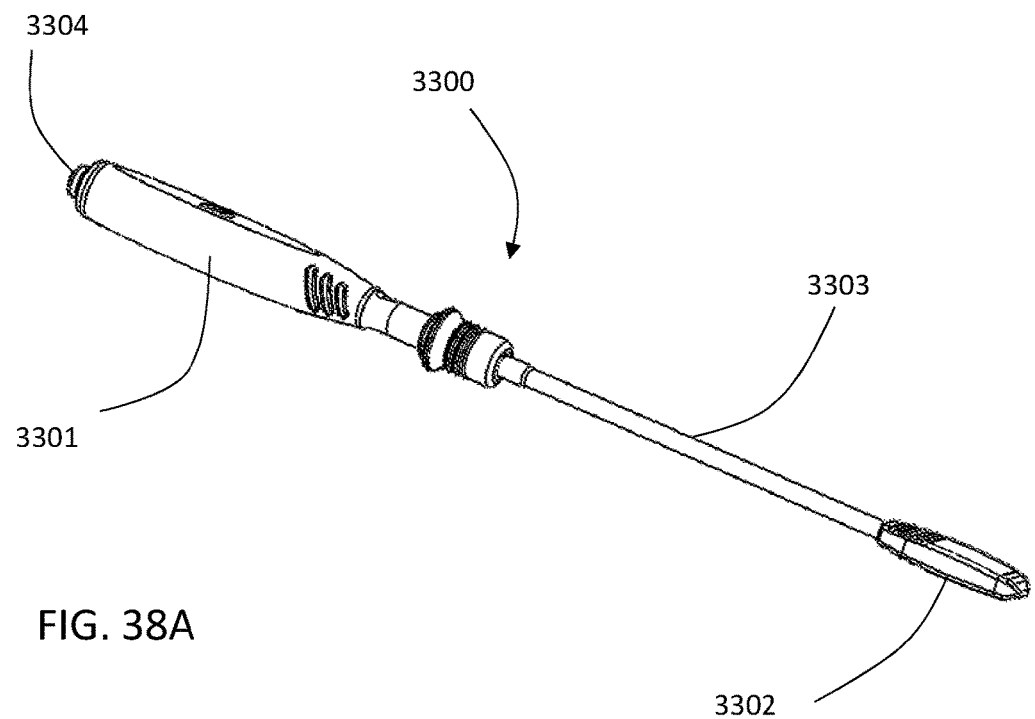
FIG. 38A is a side perspective view of a trial spacer.
Figure 38B:
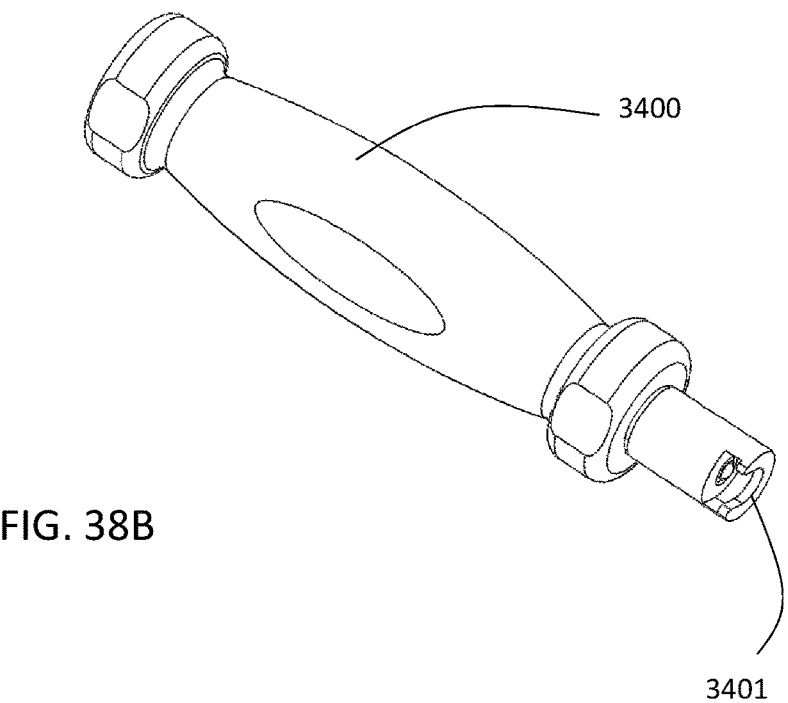
FIG. 38B is a side perspective view of an extension handle.

Trial spacers, such as the one illustrated in FIG. 38A may be used to correctly size the spacer and stabilizer required for the patent. When needed, extension handles such as the one illustrated in FIG. 38B may be serially attached to a distally placed handle to increase extension length.

Figure 39:
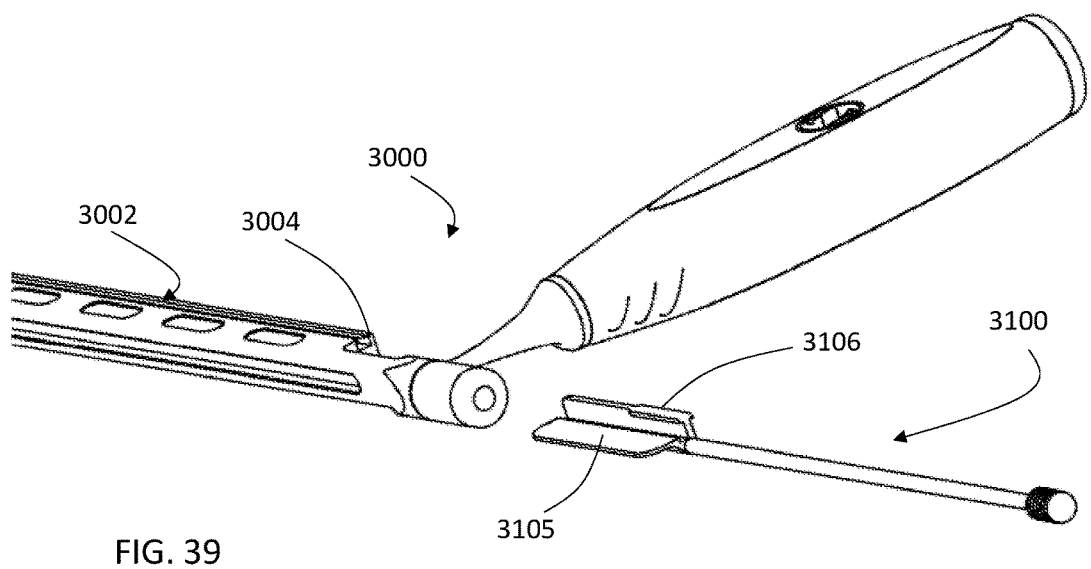
FIG. 39 is a proximal perspective view of a graft block preparing for insertion into a longitudinal guide of a spacer inserter.
Figure 40:
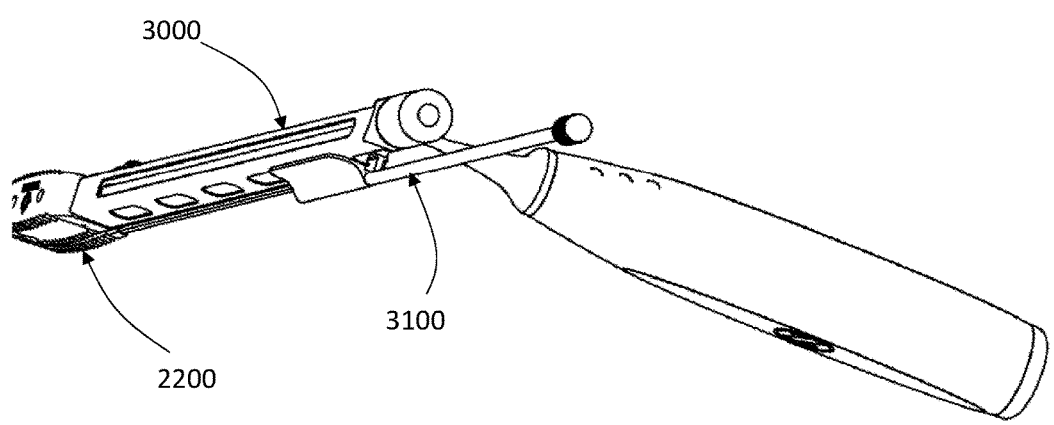
FIG. 40 is proximal perspective view of the graft block sliding down the inserter.
Figure 41:
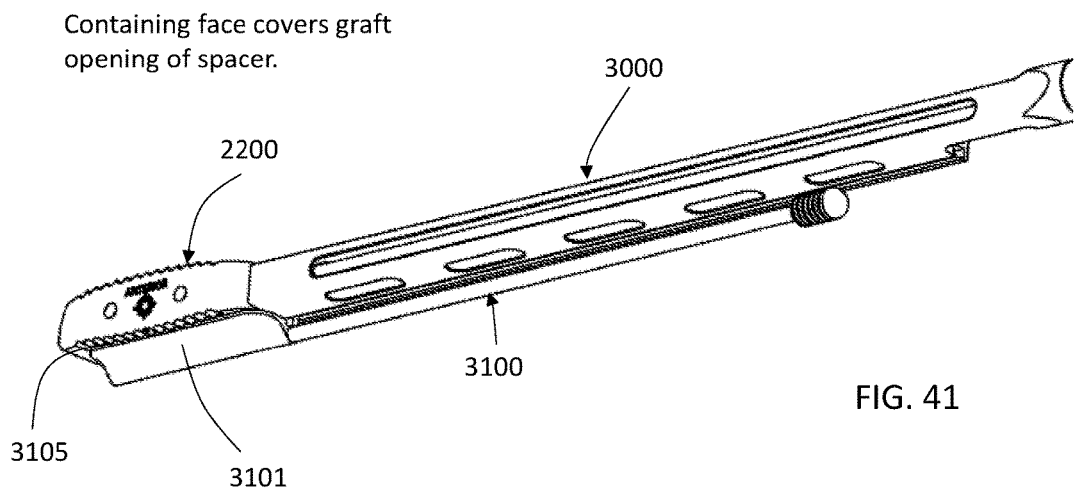
FIG. 41 is a partial perspective view of the containing face covering the graft opening.

The selected spacer is chosen from the surgical kit and secured to spacer inserter tool 3000 by advancing locking shaft as previously described. A graft block 3100 is chosen (FIG. 39-40), and with stop face 3104 facing distal, channel locks 3106 are inserted at the proximal channel surface 3004 of inserter 3000 into the appropriate T-shaped channel 3002 or 3003 and advanced distally until containing face 3105 covers spacer graft opening 2232 as illustrated in FIG. 41. Interference between alignment bosses 3110 on the graft block and portions of the inserter or spacer are utilized in some embodiments to stop the graft block at a predetermined position over the graft opening.

Figure 42:
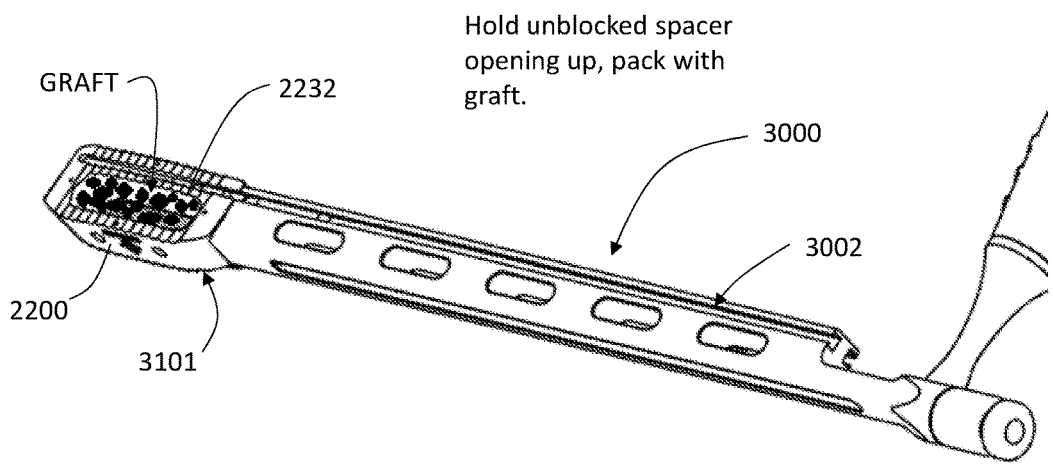
FIG. 42 is a partial perspective view of the spacer graft opening covered on an inferior side and ready to be packed with bone graft.

Holding the assembly so the unblocked spacer opening 2232 is facing up (FIG. 42) so that gravity can assist, the spacer opening 2232 may be packed with a chosen graft material.

Figure 43:
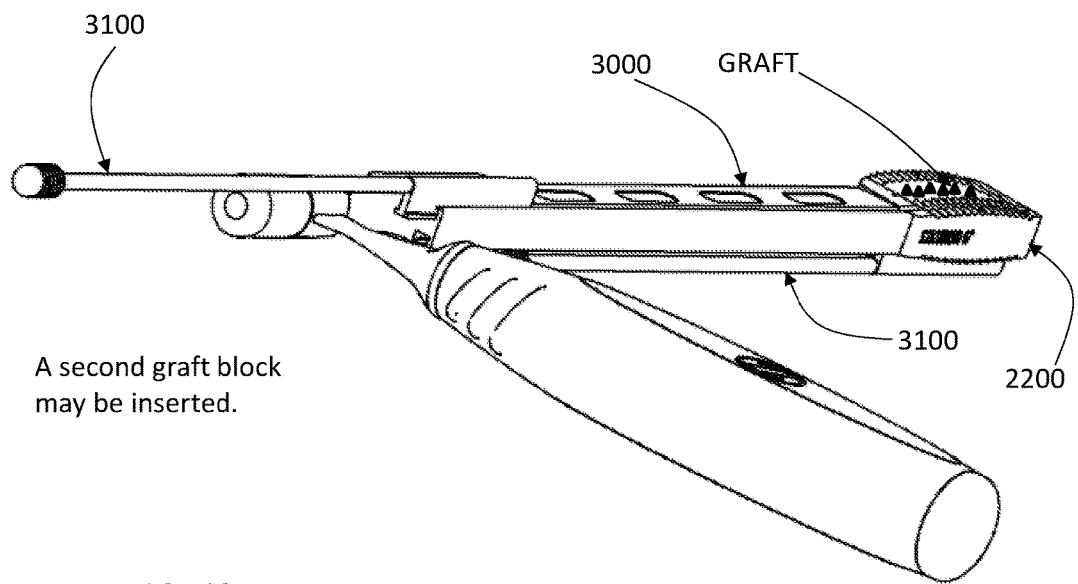
FIG. 43 is a partial proximal perspective view of a second graft block being loaded into the inserter.
Figure 44:
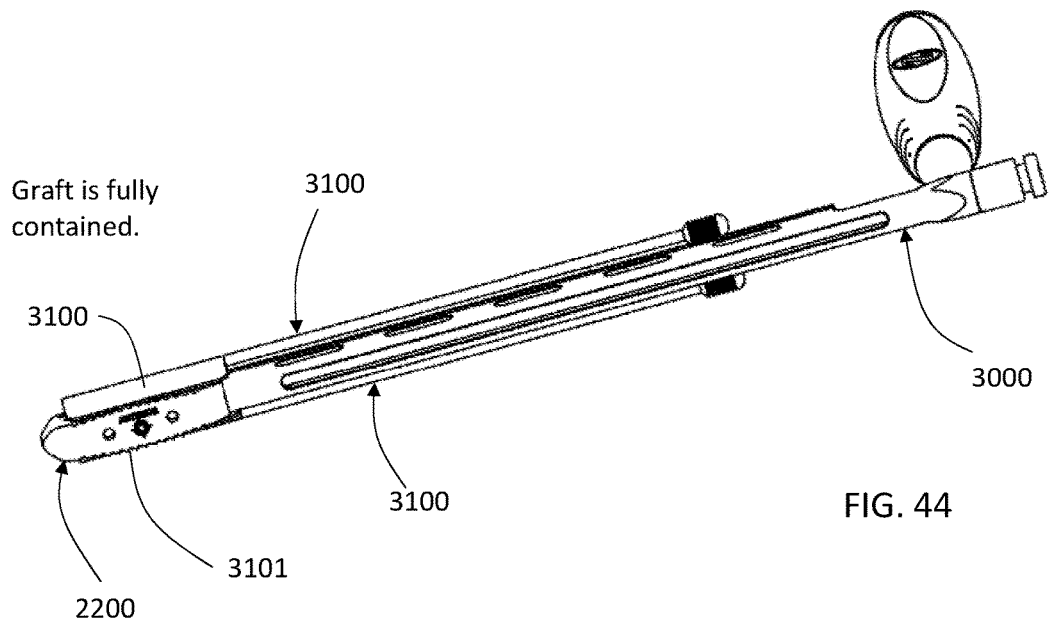
FIG. 44 is a partial perspective view of a spacer secured to the spacer inserter with graft blocks fully enclosing the graft opening of the spacer.

If the surgeon chooses, the second graft block 3100 is chosen with channel locks 3106 again inserted at the proximal channel surface 3004 of inserter 3000 into the available channel 3002 or 3003 (FIG. 43), and advanced distally wherein containing face 3105 covers spacer opening 2232. The graft should now be contained by the walls of the spacer and each graft block containing face 3105 (FIG. 44).

Figure 45:
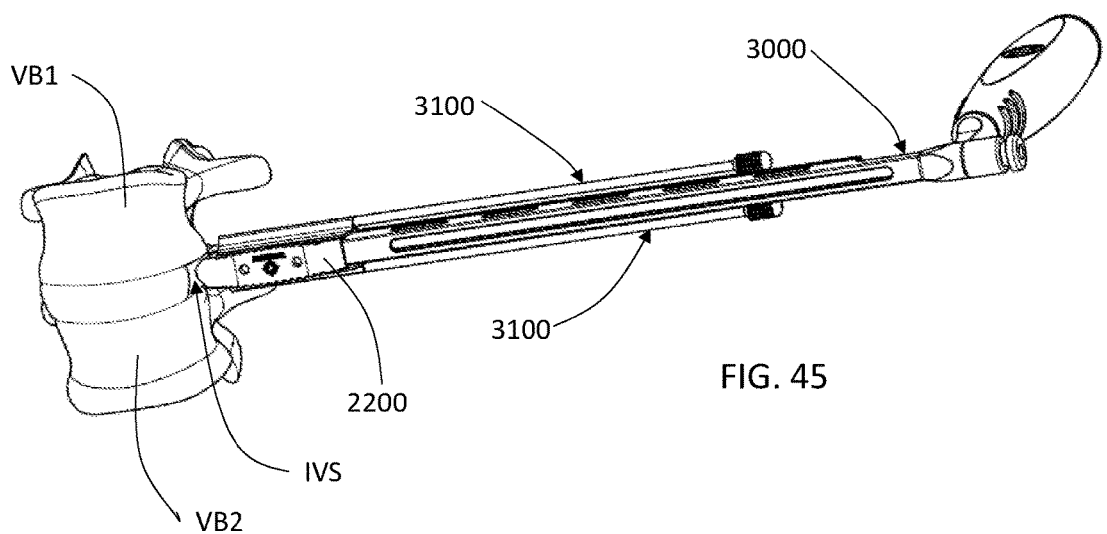
FIG. 45 is a partial perspective view of the stop faces of each graft block abutting the vertebral bodies just as the spacer begins entry into the intervertebral space.
Figure 46:
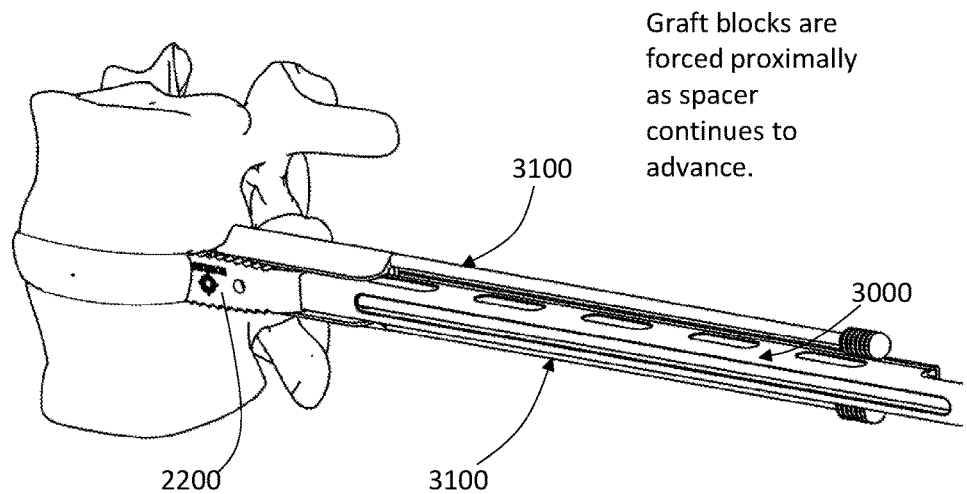
FIG. 46 is a partial perspective view of the graft blocks retracting as the spacer enters the intervertebral space.
Figure 47:
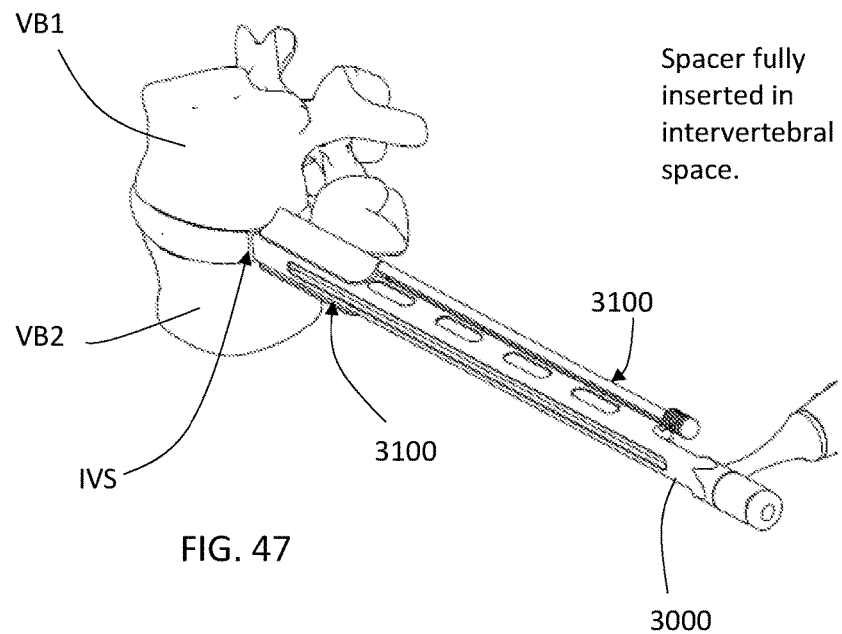
FIG. 47 is a partial perspective view of the spacer fully inserted into the intervertebral space.
Figure 48:
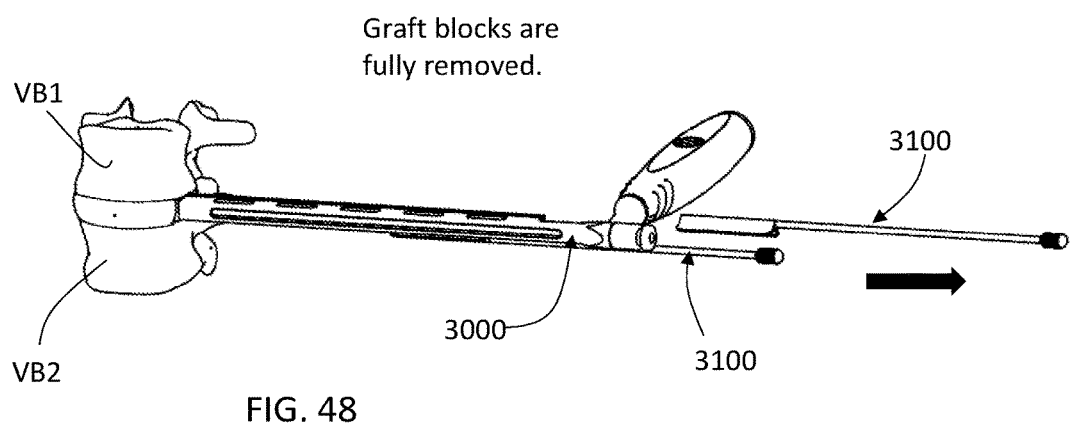
FIG. 48 is a perspective view of the graft blocks being removed from the surgical site.

The inserter tool with the selected spacer attached is then guided through the incision, down the corridor created by the retractor (not shown), with the leading end of the spacer wedging between the vertebral endplates (FIG. 45) and stop face 3104 of graft block 3100 abutting cortical bone wall of vertebral bodies VB1, VB2. As the spacer is advanced in the intervertebral space IVS, graft blocks 3100 are forced proximally (FIG. 46) until spacer has reached its predetermined position in the intervertebral space (FIG. 47). The graft blocks 3100 may now be removed from the surgical corridor by retracting them proximally (FIG. 48).

The tip 2703 of drill guide 3200 is then inserted into one of channels 3002 or 3003 (FIG. 49) and advanced distally until proximal channel surface 3004 abuts drill guide stop 2704 (FIG. 50-51). The tip 2703 is now engaged within one of the spacer channels/tracks 2255, 2265 of the spacer/cage 2200 assuring correct drill position with respect to the spacer.

A drill 2720 of predetermined diameter for chosen stabilizer is inserted into the cylinder 2701 of the drill guide 3200 creating a bore into the wall of the vertebrae by advancing the drill 2720 by hand or power into the drill guide cylinder until the drill stop 2722 abuts drill guide shoulder 2702 indicating the drill has reached a predetermined depth suitable for the stabilizer. The drill 2720 and guide 3200 are then removed. The procedure is duplicated on the opposing side to create a similar bore. The drill and guide are again removed. (As an alternative, the surgeon may opt to place a stabilizer 2300 in position within the $1_{st}$ drilled hole in the vertebral body before moving on to drill in the opposing vertebrae).

Figure 52:
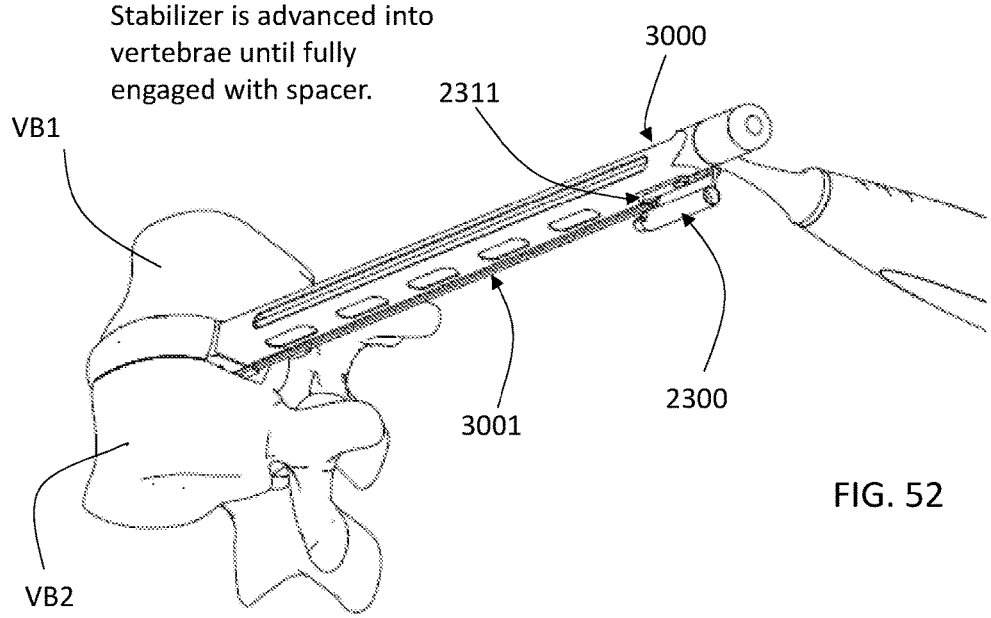
FIG. 52 is a partial perspective view illustrating the nose of a stabilizer advanced into a channel on the longitudinal guide (stabilizer inserter not shown).
Figure 53:
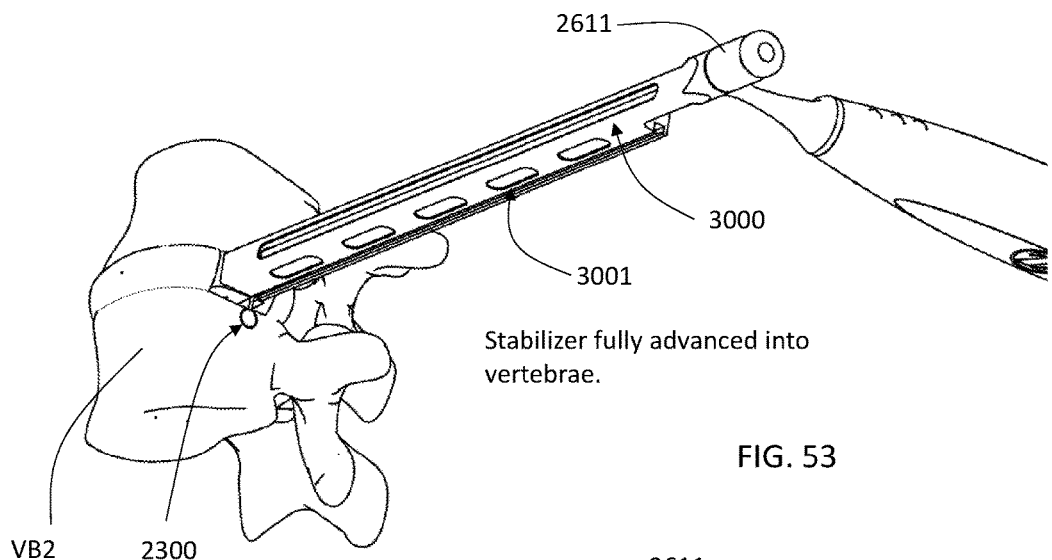
FIG. 53 is a partial perspective view of a stabilizer fully advanced into the predrilled hole in the vertebral body.

The selected stabilizer 2300 is now attached to a stabilizer inserter 2800 illustrated in FIGS. 28A and 28B by inserting the inserter's prong 2803 of insertion tip 2802 into the central bore 2331 of stabilizer 2300 and intermeshing with threads 2332. The base nose 2311 at the leading end of the stabilizer is then inserted into channel 3002 or 3003 of inserter tool 3000 (FIG. 52) and stabilizer 2300 is advanced into the bore created in the vertebrae until the stabilizer 2300 reaches the stabilizer stop 2276 and achieves an operative relationship with the spacer 2200 (FIG. 53). The stabilizer inserter 2800 is removed.

Figure 54:
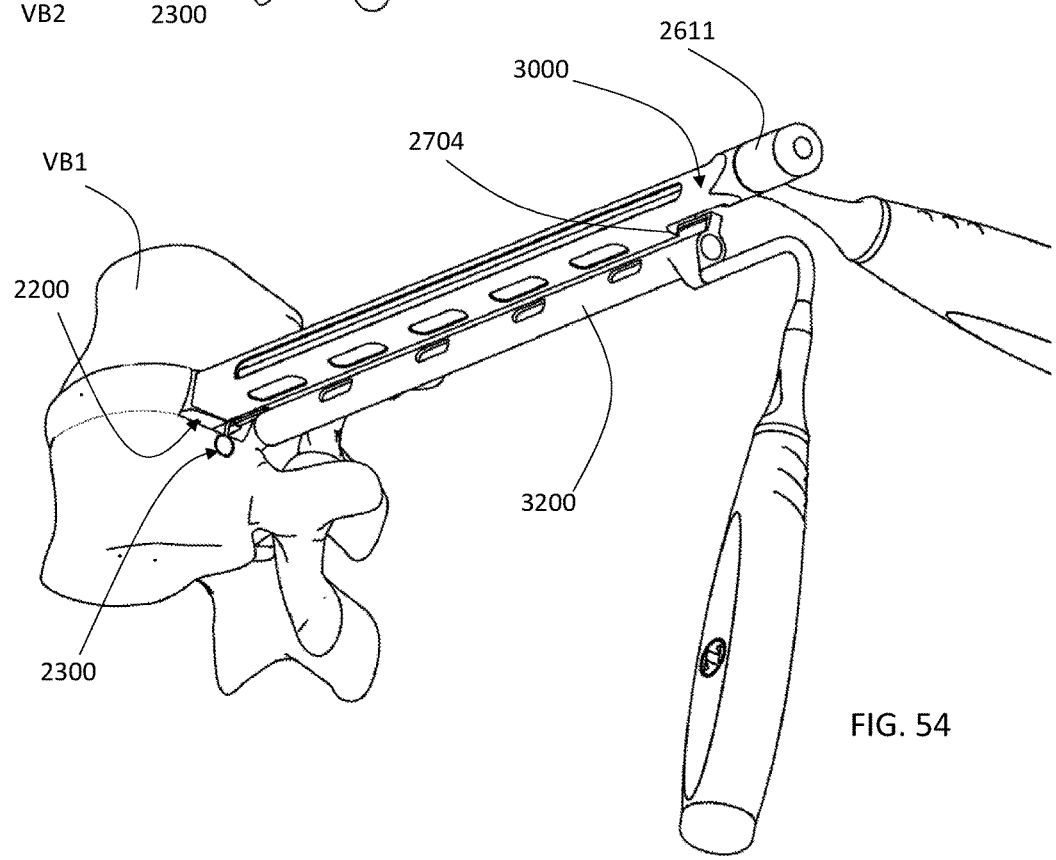
FIG. 54 is a partial perspective view of the drill guide reintroduced in preparation for the stabilizer spreader.
Figure 55:
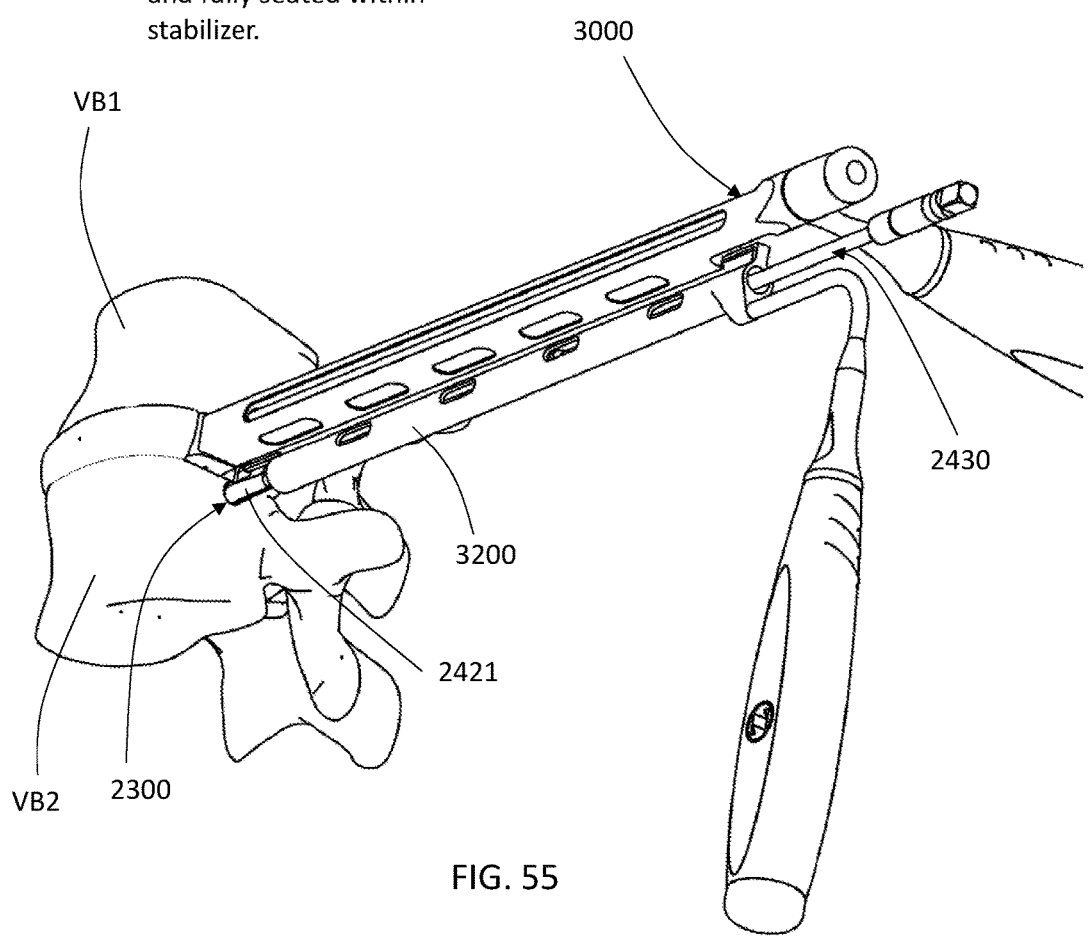
FIG. 55 is a partial perspective view of the spreader inserted in the drill guide and advanced into the stabilizer.

The drill guide 3200 is reinserted into the longitudinal guide 3001 and fully advanced (FIG. 54). A threaded spreader 2421 (FIG. 24B) attached to the spreader driver 2430 is advanced down drill guide 3200 and threaded into stabilizer threads 2332 until spreader 2421 is fully seated within stabilizer representing a locked state for the stabilizer 2300 (FIG. 56). The spreader driver 2430 and drill guide 3200 may now be removed and the procedure repeated on the opposing side until spacer 2200 and stabilizers 2300 are fully secured.

The spacer inserter tool 3000 and all instrumentation are removed and wound closure procedure may then be initiated.

Discussion of Alternatives

The device disclosed may be used in a variety of locations in the body—wherever there is a need to secure an implant to bone or bone fragments. For example, the device may be configured to secure the stemmed tibial plate in a total knee replacement surgery. The device is also well suited for stabilizing the sacral iliac joint. Other possible bone portion fusions include: ankle and subtalar fusions; MTP joint fusions of the great toe; opening wedge high tibial and distal tibial osteotomies; and metacarpal hand fusions. Spinal applications include cervical, thoracic and lumbar.

In the preferred embodiment, the stabilizer deflection gap is situated in a plane generally perpendicular to the web wall, thereby minimizing forces which may cause the vertebral body to crack. Alternatively other portions of the stabilizer cylindrical wall could be configured to expand and retain position. For example, the leading portion of the cylindrical wall could be longitudinally gapped to expand in diameter.

The device may be used at adjacent vertebral levels. In the preferred embodiment the cylindrical wall portion is kept near the endplate thereby leaving an adequate amount of the vertebral body bone between the adjacent level implants. Alternatively, the channels/keel tracks 2255/2265 could be staggered on the implant, thereby increasing distance between each stabilizer and thereby maximizing bone mass therebetween.

As an alternative, the reconfigurable body portion of the stabilizer can be deployed by a camming action rather than the spreader utilized in the preferred embodiment. A cam situated at the end of the spreader would deploy and lock the reconfigurable body tabs upon rotation of the camming spreader.

As another alternative, the upper and lower stabilizers may slidingly engage or otherwise interlock with each other, thereby relieving some of the forces endured by the channels or keel/tracks of the implant. Similarly, the upper and lower stabilizers may have a continuous web wall joining them. For example, this web may have a side lying flat track or base wall on the web to interconnect into a stabilizer attachment such as a keel track on the side of the implant body.

As another alternative, the implant body may be configured with more than one stabilizer attachment site to accommodate a plurality of stabilizers on one side. For example, the implant body portion could be modified for keel tracks on both sides of the graft portion. This configuration may be advantageous in an interbody device for anterior surgical approach.

As another alternative, the web wall is manufactured integral with the spacer and slides in with the implant wherein the cylindrical wall portion slides over the web into pre-drilled holes afterward.

Each of the described embodiments might be further modified by additionally using screws, adhesives, or other supplementary fixation structure.

Throughout, where there are cooperating components on separate elements, it is contemplated that the described placement of these components could be reversed. For example, the tabs/barbs 2350, shown on the stabilizers 2300, could be placed on the spacer/cage 2200 with the complementary undercut regions 2225 provided on the stabilizer 2300. Different combinations and numbers of these paired components can also be utilized.

Other mechanisms may be utilized to block the stabilizer in its operative relationship with the spacer. For example, detent arrangements, such as that utilizing a ball element, might be substituted for, or used in conjunction with, the described structure.

While the spacer is described above to be placed between adjacent bone portions before the stabilizer is moved from a pre-assembly relationship therewith into an operative relationship, the stabilizer could be put in place first followed by placement of the spacer. This is made possible through the use of a jig.

While assembly paths of all components are described as linear, this is also not a requirement. Further, the assembly paths for multiple stabilizers, while shown to be parallel, need not be so oriented.

It is also contemplated that structures features from all different embodiments are combinable in different combinations.

The foregoing disclosure of specific embodiments is intended to be illustrative of the broad concepts comprehended by the invention.

The foregoing invention has been described in accordance with the relevant legal standards, thus the description is exemplary rather than limiting in nature. Variations and modifications to the disclosed embodiment may become apparent to those skilled in the art and fall within the scope of the invention.

The invention claimed is:

1. A method of implanting a spacer implant within an intervertebral space and fixing with a stabilizer implant comprising the steps of:
   selecting an intervertebral spacer of a predetermined size for seating in an intervertebral space having an anchor portion comprising one or more channels extending from a proximal end;
   securing a spacer inserter tool to a proximal end of said intervertebral spacer with said anchor portion channel of said intervertebral spacer aligned with a spacer inserter channel on said spacer inserter tool;
   advancing said intervertebral spacer using said spacer inserter tool through a prepared incision until seated in an intervertebral space;
   inserting and distally advancing a tip of a drill guide into one of said spacer inserter channels on said spacer inserter tool for assuring correct drill position with respect to said intervertebral spacer;
   selecting a bone drill of predetermined diameter;
   advancing said drill into a cylinder of said drill guide and creating a bore of a predetermined depth through a wall of a corresponding vertebral body;
   removing said drill and said drill guide;
   selecting a first stabilizer implant;
   securing a stabilizer inserter to said first stabilizer implant;
   inserting a base wall of said first stabilizer implant into a spacer inserter channel on said spacer inserter tool and advancing said base wall whereby said stabilizer implant occupies the drilled vertebral body bore;
   removing said stabilizer inserter from said first stabilizer implant;
   reinserting and fully advancing said drill guide into and along said spacer inserter channel on said spacer inserter tool;
   securing a threaded spreader to a spreader driver;
   advancing said spreader driver and threaded spreader down a drill guide cylinder of said drill guide and into a central bore of said first stabilizer implant;
   and removing said spreader driver and said drill guide.

2. The method of claim 1 of implanting a spacer implant within an intervertebral space and fixing with a stabilizer implant further comprising the step of repeating on an opposing side of said intervertebral spacer the steps required to insert said first stabilizer and said first spreader for a second stabilizer and a second spreader.

3. The method of claim 2 of implanting a spacer implant within an intervertebral space and fixing with a stabilizer implant wherein the step of selecting an intervertebral spacer of a predetermined size for seating in an intervertebral space having an anchor portion comprising one or more channels extending from a proximal end further comprises the step of:
   selecting a spacer wherein said one or more channels are in the form of opposing T-slots with a first T-slot opening towards a first opposing surface on said spacer facing a first vertebral body and with a second T-slot opening towards a second opposing surface on said spacer facing a second vertebral body.

4. The method of claim 1 of implanting a spacer implant within an intervertebral space and fixing with a stabilizer implant wherein preceding the step of advancing said intervertebral spacer using said spacer inserter tool through a prepared incision until seated in an intervertebral space further comprises the steps of:
   choosing a first graft block and aligning and inserting a channel lock of said first graft block into said spacer inserter channel on said spacer inserter tool and advancing said first graft block distally until a containing face of said first graft block covers a spacer graft opening of said intervertebral spacer implant.

5. The method of claim 4 of implanting a spacer implant within an intervertebral space and fixing with a stabilizer implant further comprising the step of:
   packing a graft opening in said intervertebral spacer implant with one or more of bone graft and bone graft substitute preceding the step of advancing said intervertebral spacer using said spacer inserter tool through a prepared incision until seated in an intervertebral space.

6. The method of claim 5 of implanting a spacer implant within an intervertebral space and fixing with a stabilizer implant further comprising the steps of:
   inserting and advancing a second channel lock of a second graft block into a second spacer inserter channel thereby fully enclosing bone graft substitute within a graft opening of said intervertebral spacer following the step of packing a graft opening of said intervertebral spacer implant with one or more of bone graft and bone graft substitute.

7. The method of claim 6 of implanting a spacer implant within an intervertebral space and fixing with a stabilizer implant
   wherein the step of advancing said intervertebral spacer using said spacer inserter tool through a prepared incision until seated in an intervertebral space causes a consequent forcing of one or more of said first graft block and second graft block proximally.

8. The method of claim 7 of implanting a spacer implant within an intervertebral space and fixing with a stabilizer implant further comprising the step of fully removing said graft block prior to the step of inserting a drill guide.

9. The method of claim 1 of implanting a spacer implant within an intervertebral space and fixing with a stabilizer implant wherein the step of advancing said intervertebral spacer using said spacer inserter tool through a prepared incision until seated in an intervertebral space is preceded by and further comprises the step of using a tissue retractor to create a surgical corridor to the intervertebral space.

10. The method of claim 1 of implanting a spacer implant within an intervertebral space and fixing with a stabilizer implant wherein the step of advancing said drill into a cylinder of said drill guide and creating a bore into a wall of corresponding vertebral body further comprises the step of:
    advancing said drill until a drill stop on said drill abuts a drill guide shoulder indicating said drill has reached a predetermined depth suitable for seating said first stabilizer implant.

11. The method of claim 1 of implanting a spacer implant within an intervertebral space and fixing with a first stabilizer implant wherein the step of inserting a base wall of said stabilizer implant into a spacer inserter channel on said spacer inserter tool and advancing said base wall into an aligned intervertebral spacer channel of said intervertebral spacer using said stabilizer inserter wherein said stabilizer implant occupies said vertebral body bore further comprises the step of:
    advancing said stabilizer into the created vertebral bore until said stabilizer abuts a stabilizer stop in said intervertebral spacer.

12. The method of claim 1 of implanting a spacer implant within an intervertebral space and fixing with a first stabilizer implant wherein the step of inserting a base wall of said stabilizer implant into a spacer inserter channel on said spacer inserter tool and advancing said base wall into an aligned intervertebral spacer channel of said intervertebral spacer using said stabilizer inserter and wherein said stabilizer implant occupies said vertebral body bore further comprises the step of:
    advancing said stabilizer into the created vertebral bore and utilizing a web wall of a stabilizer implant having a sharp leading edge to cut through a cortical bone wall of a vertebral body.

13. The method of claim 1 of implanting a spacer implant within an intervertebral space and fixing with a stabilizer implant wherein the step of advancing said spreader driver and threaded spreader down a drill guide cylinder into a central bore of said stabilizer further comprises the step of:
    fully seating said threaded spreader within said stabilizer causing consequent spreading of said stabilizer's repositionable body tabs into surrounding bone.

14. The method of claim 1 of implanting a spacer implant within an intervertebral space and fixing with a stabilizer implant wherein the step of inserting and advancing a tip of a drill guide into one of said spacer inserter channels on said spacer inserter tool assuring correct drill position with respect to said intervertebral spacer further comprises the step of:
    engaging said drill guide tip within an aligned intervertebral spacer channel of said intervertebral spacer.

15. The method of claim 1 of implanting a spacer implant within an intervertebral space and fixing with a stabilizer implant wherein the step inserting a base wall of said stabilizer implant into a spacer inserter channel on said spacer inserter tool and advancing said base wall whereby said stabilizer implant occupies said vertebral body bore further comprises the step of:
    engaging said base wall of said stabilizer implant into an aligned intervertebral spacer channel of said intervertebral spacer using said stabilizer inserter.

16. The method of claim 15 of implanting a spacer implant within an intervertebral space and fixing with a stabilizer implant further comprising the step of:
    advancing said base wall within a spacer inserter channel wherein one or more self-retaining clips extends into an undercut region of said spacer inserter channel to prevent unintentional back out of said stabilizer implant from said spacer implant.

17. The method of claim 15 of implanting a spacer implant within an intervertebral space and fixing with a stabilizer implant further comprising the step of:
    advancing said base wall within a spacer inserter channel wherein one or more self-retaining clips becomes blocked by a blocking surface to block said stabilizer from backing out.

18. A method of claim 1 of implanting a spacer implant within an intervertebral space and fixing with a stabilizer implant wherein the step of securing a spacer inserter tool to a proximal end of said intervertebral spacer with said anchor portion channel of said intervertebral spacer aligned with a spacer inserter channel on said spacer inserter tool further comprises the step of:
    aligning and inserting a first prong of a connection tip portion of said spacer inserter tool in a first attachment hole at a proximal end of said intervertebral spacer implant.

19. A method of claim 1 of implanting a spacer implant within an intervertebral space and fixing with a stabilizer implant wherein the step of securing a spacer inserter tool to a proximal end of said intervertebral spacer with said anchor portion channel of said intervertebral spacer aligned with a spacer inserter channel on said spacer inserter tool further comprises the step of:
    advancing a locking shaft having a threaded prong of a connection tip portion of said spacer inserter tool in a threaded attachment hole at a proximal end of said intervertebral spacer implant wherein an inserter face of spacer inserter tool is fixed against a proximal face of said spacer.

20. A method of claim 19 of implanting a spacer implant within an intervertebral space and fixing with a stabilizer implant wherein the step of aligning and
    advancing a locking shaft having a threaded prong of a connection tip portion of said spacer inserter tool in a threaded attachment hole at a proximal end of said intervertebral spacer implant wherein an inserter face is fixed against a proximal face of said spacer further comprises the step of:
    applying a torsional force to a threaded spool located at a proximal end of said locking shaft.

\* \* \* \* \*